(12) United States Patent
Natarajan et al.

(10) Patent No.: US 7,238,671 B2
(45) Date of Patent: *Jul. 3, 2007

(54) HUMAN GLUCAGON-LIKE-PEPTIDE-1 MIMICS AND THEIR USE IN THE TREATMENT OF DIABETES AND RELATED CONDITIONS

(75) Inventors: Sesha Iyer Natarajan, Hillsborough, NJ (US); Claudio Mapelli, Plainsboro, NJ (US); Margarita M. Bastos, Plainsboro, NJ (US); Michael Bernatowicz, Princeton, NJ (US); Ving Lee, Hamilton, NJ (US); William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/419,399

(22) Filed: Apr. 21, 2003

(65) Prior Publication Data

US 2004/0127423 A1    Jul. 1, 2004

Related U.S. Application Data

(63) Continuation-in-part of application No. 10/273,975, filed on Oct. 18, 2002.

(60) Provisional application No. 60/342,015, filed on Oct. 18, 2001.

(51) Int. Cl.
| | | |
|---|---|---|
| A61K 38/08 | (2006.01) | |
| C07K 7/04 | (2006.01) | |
| A61K 38/00 | (2006.01) | |
| A61K 38/02 | (2006.01) | |
| A61K 38/16 | (2006.01) | |
| C07K 2/00 | (2006.01) | |
| C07K 7/08 | (2006.01) | |
| C07K 1/00 | (2006.01) | |
| C07K 1/14 | (2006.01) | |
| C07K 1/107 | (2006.01) | |

(52) U.S. Cl. .............................. 514/17; 514/2; 514/13; 514/14; 514/15; 514/16; 530/300; 530/326; 530/327; 530/328; 530/329; 530/330; 530/333; 530/344; 530/345

(58) Field of Classification Search .................... 514/2, 514/13–15; 530/300, 326, 327
See application file for complete search history.

(56) References Cited

U.S. PATENT DOCUMENTS

| | | | |
|---|---|---|---|
| 3,674,836 A | 7/1972 | Creger | |
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,448,784 A | 5/1984 | Glamkowski et al. | |
| 4,450,171 A | 5/1984 | Hoffman et al. | |
| 4,499,289 A | 2/1985 | Baran et al. | |
| 4,613,610 A | 9/1986 | Wareing | |
| 4,647,576 A | 3/1987 | Hoefle et al. | |
| 4,681,893 A | 7/1987 | Roth | |
| 4,686,237 A | 8/1987 | Anderson | |
| 4,759,923 A | 7/1988 | Buntin et al. | |
| 4,871,721 A | 10/1989 | Biller | |
| 4,924,024 A | 5/1990 | Biller | |
| 4,966,848 A | * 10/1990 | Smith et al. ................. | 435/193 |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,223,421 A | * 6/1993 | Smith et al. ................. | 435/193 |
| 5,260,440 A | 11/1993 | Hirai et al. | |
| 5,273,995 A | 12/1993 | Roth | |
| 5,354,772 A | 10/1994 | Kathawala | |
| 5,385,929 A | 1/1995 | Bjorge et al. | |
| 5,488,064 A | 1/1996 | Sher | |
| 5,491,134 A | 2/1996 | Sher et al. | |
| 5,506,219 A | 4/1996 | Robl | |
| 5,541,204 A | 7/1996 | Sher et al. | |

(Continued)

FOREIGN PATENT DOCUMENTS

EP        0142146       5/1985

(Continued)

OTHER PUBLICATIONS

Ashworth, D.M. et al., "2-Cyanopyrrolidides as Potent, Stable Inhibitors of Dipeptidyl Peptidase IV", Bioorganic & Medicinial Chemistry Letters, vol. 6, No. 10, pp. 1163-1166 (1996).

(Continued)

*Primary Examiner*—Cecilia J. Tsang
*Assistant Examiner*—Andrew D. Kosar
(74) *Attorney, Agent, or Firm*—Brian C. Carey

(57) ABSTRACT

The present invention provides novel human glucagon-like peptide-1 (GLP-1) peptide mimics that mimic the biological activity of the native GLP-1 peptide and thus are useful for the treatment or prevention of diseases or disorders associated with GLP activity. Further, the present invention provides novel, chemically modified peptides that not only stimulate insulin secretion in type II diabetics, but also produce other beneficial insulinotropic responses. These synthetic peptide GLP-1 mimics exhibit increased stability to proteolytic cleavage making them ideal therapeutic candidates for oral or parenteral administration.

19 Claims, 7 Drawing Sheets

U.S. PATENT DOCUMENTS

| | | | |
|---|---|---|---|
| 5,594,016 | A | 1/1997 | Ueno et al. |
| 5,595,872 | A | 1/1997 | Wetterau, II et al. |
| 5,612,359 | A | 3/1997 | Murugesan |
| 5,614,492 | A | 3/1997 | Habener |
| 5,686,104 | A | 11/1997 | Mills et al. |
| 5,691,322 | A | 11/1997 | Robl |
| 5,712,279 | A | 1/1998 | Biller et al. |
| 5,712,396 | A | 1/1998 | Magnin et al. |
| 5,739,135 | A | 4/1998 | Biller et al. |
| 5,753,675 | A | 5/1998 | Wattanasin |
| 5,760,246 | A | 6/1998 | Biller et al. |
| 5,770,615 | A | 6/1998 | Cheng et al. |
| 5,776,983 | A | 7/1998 | Washburn et al. |
| 5,827,875 | A | 10/1998 | Dickson, Jr. et al. |
| 5,837,218 | A * | 11/1998 | Peers et al. ............... 424/1.69 |
| 5,885,983 | A | 3/1999 | Biller et al. |
| 5,962,440 | A | 10/1999 | Sulsky |
| 5,998,375 | A | 12/1999 | Thogersen et al. |
| 6,043,265 | A | 3/2000 | Murugesan et al. |
| 6,344,180 | B1 * | 2/2002 | Holst et al. ................ 424/9.1 |
| 6,548,667 | B2 | 4/2003 | Park et al. |
| 6,737,417 | B2 | 5/2004 | Jo et al. |
| 2002/0019419 | A1 | 2/2002 | De Laszlo et al. |

FOREIGN PATENT DOCUMENTS

| | | |
|---|---|---|
| EP | 0221025 | 5/1987 |
| EP | 0 955 314 A2 | 11/1999 |
| FR | 2596393 | 10/1987 |
| GB | 2205837 | 12/1988 |
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 98/08871 A | 3/1998 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 00/12116 A | 3/2000 |
| WO | WO 00/34331 A | 6/2000 |
| WO | WO 00/34332 | 6/2000 |
| WO | WO 00/28067 A9 | 10/2000 |
| WO | WO 03/033671 A | 4/2003 |
| WO | WO 2004/094461 | 11/2004 |

OTHER PUBLICATIONS

Ashworth, D.M. et al., "4-Cyanothiazolidides as Very Potent, Stable Inhibitors of Dipeptidyl Peptidase IV", Bioorganic & Medicinial Chemistry Letters, vol. 6, No. 22, pp. 2745-2748 (1996).

Atherton, E. et al., "The Fluorenylmethoxycarbonyl Amino Protecting Group", The Peptides: Analysis, Synthesis, Biology, vol. 9, Special Methods in Peptide Synthesis, Part C, Academic Press, Inc., Udenfriend, S. and Meienhofer, J., eds., pp. 1-38 (1987).

Barany, G. et al., "Solid-Phase Peptide Synthesis", The Peptides: Analysis, Synthesis, Biology, vol. 2, Special Methods in Peptide Synthesis, Part A, Academic Press, Gross, E. and Meienhofer, J., eds., pp. 1-284 (1980).

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, pp. 1-40 (1996).

Burgess, K. et al., "Solid Phase Syntheses of Oligoureas", J. Am. Chem. Soc., vol. 119, pp. 1556-1564 (1997).

Byrne, M.M. et al., "Inhibitory effects of hyperglycaemia on fed jejunal motility: potential of hyperinsulinaemia", European Journal of Clinical Investigation, vol. 28, pp. 72-78 (1998).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Corey, E.J. et al., "Application of Unreactive Analogs of Terpenoid Pyrophosphates to Studies of Multistep Biosynthesis., etc.", Journal of the American Chemical Society, vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, pp. 11-20 (1999).

Davern, P. et al., "Chemical and Biological Reactivity of Sulfamidopenicillins", J. Chem. Soc. Perkin Trans., vol. 2, pp. 381-387 (1994).

Fehrentz, J.-A. et al., "An Efficient Synthesis of Optically Active α-(t-Butoxycarbonylamino)-aldehydes from α-Amino Acids", Synthesis, pp. 676-678 (1983).

Fingl, E. et al., "Introduction", The Pharmacological Basis of Therapeutics, Fifth Edition, Macmillan Publishing Co., Inc., Goodman, L.S. et al., eds., pp. 1-46 (1975).

Flint, A. et al., "Glucagon-like Peptide 1 Promotes Satiety and Suppresses Energy Intake in Humans", J. Clin. Invest., vol. 101, No. 3, pp. 515-520 (1998).

Gennaro, A.R., ed., Remington's Pharmaceutical Sciences, 18th Edition, Mack Publishing Company, pp. xv-xvi (1990).

Gennaro, A.R., ed., Remington: Practice of the Science and Pharmacy, 19th Edition, Mack Publishing Company, pp. xv-xvi (1995).

Gennaro, A.R., ed., Remington: Practice of the Science and Pharmacy, 19th Edition, vol. II, Mack Publishing Company, pp. vii-viii (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Gutzwiller, J.-P. et al., "Glucagon-like peptide-1: a potent regulator of food intake in humans", Gut, vol. 44, pp. 81-86 (1999).

Hara, S., "Ileal $Na^+$/bile acid cotransporter inhibitors", Drugs of the Future, vol. 24, No. 4, pp. 425-430 (1999).

Holst, J.J., "Glucagon-like Peptide-1, A Gastrointestinal Hormone with a Pharmacological Potential", Current Medicinal Chemistry, vol. 6, pp. 1005-1017 (1999).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinial Endocrinology and Metabolism, vol. 82, No. 3, pp. 727-734 (1997).

King, D.S. et al., "A cleavage method which minimizes side reactions following Fmoc solid phase peptide synthesis", Int. J. Peptide Protein Res., vol. 36, pp. 255-266 (1990).

Krause, B.R. et al., "ACAT Inhibitors: Physiologic Mechanisms for Hypolipidemic and Anti-Atherosclerotic Activities in Experimental Animals", Inflammation: Mediators and Pathways, CRC Press Inc., Ruffolo, Jr., R.R. and Hollinger, M.A., eds., pp. 173-198 (1995).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-60 (PPAR-α) and PPAR-γ., etc.", Diabetes, vol. 47, pp. 1841-1847 (1998).

Näslund, E. et al., "Energy intake and appetite are suppressed by glucagon-like peptide-1 (GLP-1) in obese men", International Journal of Obesity, vol. 23, pp. 304-311 (1999).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rosenblum, S.B. et al., "Discovery of 1-(4-Fluorophenyl)-(3R)-[3-(4-fluorophenyl)-(3S)-hydroxypropyl]-(4S)-(4-hydroxphenyl)-2-azetidinone (SCH 58235): A Designed, Potent, Orally Active Inhibitor of Cholesterol Absorption", J. Med. Chem., vol. 41, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders, ACAT Inhibitor", Drugs of Future, vol. 24, No. 1, pp. 9-15 (1999).

Stewart, J.M. et al., eds., Solid Phase Peptide Synthesis, Second Edition, Pierce Chemical Company, pp. vii-xi, 92 (1984).

Stoffers, D.A. et al., "Insulintropic Glucagon-Like Peptide 1 Agonists Stimulate Expression of Homeodomain Protein IDX-1 and Increase Islet Size in Mouse Pancreas", Diabetes, vol. 49, pp. 741-748 (2000).

Stout, D.M.; "Inhibitors of Acyl-CoA:Cholesterol O-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Wettergren, A. et al., "Truncated GLP-1 (Proglucagon 78-107-Amide) Inhibits Gastric and Pancreatic Functions in Man", Digestive Diseases and Sciences, vol. 38, No. 4, pp. 665-673 (1993).

Yamada, M. et al., "A Potent Dipeptide Inhibitor of Dipeptidyl Peptidase IV", Bioorganic & Medicinal Chemistry Letters, vol. 8, pp. 1537-1540 (1998).

U.S. Appl. No. 11/170,968, filed Jun. 30, 2005, Ewing et al.

U.S. Appl. No. 11/172,488, filed Jun. 30, 2005, Mathur et al.

Fehder, W. P., et al., "Development and Evaluation of a Chromatographic Procedure for Partial Purification of Substance P with Quantitation by Enzyme Immunoassay", Clinical and Diagnostic Laboratory Immunology, vol. 5(3), pp. 303-307, (1998).

Gluschankof, P., et al., Enzymes processing somatostatin precursors: An Arg-Lys esteropeptidase from the rat brain cortex converting somatostatin-28 into somatostatin-14, proc. Natl. Acad., Sci., vol. 81, pp. 6662-6666, (1984).

Ito, Yutaka, et al., "Difference in cholesterol-binding and cytolytic activities between listerlolysin O and seeligeriolysin O: a possible role of alanine residue in tryptophan-rich undecapeptide", FEMS Microbiology Letters, vol. 203, pp. 185-189, (2001).

* cited by examiner

Effects of intravenous infusion of Compound-A and GLP-1 on plasma glucose in scGTT in rats

Effects of intravenous infusion of Compound A and GLP-1 on plasma glucose in scGTT in rats Effects of intravenous infusion of Compound B and GLP-1 on plasma glucose in scGTT in rats Effects of subcutaneous injection of Compound A and GLP-1 on plasma glucose in scGTT in rats Effects of subcutaneous injection of Compound B and GLP-1 on plasma glucose in scGTT in rats Effects of subcutaneous injection of Compound C on plasma glucose in an ipGTT model in rats.

Effects of subcutaneous injection of Compound D on plasma glucose in an ipGTT model in rats.

Effects of subcutaneous injection of GLP-1 on plasma glucose in an ipGTT model in rats.

HUMAN GLUCAGON-LIKE-PEPTIDE-1 MIMICS AND THEIR USE IN THE TREATMENT OF DIABETES AND RELATED CONDITIONS

This application is a continuation-in-part of U.S. Ser. No. 10/273,975 filed Oct. 18, 2002, which claims the benefit of provisional application U.S. Ser. No. 60/342,015, filed Oct. 18, 2001, the disclosures of which are hereby incorporated by reference herein in its entirety.

FIELD OF THE INVENTION

The present invention provides novel human glucagon-like peptide-1 (GLP-1) peptide mimics, which duplicate the biological activity of the native peptide, exhibit increased stability to proteolytic cleavage as compared to GLP-1 native sequences, and thus are useful for the amelioration of the diabetic condition.

BACKGROUND OF THE INVENTION

GLP-1 is an important gut hormone with regulatory function in glucose metabolism and gastrointestinal secretion and metabolism. Human GLP-1 is a 30 amino acid residue peptide originating from preproglucagon, which is synthesized for example, in the L-cells in the distal ileum, in the pancreas and in the brain. Processing of preproglucagon to yield GLP-1(7-36)amide and GLP-2 occurs mainly in the L-cells. GLP-1 is normally secreted in response to food intake, in particular carbohydrates and lipids stimulate GLP-1 secretion. GLP-1 has been identified as a very potent and efficacious stimulator for insulin release. GLP-1 lowers glucagon concentration, slows gastric emptying, stimulates insulin biosynthesis and enhances insulin sensitivity (Nauck, 1997, Horm. Metab. Res. 47:1253-1258). GLP-1 also enhances the ability of the B-cells to sense and respond to glucose in subjects with impaired glucose tolerance (Byrne, Eur. J. Clin. Invest., 28:72-78, 1998). The insulinotropic effect of GLP-1 in humans increases the rate of glucose metabolism partly due to increased insulin levels and partly due to enhanced insulin sensitivity (D'Alessio, Eur. J. Clin. Invest., 28:72-78, 1994). The above stated pharmacological properties of GLP-1 make it a highly desirable therapeutic agent for the treatment of type-II diabetes. Additionally, recent studies have shown that infusions of slightly supra-physiological amounts of GLP-1 significantly enhance satiety and reduce food intake in normal subjects (Flint, A., Raben, A., Astrup, A. and Holst, J. J., J. Clin. Invest, 101:515-520, 1998; Gutswiller, J. P., Goke, B., Drewe, J., Hildebrand, P., Ketterer, S., Handschin, D., Winterhaider, R., Conen, D and Beglinger, C. Gut 44:81-86, 1999;). The effect on food intake and satiety has also been reported to be preserved in obese subjects (Naslund, E., Barkeling, B., King, N., Gutniak, M., Blundell, J. E., Holst, J. J., Rossner, S., and Hellstrom, P. M., Int. J. Obes. Relat. Metab. Disord., 23:304-311, 1999). In the above-cited studies a pronounced effect of GLP-1 on gastric emptying was also suspected to occur. Gastric emptying results in post-prandial glucose excursions. It has also been shown that in addition to stimulation of insulin secretion, GLP-1 stimulates the expression of the transcription factor IDX-1 while stimulating B-cell neogenesis and may thereby be an effective treatment and/or preventive agent for diabetes (Stoffers, D. A., Kieffer, T. J. Hussain, M. A., Drucker, D. J., Bonner-Weir, S., Habener, J. F. and Egan, J. M. Diabetes, 40:741-748, 2000). GLP-1 has also been shown to inhibit gastric acid secretion (Wettergren, A., Schjoldager, B., Mortensen, P. E., Myhre, J., Christiansen, J., Holst, J. J., Dig. Dis. Sci., 38:665-673, 1993), which may provide protection against gastric ulcers.

GLP-1 is an incretin hormone, for example, an intestinal hormone that enhances meal-induced insulin secretion (Holst, J. J., Curr. Med. Chem., 6:1005-1017, 1999). It is a product of the glucagon gene encoding proglucagon. This gene is expressed not only in the A-cells of the pancreas but also in the endocrine L-cells of the intestinal mucosa. Proglucagon is a peptide (protein) containing 160 amino acids. Further processing of proglucagon results in the generation of a) glucagon, b) an N-terminal, presumably inactive fragment, and c) a large C-terminal fragment commonly referred as "the major proglucagon fragment". This fragment is considered to be biologically inactive. Even though this fragment is present in both pancreas and in the L-cells of the gut, it is only in the intestines the breakdown products of the "the major proglucagon fragment" resulting in two highly homologous peptides commonly referred as GLP-1 and GLP-2 are observed. These two peptides have important biological activities. As such, the amino acid sequence of GLP-1, which is present in the L-cells, is identical to the 78-107 portion of proglucagon.

The present invention provides novel GLP-1 peptide mimics that duplicate the biological activity of the native peptide and thus are useful for the amelioration of the diabetic condition.

Presently, therapy involving the use of GLP-1-type molecules has presented a significant problem because the serum half-life of such peptides is quite short. For example, GLP-1(7-37) has a serum half-life of only 3 to 5 minutes. Thus there exists a critical need for biologically active GLP-1 mimics that possess extended pharmacodynamic profiles.

SUMMARY OF THE INVENTION

In accordance with the present invention, synthetic isolated polypeptides are provided which have the structure of Formula I

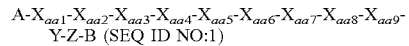

$$A-X_{aa1}-X_{aa2}-X_{aa3}-X_{aa4}-X_{aa5}-X_{aa6}-X_{aa7}-X_{aa8}-X_{aa9}-Y-Z-B \text{ (SEQ ID NO:1)}$$

wherein, $X_{aa1-9}$ is a naturally or nonnaturally occurring amino acid residue;

Y and Z are amino acid residues;

wherein one of the substitutions at the alpha-carbon atoms of Y and Z may each independently be substituted with a primary substituent group selected from the group consisting of hydrogen, alkyl, cycloalkyl, cycloalkylalkyl, heterocyclylalkyl, arylalkyl and heteroarylalkyl, heterocyclylalkyl said primary substituent optionally being substituted with a secondary substituent selected from a cycloalkyl, heterocyclyl, aryl or heteroaryl group; any of said primary or secondary substituents may further be substituted with one or more of, hydrogen, alkyl, cycloalkyl, arylalkyl, aryl, heterocyclyl, heteroaryl, alkenyl, alkynyl, halo, hydroxy, mercapto, nitro, cyano, amino, acylamino, azido, guanidino, amidino, carboxyl, carboxamido, carboxamido alkyl, formyl, acyl, carboxyl alkyl, alkoxy, aryloxy, arylalkyloxy, heteroaryloxy, heterocycleoxy, acyloxy, mercapto, mercapto alkyl, mercaptoaryl, mercapto acyl, halo, cyano, nitro, azido, amino, guanidino alkyl, guanidino acyl, sulfonic, sulfonamido, alkyl sulfonyl, aryl sulfonyl or phosphonic group; wherein, the primary or secondary substitutents may optionally be bridged by covalent bonds to form one or more fused cyclic or heterocyclic systems with each other;

wherein, the other substitution at the alpha-carbon of Y may be substituted with hydrogen, alkyl, aminoalkyl, hydroxyalkyl or carboxyalkyl;

wherein, the other substitution at the alpha-carbon of Z may be substituted with hydrogen, alkyl, aminoalkyl, hydroxyalkyl or carboxyalkyl;

A and B are optionally present;

wherein A is present and A is hydrogen, an amino acid or peptide containing from about 1 to about 15 amino acid residues, an R group, an R—C(O) (amide) group, a carbamate group RO—C(O), a urea $R_4R_5N$—C(O), a sulfonamido R—$SO_2$, or a $R_4R_5N$—$SO_2$;

wherein R is selected from the group consisting of hydrogen, alkyl, cycloalkyl, cycloalkylalkyl, heterocyclyl, heterocycloalkyl, aryl, heteroaryl, arylalkyl, aryloxyalkyl, heteroarylalkyl and heteroaryloxyalkyl;

wherein $R_4$ and $R_5$ are each independently selected from the group consisting of hydrogen, alkyl, cycloalkyl, cycloalkylalkyl, heterocyclyl, heterocycloalkyl, aryl, heteroaryl, arylalkyl, aryloxyalkyl, heteroarylalkyl and heteroaryloxyalky;

wherein the alpha-amino group of $X_{aa1}$ is substituted with a hydrogen or an alkyl group, said alkyl group may optionally form a ring with A;

wherein B is present and B is $OR_1$, $NR_1R_2$, or an amino acid or peptide containing from 1 to 15 amino acid residues, preferably 1 to 10, more preferably 1 to 5 terminating at the C-terminus as a carboxamide, substituted carboxamide, an ester, a free carboxylic acid or an amino-alcohol;

wherein $R_1$ and $R_2$ are independently chosen from hydrogen, alkyl, cycloalkyl, cycloalkylalkyl, heterocyclyl, heterocycloalkyl, aryl, heteroaryl, arylalkyl, aryloxyalkyl, heteroarylalkyl or heteroaryloxyalkyl.

Preferred substitutions upon the alpha-carbon atoms of Y and Z are selected from the group consisting of heteroarylarylmethyl, arylheteroarylmethyl or biphenylmethyl forming biphenylalanine residues, any of which is also optionally substituted with one or more, hydrogen, alkyl, cycloalkyl, arylalkyl, aryl, heterocyclyl, heteroaryl, alkenyl, alkynyl, halo, hydroxy, mercapto, nitro, cyano, amino, acylamino, azido, guanidino, amidino, carboxyl, carboxamido, carboxamido alkyl, formyl, acyl, carboxyl alkyl, alkoxy, aryloxy, arylalkyloxy, heteroaryloxy, heterocycleoxy, acyloxy, mercapto, mercapto alkyl, mercaptoaryl, mercapto acyl, halo, cyano, nitro, azido, amino, guanidino alkyl, guanidino acyl, sulfonic, sulfonamido, alkyl sulfonyl, aryl sulfonyl and phosphonic group.

Further embodiments include isolated polypeptides wherein the other substitution at the alpha-carbon of Y is substituted with hydrogen, methyl or ethyl; and wherein, the other substitution at the alpha-carbon of Z is substituted with hydrogen, methyl or ethyl.

Further embodiments include isolated polypeptides as described above wherein $X_{aa1}$ is naturally or nonnaturally occurring amino acid residue in which one of the substitutions at the alpha-carbon is a primary substituent selected from the group consisting of heterocyclylalkyl, heteroaryl, heteroarylkalkyl and arylalkyl, said primary substituent optionally being substituted with secondary substituent selected from heteroaryl or heterocyclyl; and in which the other substitution at the alpha-carbon is hydrogen or alkyl;

$X_{aa2}$ is naturally or nonnaturally occurring amino acid residue in which one of the substitutions at the alpha-carbon is an alkyl or cycloalkyl where the alkyl group may optionally form a ring with the nitrogen of $X_{aa2}$; and wherein the other substitution at the alpha-carbon is hydrogen or alkyl;

$X_{aa3}$ is a naturally or nonnaturally occurring amino acid residue in which one of the substitutions at the alpha-carbon is selected from the group consisting of a carboxyalkyl, bis-carboxyalkyl, sulfonylalkyl, heteroalkyl and mercaptoalkyl; and wherein the other substitution at the alpha-carbon is hydrogen or alkyl;

$X_{aa4}$ is a naturally or nonnaturally occurring amino acid residue in which the alpha-carbon is not substituted, or in which one of the substitutions at the alpha-carbon is selected from the group consisting of aminoalkyl, carboxyalkyl heteroarylalkyl and heterocycylalkyl;

$X_{aa5}$ is a naturally or nonnaturally occurring amino acid residue in which one of the substitutions at the alpha-carbon is an alkyl or hydroxyalkyl, and in which the other substitution at the alpha-carbon is hydrogen or alkyl;

$X_{aa6}$ is a naturally or nonnaturally occurring amino acid residue in which one of the substitutions at the alpha-carbon is selected from the group consisting of alkyl, aryl, heteroaryl, heterocyclyl, cycloalkylalkyl, heterocyclylalkyl, arylalkyl and heteroarylalkyl group, and wherein the other substitution at the alpha-carbon is hydrogen or alkyl;

$X_{aa7}$ is a naturally or nonnaturally occurring amino acid residue in which one of the substitutions at the alpha-carbon is a hydroxyalkyl group;

$X_{aa8}$ is a naturally or nonnaturally occurring amino acid residue in which one of the substitutions at the alpha-carbon is selected from the group consisting of alkyl, hydroxyalkyl, heteroarylalkyl and carboxamidoalkyl, and in which the other substitution at the alpha-carbon is hydrogen or alkyl;

$X_{aa9}$ is a naturally or nonnaturally occurring amino acid residue in which one of the substitutions at alpha-carbon is selected from the group consisting of carboxyalkyl, bis-carboxyalkyl, carboxylaryl, sulfonylalkyl, carboxylamidoalkyl and heteroarylalkyl; and wherein A is hydrogen, an amino acid or peptide containing from about 1 to about 5 amino acid residues, an R group, an R—C(O) amide group, a carbamate group RO—C(O), a urea $R_4R_5N$—C(O), a sulfonamido R—$SO_2$ or a $R_4R_5N$—$SO_2$.

Preferred are isolated peptides wherein $X_{aa1}$ is an amino acid residue selected from the group consisting of L-His, D-His, L-N-Methyl-His, D-N-Methyl-His, L-4-ThiazolylAla and D-4-ThiazolylAla;

$X_{aa2}$ is an amino acid residue selected from the group consisting of L-Ala, D-Ala, L-Pro, Gly, D-Ser, D-Asn, L-N-Methyl-Ala, D-N-Methyl-Ala, L-4-ThioPro, L-Pro(t-4-OH)(L-4-hydroxyproline), L-2-Pip, L-2-Azt, Aib, S- or R-Iva and $Acc_3$;

$X_{aa3}$ is an amino acid residue selected from the group consisting of L-Glu, L-N-Methyl-Glu, L-Asp, D-Asp, L-His, L-Gla, L-Adp, L-Cys and L-4-ThiazolylAla;

$X_{aa4}$ is an amino acid residue selected from the group consisting of Gly, L-His, L-Lys and L-Asp;

$X_{aa5}$ is an amino acid residue selected from the group consisting of L-Thr, D-Thr, L-Nle, L-Met, L-Nva and L-Aoc;

$X_{aa6}$ is an amino acid residue selected from the group consisting of L-Phe, L-Tyr, L-Tyr(Bzl), Tyr(3-$NO_2$), L-Nle, L-Trp, L-Phe(penta-Fluoro), D-Phe(penta-Fluoro), Phe(2-Fluoro), Phe(3-Fluoro), Phe(4-Fluoro), Phe(2,3-di-Fluoro), Phe(3,4-di-Fluoro), Phe(3,5-di-Fluoro), L-Phe(2,6-di-Fluoro), Phe(3,4,5-tri-Fluoro), Phe(2-Iodo), Phe(2-OH), Phe(2-OMethyl), Phe(3-OMethyl), Phe(3-Cyano), Phe(2-Chloro), Phe(2-$NH_2$), Phe(3-$NH_2$), Phe(4-$NH_2$), Phe(4-

NO$_2$), Phe(4-Methyl), Phe(4-Allyl), Phe(n-butyl), Phe(4-Cyclohexyl), Phe(4-Cyclohexyloxy), Phe(4-Phenyloxy), 2-NaphthylAla, 2-PyridylAla, L-4-ThiazolylAla, L-2-Thi, L-(α-Me-Phe, D-α-Me-Phe, L-α-Et-Phe, D-α-Et-Phe, L-α-Me-Phe(2-Fluoro), D-α-Me-Phe(2-Fluoro), L-α-Me-Phe(2,3-di-Fluoro), D-α-Me-Phe(2,3-di-Fluoro), L-α-Me-Phe(2,6-di-Fluoro), D-α-Me-Phe(2,6-di-Fluoro), L-α-Me-Phe(penta-Fluoro) and D-α-Me-Phe(penta-Fluoro);

$X_{aa7}$ is an amino acid residue selected from the group consisting of L-Thr, D-Thr, L-Ser and L-hSer;

$X_{aa8}$ is an amino acid residue selected from the group consisting of L-Ser, L-hSer, L-His, L-Asn and L-α-Me-Ser; and $X_{aa9}$ is an amino acid residue selected from the group consisting of L-Asp, L-Glu, L-Gla, L-Adp, L-Asn and L-His.

Additional embodiments include those wherein

Y is selected from the group consisting of L-Bip, D-Bip, L-Bip(2-Me), D-Bip(2-Me), L-Bip(2'-Me), L-Bip(2-Et), D-Bip(2-Et), L-Bip(3-Et), L-Bip(4-Et), L-Bip(2-n-Propyl), L-Bip(2-n-Propyl, 4-OMe), L-Bip(2-n-Propyl,2'-Me), L-Bip(3-Me), L-Bip(4-Me), L-Bip(2,3-di-Me), L-Bip(2,4-di-Me), L-Bip(2,6-di-Me), L-Bip(2,4-di-Et), L-Bip(2-Me, 2'-Me), L-Bip(2-Et, 2'-Me), L-Bip(2-Et, 2'-Et), L-Bip(2-Me, 4-OMe), L-Bip(2-Et,4-OMe), D-Bip(2-Et,4-OMe), L-Bip(3-OMe), L-Bip(4-OMe), L-Bip(2,4,6-tri-Me), L-Bip(2,3-di-OMe), L-Bip(2,4-di-OMe), L-Bip(2,5-di-OMe), L-Bip(3,4-di-OMe), L-Bip(2-Et,4,5-di-OMe), L-Bip(3,4-Methylene-di-oxy), L-Bip(2-Et, 4,5-Methylene-di-oxy), L-Bip(2-CH$_2$OH, 4-OMe), L-Bip(2-Ac), L-Bip(3-NH—Ac), L-Bip(4-NH—Ac), L-Bip(2,3-di-Chloro), L-Bip(2,4-di-Chloro), L-Bip(2,5-di-Chloro), L-Bip(3,4-di-Chloro), L-Bip(4-Fluoro), L-Bip(3,4-di-Fluoro), L-Bip(2,5-di-Fluoro), L-Bip(3-n-Propyl), L-Bip(4-n-Propyl), L-Bip(2-iso-Propyl), L-Bip(3-iso-Propyl), L-Bip(4-iso-Propyl), L-Bip(4-tert-Butyl), L-Bip(3-Phenyl), L-Bip(2-Chloro), L-Bip(3-Chloro), L-Bip(2-Fluoro), L-Bip(3-Fluoro), L-Bip(2-CF$_3$), L-Bip(3-CF$_3$), L-Bip(4-CF$_3$), L-Bip(3-NO$_2$), L-Bip(3-OCF$_3$), L-Bip(4-OCF$_3$), L-Bip(2-OEt), L-Bip(3-OEt), L-Bip(4-OEt), L-Bip(4-SMe), L-Bip(2-OH), L-Bip(3-OH), L-Bip(4-OH), L-Bip(2-CH$_2$—COOH), L-Bip(3-CH$_2$—COOH), L-Bip(4-CH$_2$—COOH), L-Bip(2-CH$_2$—NH$_2$), L-Bip(3-CH$_2$—NH$_2$), L-Bip(4-CH$_2$—NH$_2$), L-Bip(2-CH$_2$—OH), L-Bip(3-CH$_2$—OH), L-Bip(4-CH$_2$—OH), L-Phe[4-(1-propargyl)], L-Phe[4-(1-propenyl)], L-Phe[4-n-Butyl], L-Phe[4-Cyclohexyl], Phe(4-Phenyloxy), L-Phe(penta-Fluoro), L-2-(9,10-Dihydrophenanthrenyl)-Ala, 4-(2-Benzo(b)furan)-Phe, 4-(4-Dibenzofuran)-Phe, 4-(4-Phenoxathiin)-Phe, 4-(2-Benzo(b)thiophene)-Phe, 4-(3-thiophene)-Phe, 4-(3-Quinoline)-Phe, 4-(2-Naphthyl)-Phe, 4-(1-Naphthyl)-Phe, 4-(4-(3,5-dimethylisoxazole))-Phe, 4-(2,4-dimethoxypyrimidine)-Phe, homoPhe, Tyr(Bzl), Phe(3,4-di-Chloro), Phe(4-Iodo), 2-Naphthyl-Ala, L-α-Me-Bip and D-α-Me-Bip;

Z is selected from the group consisting of L-Bip, D-Bip, L-Bip(2-Me), D-Bip(2-Me), L-Bip(2'-Me), L-Bip(2-Et), D-Bip(2-Et), L-Bip(3-Me), L-Bip(4-Me), L-Bip(3-OMe), L-Bip(4-OMe), L-Bip(4-Et), L-Bip(2-n-Propyl,2'-Me), L-Bip(2,4-di-Me), L-Bip(2-Me, 2'-Me), L-Bip(2-Me,4-OMe), L-Bip(2-Et,4-OMe), D-Bip(2-Et,4-OMe), L-Bip(2,6-di-Me), L-Bip(2,4,6-tri-Me), L-Bip(2,3,4,5,-tetra-Me), L-Bip(3,4-di-OMe), L-Bip(2,5-di-OMe), L-Bip(3,4-Methylene-di-oxy), L-Bip(3-NH—Ac), L-Bip(2-iso-Propyl), L-Bip(4-iso-Propyl), L-Bip(2-Phenyl), L-Bip(4-Phenyl), L-Bip(2-Fluoro), L-Bip(4-CF$_3$), L-Bip(4-OCF$_3$), L-Bip(2-OEt), L-Bip(4-OEt), L-Bip(4-SMe), L-Bip(2-CH$_2$—COOH), D-Bip(2-CH$_2$—COOH), L-Bip(2'-CH$_2$—COOH), L-Bip(3-CH$_2$—COOH), L-Bip(4-CH$_2$—COOH), L-Bip(2-CH$_2$—NH$_2$), L-Bip(3-CH$_2$—NH$_2$), L-Bip(4-CH$_2$—NH$_2$), L-Bip(2-CH$_2$—OH), L-Bip(3-CH$_2$—OH), L-Bip(4-CH$_2$—OH), L-Phe(3-Phenyl), L-Phe[4-n-Butyl], L-Phe[4-Cyclohexyl], Phe(4-Phenyloxy), L-Phe(penta-Fluoro), L-2-(9,10-Dihydrophenanthrenyl)-Ala, 4-(3-Pyridyl)-Phe, 4-(2-Naphthyl)-Phe, 4-(1-Naphthyl)-Phe, 2-Naphthyl-Ala, 2-Fluorenyl-Ala, L-α-Me-Bip, D-α-Me-Bip, L-Phe(4-NO$_2$) and L-Phe(4-Iodo);

A is selected from the group consisting of H, Acetyl, β-Ala, Ahx, Gly, Asp, Glu, Phe, Lys, Nva, Asn, Arg, Ser, Thr, Val, Trp, Tyr, Caprolactam, L-Bip, L-Ser(Bzl), 3-PyridylAla, Phe(4-Me), Phe(penta-Fluoro), 4-Methylbenzyl, 4-Fluorobenzyl, n-propyl, n-hexyl, cyclohexylmethyl, 6-hydroxypentyl, 2-Thienylmethyl, 3-Thienylmethyl, penta-Fluorobenzyl, 2-naphthylmethyl, 4-biphenylmethyl, 9-Anthracenylmethyl, benzyl, (S)-(2-amino-3-phenyl)propyl, methyl, 2-aminoethyl and (S)-2-Aminopropyl; and B is selected from the group consisting of OH, NH$_2$, Trp-NH$_2$, 2-NaphthylAla-NH$_2$, Phe(penta-Fluoro)-NH$_2$, Ser(Bzl)-NH$_2$, Phe(4-NO$_2$)—NH$_2$, 3-PyridylAla-NH$_2$, Nva-NH$_2$, Lys-NH$_2$, Asp-NH$_2$, Ser-NH$_2$, His-NH$_2$, Tyr-NH$_2$, Phe-NH$_2$, L-Bip-NH$_2$, D-Ser-NH$_2$, Gly-OH, β-Ala-OH, GABA-OH and APA-OH.

When A is not present, and $X_{aa1}$ is an R group, an R—C(O) (amide) group, a carbamate group RO—C(O), a urea R$_4$R$_5$N—C(O), a sulfonamido R—SO$_2$, or a R$_4$R$_5$N—SO$_2$; wherein R is selected from the group consisting of hydrogen, alkyl, cycloalkyl, cycloalkylalkyl, heterocyclyl, heterocycloalkyl, aryl, heteroaryl, arylalkyl, aryloxyalkyl, heteroarylalkyl, heteroaryloxyalkyl and heteroarylalkoxyalkyl; and wherein R$_4$ and R$_5$ are each independently selected from the group consisting of hydrogen, alkyl, cycloalkyl, cycloalkylalkyl, heterocyclyl, heterocycloalkyl, aryl, heteroaryl, arylalkyl, aryloxyalkyl, heteroarylalkyl and heteroaryloxyalky.

When B is not present and Z is OR$_1$, NR$_1$R$_2$ or an amino-alcohol; wherein

R$_1$ and R$_2$ are independently chosen from hydrogen, alkyl, cycloalkyl, cycloalkylalkyl, heterocycle, heterocycloalkyl, aryl, heteroaryl, arylalkyl, aryloxyalkyl, heteroarylalkyl or heteroaryloxyalkyl.

Preferred are isolated polypeptides wherein $X_{aa1}$ (where applicable), $X_{aa2}$ and $X_{aa3}$ are N—H or N-alkylated, preferably N-methylated amino acid residues.

Preferably the isolated polypeptide is a 10-mer to 15-mer and such polypeptide and binds to and activates the GLP-1 receptor.

The present invention also provides a method of making a polypeptide that mimics the activity of a polypeptide receptor agonist.

In accordance with the present invention, the synthetic isolated peptides described herein possess the ability to mimic the biological activity of GLP peptides, with preference for mimicking GLP-1. These synthetic peptide GLP-1 mimics exhibit desirable in-vivo properties, thus making them ideal therapeutic candidates for oral or parenteral administration.

The present invention also provides an isolated polypeptide according to Formula 1, wherein the polypeptide is a Glucagon-Like-Peptide derivative, preferably a Glucagon-Like-Peptide-1 derivative.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes and related diseases as defined above and hereinafter, wherein a therapeutically effective amount of a combination of a compound of formula I and at least one other type of therapeutic agent, such as an antidiabetic agent, a hypolipidemic agent or anti-obesity agent, is administered to a human patient in need of treatment.

DETAILED DESCRIPTION OF THE INVENTION

Figure 1:
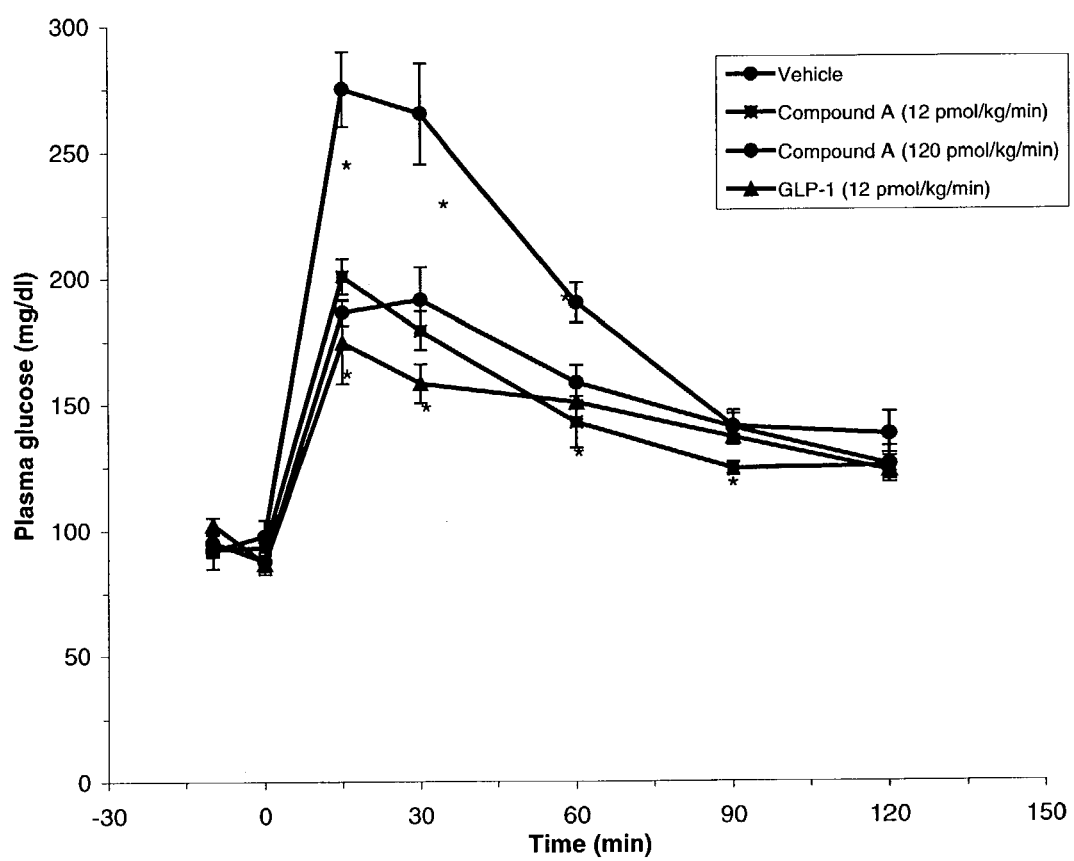
FIG. 1 illustrates the effects of intravenous infusion of Compound A and GLP-1 on plasma glucose in scGTT in rats.

The following definitions apply to the terms as used throughout this specification, unless otherwise limited in specific instances.

Unless otherwise indicated, the term "amino-alcohol" as employed herein alone or as part of another group includes a natural or un-natural amino acid in which the carboxy group is replaced (reduced) to a methyl alcohol such as valinol, glycinol, alaninol, arylalaninol, heteroarylalaninol.

Unless otherwise indicated, the term "alkyl" as employed herein alone or as part of another group includes both straight and branched chain hydrocarbons, containing 1 to 40 carbons, preferably 1 to 20 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, alkynyl, hydroxy, arylalkyl, cycloalkyl, cycloalkylalkyl, alkoxy, arylalkyloxy, heteroaryloxy, heteroarylalkyloxy, alkanoyl, halo, hydroxyl, thio, nitro, cyano, carboxyl, carbonyl (=), carboxamido, amino, alkylamino, dialkylamino, amido, alkylamino, arylamido, heterarylamido, azido, guanidino, amidino, phosphonic, phosphinic, sulfonic, sulfonamido, haloaryl, $CF_3$, $OCF_2$, $OCF_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "alkenyl" as employed herein alone or as part of another group includes both straight and branched chain hydrocarbons, containing 2 to 40 carbons with one or more double bonds, preferably 2 to 20 carbons with one to three double bonds, more preferably 2 to 8 carbons with one to two double bonds, in the normal chain, such that any carbon may be optionally substituted as described above for "alkyl".

Unless otherwise indicated, the term "alkynyl" as employed herein alone or as part of another group includes both straight and branched chain hydrocarbons, containing 2 to 40 carbons with one or more triple bonds, preferably 2 to 20 carbons with one to three triple bonds, more preferably 2 to 8 carbons with one to two triple bonds, in the normal chain, such that any carbon may be optionally substituted as described above for "alkyl".

Unless otherwise indicated, the term "cycloalkyl" as employed herein alone or as part of another group includes saturated or partially unsaturated (containing 1 or 2 double bonds) cyclic hydrocarbon groups containing 1 to 3 rings, appended or fused, including monocyclic alkyl, bicyclic alkyl and tricyclic alkyl, containing a total of 3 to 20 carbons forming the rings, preferably 4 to 7 carbons, forming each ring; which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

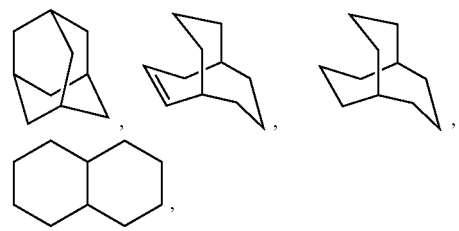

any of which groups may be optionally substituted through any available carbon atoms with 1 or more groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, carboxyl, carbonyl

carboxamido, amino, substituted amino wherein the amino includes 1 or 2 substituents (which are alkyl, aryl or any of the other aryl compounds mentioned in the definitions), amido, azido, guanidino, amidino, phosphonic, phosphinic, sulfonic, sulfonamido, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or heterocycloalkyl rings) and may be optionally substituted through any available carbon atoms with 1 or more groups selected from hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, hetroarylalkyloxy, hetroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalkylaminocarbonyl, arylaminocarbonyl, heteroarylaminocarbonyl, heteroarylalkylaminocarbonyl alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "arylalkyl" as used herein alone or as part of another group refers to alkyl groups as defined above having an aryl substituent, such as benzyl, phenethyl or naphthylpropyl, wherein said aryl and/or alkyl groups may optionally be substituted as defined above.

The term "alkoxyl", "aryloxyl", "heteroaryloxy" "arylalkyloxy", or "heteroarylalkyloxy" as employed herein alone or as part of another group includes an alkyl or aryl group as defined above linked through an oxygen atom.

The term "heterocyclo", "heterocycle" "heterocyclyl" or "heterocyclic", as used herein, represents an unsubstituted or substituted stable 4-, 5-, 6- or 7-membered monocyclic ring system which may be saturated or unsaturated, and which consists of carbon atoms and from one to four heteroatoms selected from nitrogen, sulfur, oxygen and/or a SO or SO$_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, tetrahydrofuranyl, tetrahydrothiophenyl pyrrolidinyl, piperidinyl, piperazinyl, oxopyrrolidinyl, oxopiperazinyl, oxopiperidinyl and oxadiazolyl. Optionally a heterocyclo group may be substituted with one or more functional groups, such as those described for "alkyl" or "aryl".

The term "heterocycloalkyl" as used herein alone or as part of another group refers to alkyl groups as defined above having a heterocycloalkyl substituent, wherein said "heterocyclo" and/or alkyl groups may optionally be substituted as defined above.

The term "heteroaryl" as used herein refers to a 5-, 6- or 7-membered aromatic heterocyclic ring which contains one or more heteroatoms selected from nitrogen, sulfur, oxygen and/or a SO or SO$_2$ group. Such rings may be fused to another aryl or heteroaryl ring and include possible N-oxides; Examples of such heteroaryl groups include, but are not limited to, furan, pyrrole, thiophene, pyridine, isoxazole, oxazole, imidazole and the like. Optionally a heteroaryl group may be substituted with one or more functional groups commonly attached to such chains, such as those described for "alkyl" or "aryl".

The term "heteroarylalkyl" as used herein alone or as part of another group refers to alkyl groups as defined above having a heteroaryl substituent, wherein said heteroaryl and/or alkyl groups may optionally be substituted as defined above.

The term "diabetes and related diseases or related conditions" refers to Type II diabetes, Type I diabetes, impaired glucose tolerance, obesity, hyperglycemia, Syndrome X, dysmetabolic syndrome, diabetic complications, and hyperinsulinemia.

The term "lipid-modulating" or "lipid lowering" agent as employed herein refers to agents that lower LDL and/or raise HDL and/or lower triglycerides and/or lower total cholesterol and/or other known mechanisms for therapeutically treating lipid disorders.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The peptides and analogs thereof described herein may be produced by chemical synthesis using various solid-phase techniques such as those described in G. Barany and R. B. Merrifield, "The Peptides: Analysis, Synthesis, Biology"; Volume 2—"Special Methods in Peptide Synthesis, Part A", pp. 3-284, E. Gross and J. Meienhofer, Eds., Academic Press, New York, 1980; and in J. M. Stewart and J. D. Young, "Solid-Phase Peptide Synthesis", 2$^{nd}$ Ed., Pierce Chemical Co., Rockford, Ill., 1984. The preferred strategy for use in this invention is based on the Fmoc (9-Fluorenylmethylmethyloxycarbonyl) group for temporary protection of the α-amino group, in combination with the tert-butyl group for temporary protection of the amino acid side chains (see for example E. Atherton and R. C. Sheppard, "The Fluorenylmethoxycarbonyl Amino Protecting Group", in "The Peptides: Analysis, Synthesis, Biology"; Volume 9—"Special Methods in Peptide Synthesis, Part C", pp. 1-38, S. Undenfriend and J. Meienhofer, Eds., Academic Press, San Diego, 1987.

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively. Alternatively, in cases where a C-terminal amino alcohol is present, the C-terminal residue may be attached to 2-Methoxy-4-alkoxybenzyl alcohol resin (SASRIN™, Bachem Bioscience, Inc., King of Prussia, Pa.) as described herein and, after completion of the peptide sequence assembly, the resulting peptide alcohol is released with $LiBH_4$ in THF (see J. M. Stewart and J. D. Young, supra, p. 92).

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.). Preferred for use in this invention are 4-(2', 4'-dimethoxyphenyl-Fmoc-aminomethyl)-phenoxyacetyl-p-methyl benzhydrylamine resin (Rink amide MBHA resin) or p-benzyloxybenzyl alcohol resin (HMP resin) to which the C-terminal amino acid may or may not be already attached. If the C-terminal amino acid is not attached, its attachment may be achieved by DMAP-catalyzed esterification with the O-acylisourea or the HOAT active ester of the Fmoc-protected amino acid formed by its reaction with DIC or DIC/HOAT, respectively. Coupling of the subsequent amino acids can be accomplished using HOBT or HOAT active esters produced from DIC/HOBT or DIC/HOAT, respectively.

The syntheses of the 11-mer peptide analogs described herein can be carried out by using a peptide synthesizer, such as an Advanced Chemtech Multiple Peptide Synthesizer (MPS396) or an Applied Biosystems Inc. peptide synthesizer (ABI 433A). If the MPS396 was used, up to 96 peptides were simultaneously synthesized. If the ABI 433A synthesizer was used, individual peptides were synthesized sequentially. In both cases the stepwise solid phase peptide synthesis was carried out utilizing the Fmoc/t-butyl protection strategy described herein. The non-natural non-commercial amino acids present at position 11 and at position 10 were incorporated into the peptide chain in one of two methods. In the first approach a Boc- or Fmoc-protected non-natural amino acid was prepared in solution using appropriate organic synthetic procedures. The resulting derivative was then used in the step-wise synthesis of the peptide. Alternatively the required nonnatural amino acid was built on the resin directly using synthetic organic chemistry procedures. When a nonnatural non-commercial amino acid was needed for incorporation at position $X_{aa6}$ or at any other $X_{aa}$ position as needed, the required Fmoc-protected nonnatural amino acid was synthesized in solution. Such a derivative was then used in stepwise solid phase peptide synthesis.

Preferred for use in this invention are the Fmoc amino acids derivatives shown below.

Orthogonally Protected Amino Acids Used in Solid Phase Synthesis

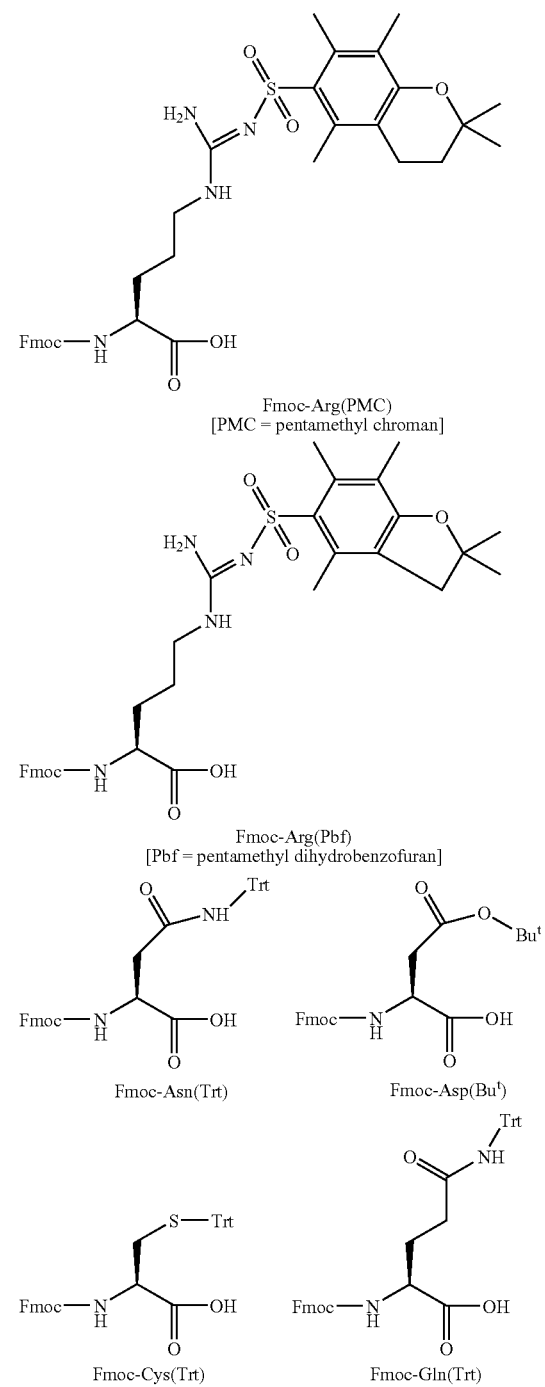

-continued
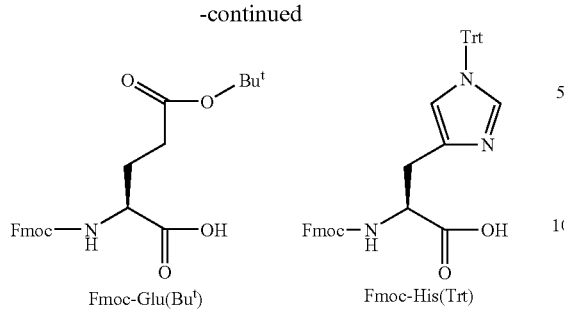
Fmoc-Glu(Bu^t)          Fmoc-His(Trt)
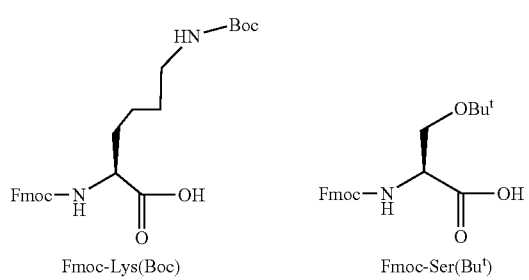
Fmoc-Lys(Boc)           Fmoc-Ser(Bu^t)
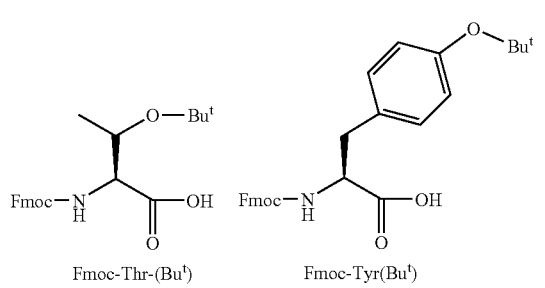
Fmoc-Thr-(Bu^t)         Fmoc-Tyr(Bu^t)
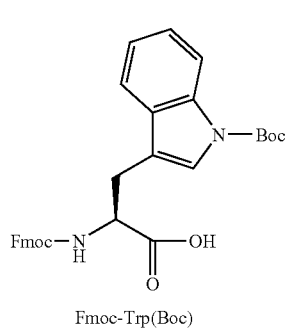
Fmoc-Trp(Boc)
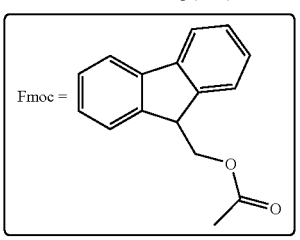
Protected Amino Acid Used in Solid Phase Synthesis
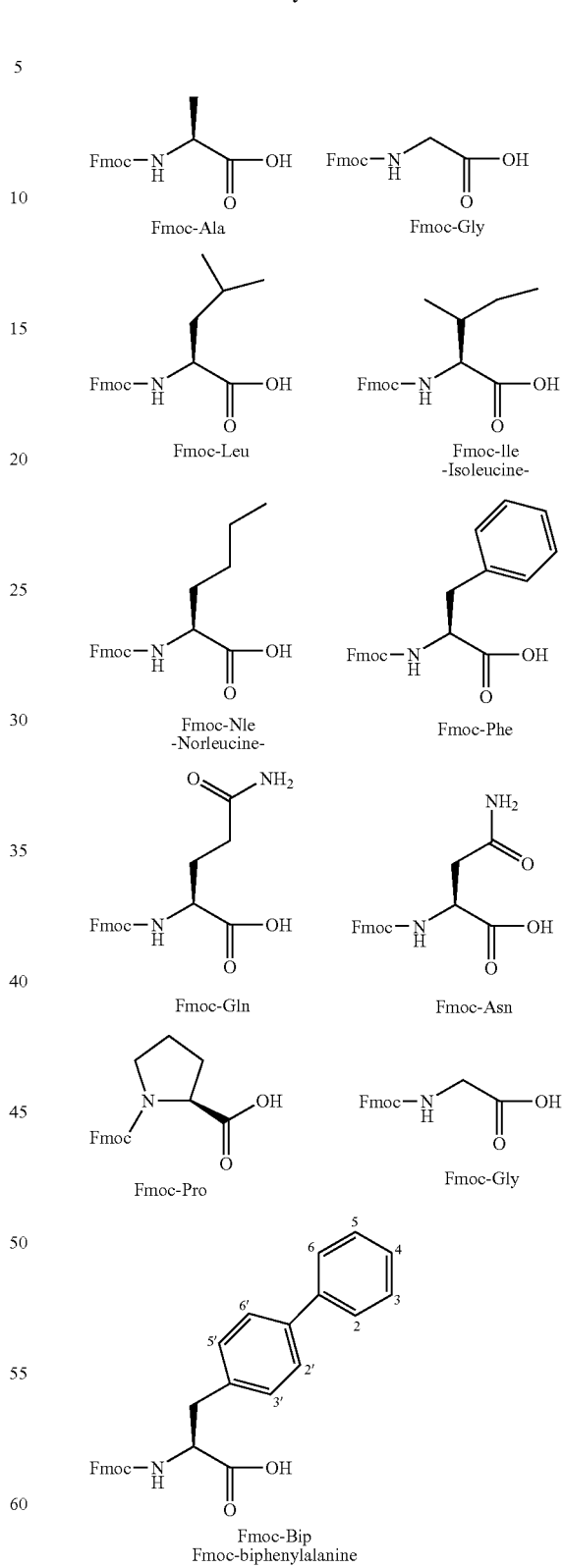
The peptidyl-resin precursors for their respective peptides may be cleaved and deprotected using any of the standard procedures described in the literature (see, for example, D.

S. King et al. Int. J. Peptide Protein Res. 36, 1990, 255-266). A preferred method for use in this invention is the use of TFA in the presence of water and TIS as scavengers. Typically, the peptidyl-resin is stirred in TFA/water/TIS (94:3:3, v:v:v; 1 mL/100 mg of peptidyl resin) for 1.5-2 hrs at room temperature. The spent resin is then filtered off and the TFA solution is concentrated or dried under reduced pressure. The resulting crude peptide is either precipitated and washed with $Et_2O$ or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

The following abbreviations are employed in the Examples and elsewhere herein:

| | |
|---|---|
| Ph = | phenyl |
| Bn = | benzyl |
| i-Bu = | iso-butyl |
| Me = | methyl |
| Et = | ethyl |
| Pr = | n-propyl |
| Bu = | n-butyl |
| TMS = | trimethylsilyl |
| TIS = | Triisopropylsilane |
| $Et_2O$ = | diethyl ether |
| HOAc or AcOH = | acetic acid |
| MeCN = | acetonitrile |
| DMF = | N,N-dimethylformamide |
| EtOAc = | ethyl acetate |
| THF = | tetrahydrofuran |
| TFA = | trifluoroacetic acid |
| $Et_2NH$ = | diethylamine |
| NMM = | N-methyl morpholine |
| NMP = | N-methylpyrrolidone |
| DCM = | dichloromethane |
| n-BuLi = | n-butyllithium |
| Pd/C = | palladium on carbon |
| $PtO_2$ = | platinum oxide |
| TEA = | triethylamine |
| min = | minute(s) |
| h or hr = | hour(s) |
| L = | liter |
| mL = | milliliter |
| µL = | microliter |
| g = | gram(s) |
| mg = | milligram(s) |
| mol = | mole(s) |
| mmol = | millimole(s) |
| meq = | milliequivalent |
| rt = | room temperature |
| sat or sat'd = | saturated |
| aq. = | aqueous |
| mp = | melting point |
| Bip = | biphenylalanine |
| $LiBH_4$ = | lithium borohydride |
| PyBOP reagent = | benzotriazol-1-yloxy-tripyrrolidino phosphonium hexafluorophosphate |
| DMAP = | 4-(dimethylamino)pyridine |
| EDAC = | 3-ethyl-3'-(dimethylamino)propyl-carbodiimide hydrochloride (or 1-(3-(dimethyl)amino)-propyl])-3-ethylcarbodiimide hydrochloride) |
| FMOC = | fluorenylmethoxycarbonyl |
| Boc or BOC = | tert-butoxycarbonyl |
| Cbz = | carbobenzyloxy or carbobenzoxy or benzyloxycarbonyl |

-continued

| | |
|---|---|
| HOBT or HOBT•$H_2O$ = | 1-hydroxybenzotriazole hydrate |
| HOAT = | 1-hydroxy-7-azabenzotriazole |
| TLC = | thin layer chromatography |
| HPLC = | high performance liquid chromatography |
| LC/MS = | high performance liquid chromatography/mass spectrometry |
| MS or Mass Sec = | mass spectrometry |
| NMR = | nuclear magnetic resonance |

Those skilled in the art of peptide chemistry are aware that amino acid residues occur as both D and L isomers, and that the instant invention contemplates the use of either or a mixture of isomers for amino acid residues incorporated in the synthesis of the peptides described herein.

In one embodiment, the present invention provides a method of making a polypeptide of formula

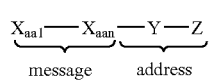

II that mimics the activity of a polypeptide receptor agonist having a message sequence and an address sequence. In this embodiment, the address sequence of the polypeptide confers the ability of a polypeptide to bind to a receptor and the message sequence is capable of inducing receptor mediated signal transduction upon binding of the polypeptide to the receptor. The method of making the polypeptide comprises replacing the message sequence of a polypeptide receptor agonist with Y and Z wherein Y and Z are amino acid residues;

wherein one of the substitutions at the alpha-carbon atoms of Y and Z may each independently be substituted with a primary substituent group selected from the group consisting of hydrogen, alkyl, cycloalkyl, cycloalkylalkyl, heterocyclylalkyl, arylalkyl and heteroarylalkyl, heterocyclylalkyl said primary substituent optionally being substituted with a secondary substituent selected from a cycloalkyl, heterocyclyl, aryl or heteroaryl group; any of said primary or secondary substituents may further be substituted with one or more of, hydrogen, alkyl, cycloalkyl, arylalkyl, aryl, heterocyclyl, heteroaryl, alkenyl, alkynyl, halo, hydroxy, mercapto, nitro, cyano, amino, acylamino, azido, guanidino, amidino, carboxyl, carboxamido, carboxamido alkyl, formyl, acyl, carboxyl alkyl, alkoxy, aryloxy, arylalkyloxy, heteroaryloxy, heterocycleoxy, acyloxy, mercapto, mercapto alkyl, mercaptoaryl, mercapto acyl, halo, cyano, nitro, azido, amino, guanidino alkyl, guanidino acyl, sulfonic, sulfonamido, alkyl sulfonyl, aryl sulfonyl or phosphonic group; wherein, the primary or secondary substitutents may optionally be bridged by covalent bonds to form one or more fused cyclic or heterocyclic systems with each other;

wherein, the other substitution at the alpha-carbon of Y may be substituted with hydrogen, alkyl, aminoalkyl, hydroxyalkyl or carboxyalkyl;

wherein, the other substitution at the alpha-carbon of Z may be substituted with hydrogen, alkyl, aminoalkyl, hydroxyalkyl or carboxyalkyl.

In a preferred embodiment, the present invention provides a method of making a polypeptide that mimics the activity of an endogenous polypeptide receptor agonist. In another preferred embodiment, the polypeptide receptor agonist is GLP-1.

In another aspect, the method of making the polypeptide further comprises replacing the message sequence of the polypeptide with a variant message sequence capable of inducing receptor mediated signal transduction. Variant message sequences can be made by replacing or modifying one or more amino acid residues of a polypeptide receptor agonist message sequence.

EXAMPLE 1

Simultaneous Solid Phase Peptide Synthesis of GLP-1 11-mer Peptide Mimics

Dipeptidyl resin, containing non-natural non-commercial amino acid residues at positions 10 and 11, was prepared using the following manual procedure in a batch-wise mode before continuing peptide chain elongation utilizing the automated simultaneous synthesis protocol on the MPS-396 peptide synthesizer. The synthesis of the Nα-Fmoc-protected biphenylalanine derivatives used in the manual couplings is described in Examples 8-10.

An amount of 4-(2',4'-dimethoxyphenyl-Fmoc-aminomethyl)-phenoxyacetyl-p-methyl benzhydrylamine resin (Rink amide MBHA resin; loading: 0.5 mmol/g) sufficient to synthesize several 11-mer analogs, was swelled by washing with DMF (4×10 mL/g, 5 minutes). The Fmoc group was then removed using two treatments, 3 and 18 minutes each respectively, with 20% piperidine in DMF (10 mL/g). The resin was washed with DMF (4×10 mL/g) and NMP (4×10 mL/g). A 0.5 M solution of Fmoc-L-biphenylalanine-OH (2.0 eq.), or analog thereof, and HOAt (2.0 eq.) in NMP was added to the resin, followed by a 1.0 M solution of DIC (2.05 eq.) in NMP. The resin was then shaken or vortexed for 16-24 hours. Coupling completion was monitored using a qualitative ninhydrin test. The resin was drained, washed with NMP (3×10 mL/g) and DMF (3×10 mL/g), and treated twice, 5 and 20 minutes each respectively, with 20% acetic anhydride in DMF (8 mL/g). After DMF washes (4×10 mL/g), a second manual coupling cycle was then performed as described above, starting from the removal of the Fmoc group with 20% piperidine in DMF, and using either the same or a different Fmoc-protected biphenylalanine analog in the coupling step. This synthesis scheme produced the desired Fmoc-protected dipeptidyl-Rink amide MBHA resin.

Similar dipeptidyl resins were also obtained by another procedure, described in Examples 5-7, using solid phase Suzuki condensation reactions.

Such dipeptidyl-resins required for the synthesis of a set of designed analogs were then used in the automated MPS synthesis of up to 96 peptides per run in the following manner. The dipeptidyl-resins were loaded as suspensions in dichloromethane/DMF (60:40) into the 96-well reactor of an Advanced ChemTech MPS 396 synthesizer in volumes corresponding to 0.01-0.025 mmol (20-50 mg) of resin per reactor well. The reactor was placed on the instrument and drained. The wells were then washed with DMF (0.5-1.0 mL, 3×2 min) and subjected to the number of automated coupling cycles required to assemble the respective peptide sequences as determined by the pre-programmed sequence synthesis table. The detailed stepwise synthesis protocol used for a typical 0.01 mmol/well simultaneous synthesis of 96 compounds is described below. This protocol was adapted for the simultaneous synthesis of arrays of analogs ranging from 12 to 96 per individual run. The general synthesis protocol is depicted in Scheme I.

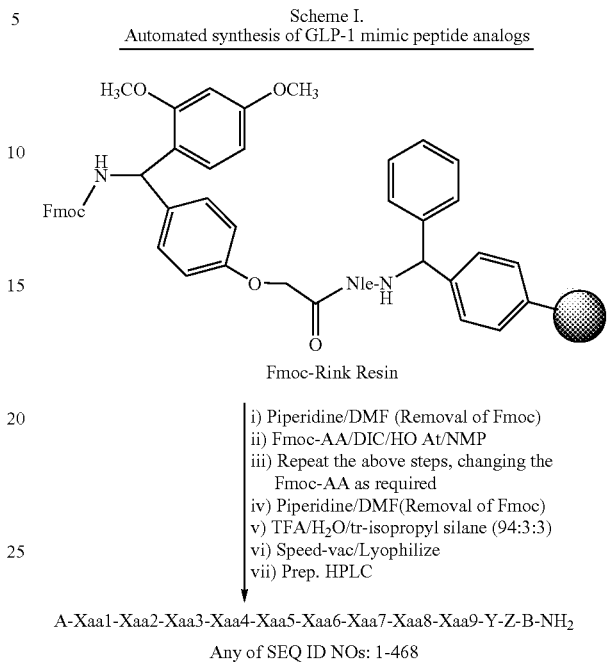

Scheme I.
Automated synthesis of GLP-1 mimic peptide analogs

Fmoc-Rink Resin i) Piperidine/DMF (Removal of Fmoc)
ii) Fmoc-AA/DIC/HO At/NMP
iii) Repeat the above steps, changing the Fmoc-AA as required
iv) Piperidine/DMF(Removal of Fmoc)
v) TFA/H$_2$O/tr-isopropyl silane (94:3:3)
vi) Speed-vac/Lyophilize
vii) Prep. HPLC A-Xaa1-Xaa2-Xaa3-Xaa4-Xaa5-Xaa6-Xaa7-Xaa8-Xaa9-Y-Z-B-NH$_2$ Any of SEQ ID NOs: 1-468

Prior to starting the synthesis, the following reagent solutions were prepared and placed on the instrument as required: 1.5 M (15%) piperidine in DMF; 0.5 M DIEA in NMP; 0.36 M DIC in NMP; 1 M (10%) acetic anhydride in DMF. The required Fmoc-protected amino acids were prepared as 0.36 M solutions in 0.36 M HOAt/NMP and placed into the appropriate positions in the 32-position amino acid rack.

The Fmoc-protected dipeptidyl-resin prepared above was deprotected by treating with 1.5 M (15%) piperidine in DMF (0.6 mL; 1×3 minutes; 1×18 minutes). The resin was then washed with DMF (4×0.5 mL), DMF/EtOH (80:20) (1×0.5 mL) and NMP (3×0.5 mL).

Coupling of the next amino acid residue, typically Fmoc-Asp(OtBu)-OH or another Fmoc-amino acid with appropriate orthogonal protection if required, was carried out by automated addition of a 0.36 M solution of the appropriate Fmoc-amino acid (0.072 mmol, 7.2 eq.) and HOAt (7.2 eq.) in NMP (0.2 mL) to all 96 wells. This was followed by addition to all 96 wells of a 0.36 M solution of DIC (0.072 mmol, 7.2 eq.) in NMP (0.2 mL). The coupling was allowed to proceed for 2 hrs. After reactor draining by nitrogen pressure (3-5 psi) and washing the wells with NMP (1×0.5 mL), the coupling was repeated as described above. At the end of the coupling cycle, the wells were treated with 1M acetic anhydride in DMF (1×0.5 mL, 30 min.) and finally washed with DMF (3×0.5 mL).

The next coupling cycle started with the removal of the Fmoc group as described above, and involved the coupling of either Fmoc-Ser(tBu)-OH or of a different Fmoc-amino acid as required by the sequence substitutions desired at this position. The coupling was carried out in a manner identical to that described for Fmoc-Asp(OtBu)-OH. The next coupling step was carried out in the same way to incorporate either Fmoc-Thr(tBu)-OH or any of the other selected Fmoc-amino acids into this sequence position as required.

The next Fmoc-amino acid (for example Fmoc-Phe-OH) was coupled as described above. For sequences requiring incorporation of a novel non-commercially available aromatic or non-aromatic amino acid analog at this step, the coupling was modified as follows: after Fmoc deprotection in the usual manner, the Fmoc-amino acid (5 eq.) and HOAt (5 eq.) were added manually as a 0.36 M solution in NMP (0.139 mL). The 0.36 M solution of DIC in NMP (0.139 mL) was then added by the instrument and the coupling was allowed to proceed for 16-24 hrs. The coupling was not repeated in this case. After the usual post-coupling washes, the peptidyl-resins were capped with acetic anhydride as described.

The next coupling step involved either Fmoc-Thr(tBu)-OH or substitution analogs as required by sequence replacements at this position. The coupling was performed as described for the initial MPS coupling of Fmoc-Asp(OtBu)-OH and its analogs. This identical coupling protocol was repeated four additional times in order to complete the sequence assembly of the desired 96 11-mer peptide analogs. For the coupling of commercially and non-commercially available non-natural amino acids needed at a certain sequence position, a single coupling protocol similar to that described above for the novel amino acid at position 6 ($X_{aa6}$) was used.

Finally, the Fmoc group was removed with 20% piperidine in DMF as described above, and the peptidyl-resins were washed with DMF (4×0.5 mL) and DCM (4×0.5 mL). They were then dried on the reactor block by applying a constant pressure of nitrogen gas (5 psi) for 10-15 min.

Cleavage/Deprotection

The desired peptides were cleaved/deprotected from their respective peptidyl-resins by treatment with a TFA cleavage mixture as follows. A solution of TFA/water/tri-isopropyl-silane (94:3:3) (1.0 mL) was added to each well in the reactor block, which was then vortexed for 2 hrs. The TFA solutions from the wells were collected by positive pressure into pre-tared vials located in a matching 96-vial block on the bottom of the reactor. The resins in the wells were rinsed twice with an additional 0.5 mL of TFA cocktail and the rinses were combined with the solutions in the vials. These were dried in a SpeedVac™ (Savant) to yield the crude peptides, typically in >100% yields (20-40 mgs). The crude peptides were either washed with ether or more frequently re-dissolved directly in 2 mL of DMSO or 50% aqueous acetic acid for purification by preparative HPLC as follows.

Preparative HPLC Purification of the Crude Peptides

Preparative HPLC was carried out either on a Waters Model 4000 or a Shimadzu Model LC-8A liquid chromatograph. Each solution of crude peptide was injected into a YMC S5 ODS (20×100 mm) column and eluted using a linear gradient of MeCN in water, both buffered with 0.1% TFA. A typical gradient used was from 20% to 70% 0.1% TFA/MeCN in 0.1% TFA/water over 15 min. at a flow rate of 14 mL/min with effluent UV detection at 220 nm. The desired product eluted well separated from impurities, typically after 10-11 min., and was usually collected in a single 10-15 mL fraction on a fraction collector. The desired peptides were obtained as amorphous white powders by lyophilization of their HPLC fractions.

HPLC Analysis of the Purified Peptides

After purification by preparative HPLC as described above, each peptide was analyzed by analytical RP-HPLC on a Shimadzu LC-10AD or LC-10AT analytical HPLC system consisting of: a SCL-10A system controller, a SIL-10A auto-injector, a SPD10AV or SPD-M6A UV/VIS detector, or a SPD-M10A diode array detector. A YMC ODS S3 (4.6×50 mm) column was used and elution was performed using one of the following gradients: 10-70% B in A over 8 min, 2.5 mL/min. (method A); 5-80% B in A over 8 min, 2.5 mL/min. (method B); 5-70% B in A over 8 min., 2.5 mL/min. (method C); 25-75% B in A over 8 min, 2.5 mL/min (method D); 20-75% B in A over 8 min, 2.5 mL/min. (method E); 15-70% B in A over 8 min, 2.5 mL/min. (method F); 10-90% B in A over 8 min, 2.5 mL/min. (method G); 20-65% B in A over 8 min, 2.5 mL/min. (method H); 5-90% B in A over 8 min., 2.0 mL/min. (method I); 5-90% B in A over 8 min, 2.5 mL/min. (method J); 20-80% B in A over 8 min., 2.5 mL/min. (method K); 10-100% B in A over 8 min., 2.5 mL/min. (method L); 10-75% B in A over 8 min., 2.5 mL/min. (method M). Mobile phase A: 0.1% TFA/water; mobile phase B: 0.1% TFA/acetonitrile. The purity was typically >90%.

Characterization by Mass Spectrometry

Each peptide was characterized by electrospray mass spectrometry (ES-MS) either in flow injection or LC/MS mode. Finnigan SSQ7000 single quadrupole mass spectrometers (ThermoFinnigan, San Jose, Calif.) were used in all analyses in positive and negative ion electrospray mode. Full scan data was acquired over the mass range of 300 to 2200 amu for a scan time of 1.0 second. The quadrupole was operated at unit resolution. For flow injection analyses, the mass spectrometer was interfaced to a Waters 616 HPLC pump (Waters Corp., Milford, Mass.) and equipped with an HTS PAL autosampler (CTC Analytics, Zwingen, Switzerland). Samples were injected into a mobile phase containing 50:50 water:acetonitrile with 0.1% ammonium hydroxide. The flow rate for the analyses was 0.42 mL/min. and the injection volume 6 µl. A ThermoSeparations Constametric 3500 liquid chromatograph (ThermoSeparation Products, San Jose, Calif.) and HTS PAL autosampler were used for LC/MS analyses. Chromatographic separations were achieved employing a Luna $C_{18}$, 5 micron column, 2×30 mm (Phenomenex, Torrance, Calif.). The flow rate for the analyses was 1.0 mL/min and column effluent was split, so that the flow into the electrospray interface was 400 µl/min. A linear gradient from 0% to 100% B in A over 4 minutes was run, where mobile phase A was 98:2 water:acetonitrile with 10 mM ammonium acetate and mobile phase B was 10:90 water:acetonitrile with 10 mM ammonium acetate. The UV response was monitored at 220 nm. The samples were dissolved in 200 µl 50:50 $H_2O$:MeCN (0.05% TFA). The injection volume was 5 µl.

In all cases, the experimentally measured molecular weight was within 0.5 Daltons of the calculated monoisotopic molecular weight.

EXAMPLE 2

Synthesis of N-acylated and N-alkylated 11-mer Peptide Analogs

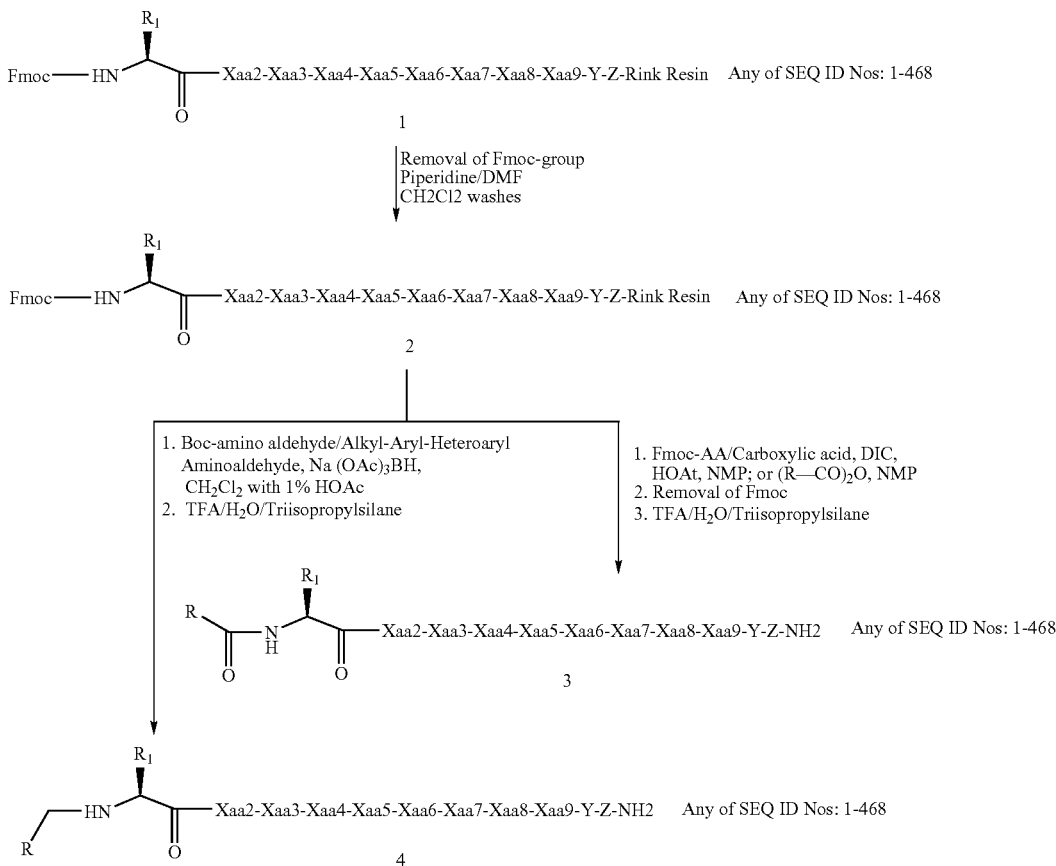

Scheme 2:
Synthesis of Residue #1 substituted/derivatized 11-mer peptide analogs (A) General Procedure for the Synthesis of N-alkylated 11-mer Peptide Analogs by Reductive Alkylation.

The synthesis of N-alkylated 11-mer peptide analogs was started from the protected intermediate 11-mer peptidyl-resin (1) (0.025 mmol), which was prepared by the general method described herein. The Fmoc group was removed using the procedure described in that method, to yield the protected resin intermediate 2. This was swollen in DMF, washed 3 times with 1% AcOH/DMF, and then treated with 2-20 eq. of aldehyde or N-Boc-protected aminoaldehyde (see synthesis below), dissolved in 1% AcOH/DMF (or $CH_2Cl_2$) (1 M), and the same excess amount of Na(AcO)$_3$BH as that of the aldehyde. After overnight reaction, the resin was drained, washed with DMF and DCM, 3 times each, and dried. The reductively alkylated peptide (4) was cleaved and deprotected by treatment with TFA/tri-isopropylsilane/water (90:5:5, v:v:v; 1-2 mL) for 2 hrs. The resin was filtered off and rinsed with 1 mL of cleavage solution, which was combined with the filtrate and dried in a Speed-Vac™ (Savant) to yield the crude product. This was purified by preparative HPLC as described in the general peptide synthesis method outlined herein. The purity and identity of the desired products were confirmed by analytical HPLC and electrospray MS.

N-Boc-protected aminoaldehydes were synthesized using Castro's procedure (Fehrentz, J. A., and Castro, B., *Synthesis*, 1983, 676-678) as follows. The Boc-protected amino acid (2.0 mmol) was dissolved in 5 mL DCM. BOP reagent (1.1 eq.) and DIEA (1.15 eq) were added. After 5 minutes, a solution of N,O-dimethylhydroxylamine (1.2 eq) and DIEA (1.3 eq) in 5 mL DCM was added. The reaction mixture was stirred for 2 hrs, diluted with DCM (30 mL), and washed with 2N HCl (3×), sat. NaHCO$_3$ (3×) and brine (1×). The organic extracts were dried over MgSO$_4$, filtered and evaporated to dryness to yield the Weinreb amide. This was then dissolved in ether or THF (10 mL/mmol)) and reacted with a 1M solution of LiAlH$_4$ in THF (2 mL/mmol of hydroxamate) for 30 minutes. The reaction mixture was quenched with 5 mL of 0.35 M KHSO$_4$, and diluted with ether (20 mL). The aqueous phase was separated and extracted with ether (3×20 mL). The combined ether extracts were washed with 2N HCl (2×), sat. NaHCO$_3$ (2×) and brine (1×), dried over MgSO$_4$, filtered and evaporated to dryness to yield the Boc-protected aldehyde in 20-30% yield. The aldehyde was characterized by $^1$H-NMR and electrospray MS, and was used in the reductive alkylation step without further purification.

(B) General Procedure for the Synthesis of N-acylated 11-mer Peptide Analogs.

Similarly, the synthesis of the N-acylated 11-mer peptide analogs was started from the protected 11-mer peptidyl-resin intermediate (1) (0.025 mmol), prepared as described herein. The Fmoc group was removed using the procedure described herein, and the resulting resin intermediate 2 was coupled with the relevant Fmoc-protected amino acid or carboxylic acid using the coupling protocol described in the general method described herein. In cases where the appropriate anhydride was available, the N-acylation was performed using 10 eq. of the anhydride in NMP. The resulting 12-mer analogs (3) were cleaved/deprotected and purified by prep. HPLC by the general method described herein.

(C) General Procedure for the Synthesis of N-carbamate Derivatives of 11-mer Peptide Analogs.

The synthesis of N-carbamate derivatives of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant chloroformate in the presence of an appropriate base such as a tertiary amine, or with a di-carbonate or an activated carbonate such as p-nitrophenyl or phenyl carbonate. Similarly, N-carbamate derivatives of 10-mer peptide analogs may be prepared starting from a protected 10-mer peptidyl-resin intermediate, Fmoc removal and reaction of the resulting peptidyl-resin intermediate with the relevant chloroformate, di-carbonate or activated carbonate.

(D) General Procedure for the Synthesis, of N-urea Derivatives of 11-mer Peptide Analogs.

The synthesis of N-urea derivatives of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant isocyanate prepared, for example, as in K. Burgess et al., J. Am. Chem. Soc. 1997, 119, 1556-1564; alternatively, the resin intermediate 2 may be allowed to react with the relevant carbamyl chloride. Similarly, N-urea derivatives of 10-mer peptide analogs may be prepared starting from a protected 10-mer peptidyl-resin intermediate, Fmoc removal and reaction of the resulting peptidyl-resin intermediate with the relevant isocyanate or carbamyl chloride.

(E) General Procedure for the Synthesis of N-sulfonamides of 11-mer Peptide Analogs.

The synthesis of N-sulfonamides of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant sulfonyl chloride. Similarly, N-sulfonamides of 10-mer peptide analogs may be prepared starting from a protected 10-mer peptidyl-resin intermediate, Fmoc removal and reaction of the resulting peptidyl-resin intermediate with the relevant sulfonyl chloride.

(F) General Procedure for the Synthesis of N-sulfonylurea Derivatives of 11-mer Peptide Analogs.

The synthesis of N-sulfonylurea derivatives of 11-mer peptide analogs may be started from the protected 11-mer peptidyl-resin intermediate (1) (0.025 mmol), prepared as described herein. The Fmoc group is removed using the procedure described herein, and the resulting resin intermediate 2 is allowed to react with the relevant sulfamoyl chloride $R_4R_5N$—$SO_2$—Cl to yield a sulfonyl urea intermediate (see, for example, P. Davern et al. J. Chem. Soc., Perkin Trans. 2, 1994 (2), 381-387). Similarly, N-sulfonyl urea derivatives of 10-mer peptide analogs may be prepared starting from a protected 10-mer peptidyl-resin intermediate, Fmoc removal and reaction of the resulting peptidyl-resin intermediate with the relevant sulfamoyl chloride $R_4R_5N$—$SO_2$—Cl.

EXAMPLE 3

Synthesis of N-arylalkyl Amides of 10-mer Peptide Analogs

The synthesis of N-arylalkyl amides of 10-mer peptide analogs was started with a reductive alkylation reaction of a relevant arylalkylamine with an alkoxybenzaldehyde resin resin as in the following example. 2-(3,5-Dimethoxy-4-formylphenoxy)ethoxymethyl polystyrene resin (Novabiochem, 1.12 mmol/gram, 0.025 mmol, 27.3 mg) was washed with 1% Acetic Acid in DCM (5×3 mL). A solution of 2-(2-pentafluorophenyl)ethyl amine (0.125 mmol, 26.4 mg) in DCM (3 mL) was added to the resin. After 5 minutes, solid NaBH(OAc)$_3$ (0.125 mmol, 26.5 mg,) was added and the reaction was vortexed for 16 hours. The resin was rinsed with DMF (5×3 mL) and DCM (5×3 mL). A solution of Fmoc-[BIP(2-Et)]-OH (0.05 mmol, 25.3 mg) and HOAt (0.05 mmol, 6.81 mg) in NMP(0.5 mL) was added to the resin followed by DIC (0.05 mmol, 7.82 µL). The reaction was vortexed for 16 hrs. The resin was rinsed with NMP(5×3 mL). The remaining sequence of the desired 10-mer N-arylalkyl amide analog was then assembled as described in Example 1.

EXAMPLE 4

Solid Phase Synthesis of 11-mer Peptide Analogs Using an Applied Biosystems Model 433A Peptide Synthesizer Following is the general description for the solid phase synthesis of typical 11-mer peptide analogs, using an upgraded Applied Biosystems Model 433A peptide synthesizer. The upgraded hardware and software of the synthesizer enabled conductivity monitoring of the Fmoc deprotection step with feedback control of coupling. The protocols allowed a range of synthesis scale from 0.05 to 1.0 mmol.

The incorporation of the two non-natural C-terminal amino acid residues was described earlier in connection with simultaneous synthesis of 11-mer analogs. Such a Fmoc-protected dipeptidyl resin was used in this ABI synthesis. The Fmoc-protected dipeptidyl-resin (0.1 mmol) was placed into a vessel of appropriate size on the instrument, washed 6 times with NMP and deprotected using two treatments with 22% piperidine/NMP (2 and 8 min. each). One or two additional monitored deprotection steps were performed until the conditions of the monitoring option were satisfied (<10% difference between the last two conductivity-based deprotection peaks). The total deprotection time was 10-12 min. The deprotected dipeptidyl-resin was washed 6 times with NMP and then coupled with the next amino acid. The procedure is illustrated by the example used in the next step. Thus, Fmoc-Asp(OtBu)-OH was coupled next using the following method: Fmoc-Asp(OtBu)-OH (1 mmol, 10 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP, and subjected to 8 additional deprotection/coupling cycles as described above in order to complete the assembly of the desired sequence. The Fmoc-amino acids sequentially used were: Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Ala-OH and Fmoc-His(Trt)-OH. Finally, the Fmoc group was removed with 22% piperidine in NMP as described above, and the peptidyl-resin was washed 6 times with NMP and DCM, and dried in vacuo.

Alternatively, a modified coupling protocol was used in which the Fmoc-protected amino acid (1 mmol) was activated by subsequent addition of 0.5 M HOAt in NMP (2 mL) and 1 M DIC/NMP (1 mL), transferred to the reaction vessel and allowed to couple for 1-2 hrs.

Cleavage/Deprotection

The desired peptide was cleaved/deprotected from its respective peptidyl-resin (0.141 g) by treatment with a solution of TFA/water/tri-isopropylsilane (94:3:3) (2.5 mL) for 2 hrs. The resin was filtered off, rinsed with TFA cleavage solution (0.5 mL), and the combined TFA filtrates were dried in vacuo. The resulting solid was triturated and washed with diethyl ether, and finally dried, to yield 35.6 mg (58%) of crude peptide product as a white solid. This was purified by preparative HPLC as described herein. The gradient used was from 20% to 75% 0.1% TFA/MeCN in 0.1% TFA/water over 15 min. The fraction containing a pure product was lyophilized, to yield 7.2 mg (20% recovery) of pure product.

EXAMPLE 5

Synthesis of Biphenylalanine Analogs at Position -10 and Position -11

For those analogs wherein position-10 and position-11 residues were represented by substituted phenylalanine analogs, i.e. biphenylalanine analogs (Bip-analogs), their incorporation into the peptide chain was carried out in one of two approaches.

Approach A: Solid Phase Suzuki Condensation

In approach A, solid phase Suzuki condensation was practiced to prepare the required modified phenylalanine residue in a manner suitable for carrying out subsequent solid phase peptide synthesis to obtain the target peptides. When the amino acid at position-11 in the target peptide was represented by a modified phenylalanine residue, it was prepared as shown in Scheme 3. After removal of the Boc α-amine protecting group, chain elongation was continued using multiple peptide synthesis as described in the previous section to obtain the desired 11-mer peptides or its derivatives thereof. When the modified phenylalanine analog was in position-10 of the target peptides, the required amino acid was prepared using a suitable dipeptide resin as shown in Scheme 4. The resulting dipeptidyl resin containing the required modified phenylalanine derivative was then used to carry out the synthesis of the target 11-mer peptide or its derivatives thereof. When both position-10 and position-11 required novel biphenylalanine residues, two sequential solid phase Suzuki reactions were carried out as shown in Scheme 5.

General Procedure for preparation of resin containing biphenylalanine residue at position-11 (Suzuki couplings).

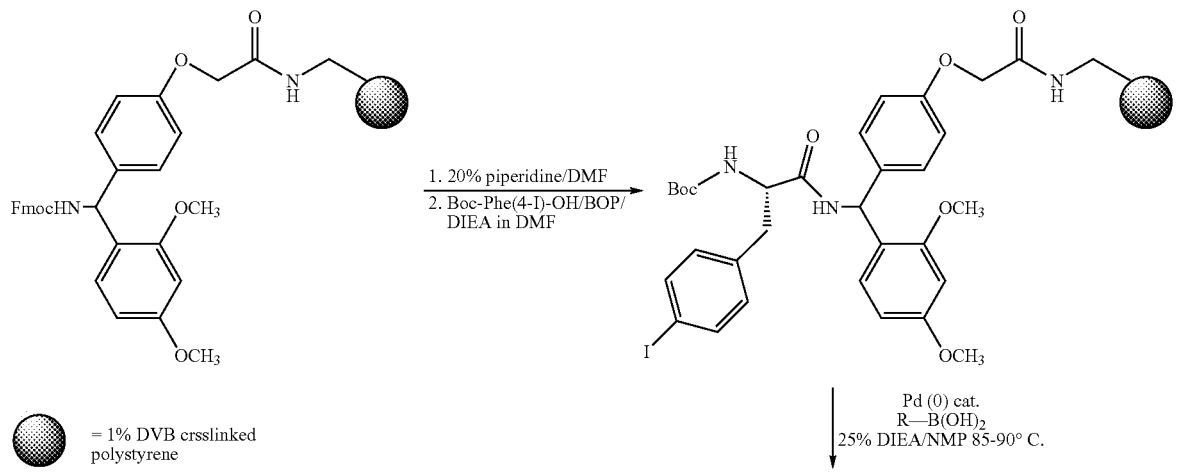

Scheme 3

 = 1% DVB crsslinked polystyrene

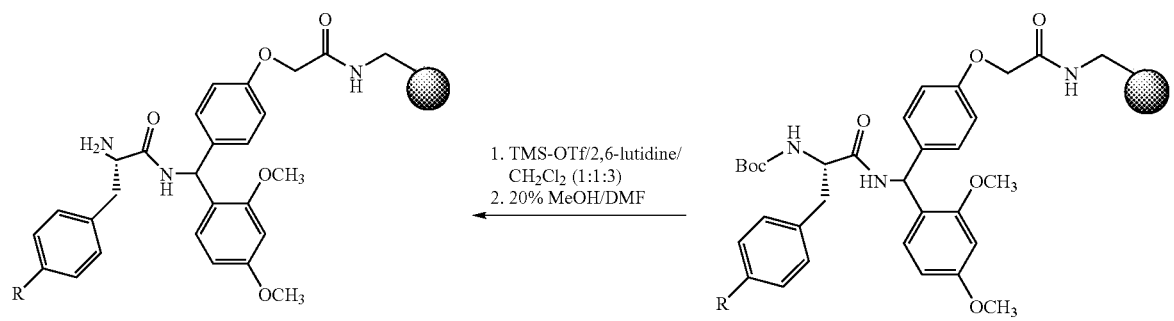

Procedure A:

Polystyrene (1% DVB crosslinked) resins (50 mg, 0.025 mmole) derivatized with an $N^\alpha$-Boc-4-iodophenylalanine residue either attached directly via a Knorr linkage (Boc-amino acid-resin) or via an amino acid-Knorr linkage (Boc-dipeptide-resin) were weighed into 13×100 mm glass culture tubes with screw caps. Aryl-boronic acids (0.5 mmole) were dissolved in 0.75 ml of 25% by volume diisopropylethylamine in N-methylpyrolidinone and added to the resins followed by 0.05 ml of an N-methylpyrolidinone solution containing 1.0 mg of tetrakis(triphenylphospine)palladium (0) catalyst (ca. 3.5 mole %). The resulting mixtures were blanketed with a stream of nitrogen and the reaction vessels tightly capped and maintained at 85-90° C. for 17-20 hours with periodic shaking. The resins were washed with 5×1 ml of N-methylpyrolidinone and 5×1 ml of dichloromethane prior to Boc group cleavage (see General Procedure below).

Procedure B:

The reactions were performed as in General Procedure A except a different catalyst was employed. The catalyst solution was prepared by dissolving 9.0 mg of palladium(II) acetate and 56 mg of 2-(dicyclohexylphosphino)biphenyl in 2.0 ml of N-methylpyrolidinone. For 0.025 mmole scale reactions, 0.038 ml (ca. 3 mole %) of catalyst solution was employed.

Procedures for Cleavage of the Boc Group

Method A: The Boc-protected resins prepared as described in General Procedures A or B were treated with 0.5 ml of reagent solution consisting of trimethylsilyl trifluoromethanesulfonate, 2,6-lutidine and dichloromethane (1:1:3 by volume). After 3 such reagent treatments for 1 hour each with shaking, the resins were washed with 4×1 ml of dichloromethane, 3×1 ml of N,N-dimethylformamide, 3×1 ml of 20% MeOH in N,N-dimethylformamide and 4×1 ml dichloromethane prior to transfer to the automated peptide synthesizer.

Method B: The Boc-protected resins prepared as described in General Procedures A or B were treated with 1.0 ml of 1N HCl in anhydrous 1,4-dioxane for 1 hour at room temperature with shaking. The resins were washed with 4×1 ml of dichloromethane, 3×1 ml of 5% diisopropylethylamine in dichloromethane (vol:vol), 3×1 ml of dichloromethane, and 5×1 ml of N-methylpyrolidinone to provide the free amino-resins ready for the next acylation (coupling reaction) step.

EXAMPLE 6

General Procedure for Preparation of a Resin Containing a Modified Biphenylalanine Residue at Position-10

The general procedures described above (A or B) for Suzuki coupling were utilized to obtain the required dipeptidyl resin containing modified Phe at position-10 starting with the amino acid (at position-11) bound resin as shown in Scheme 4.

Scheme 4
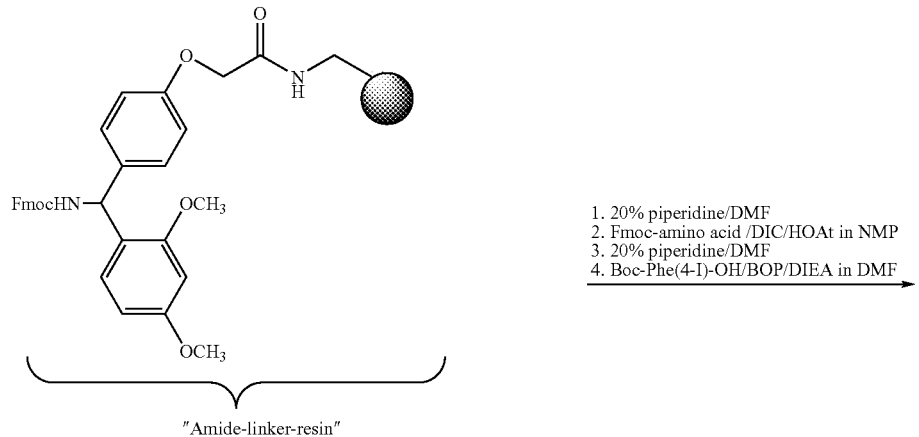
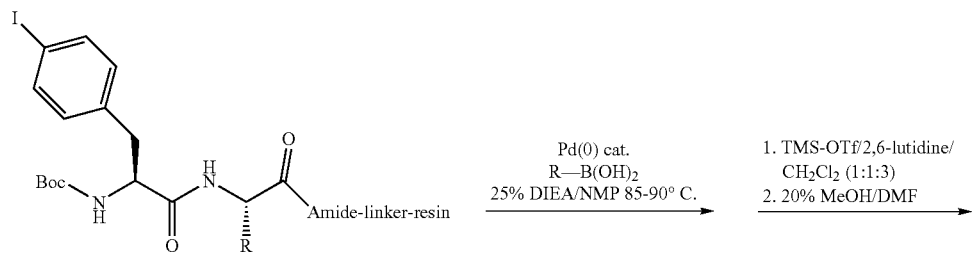
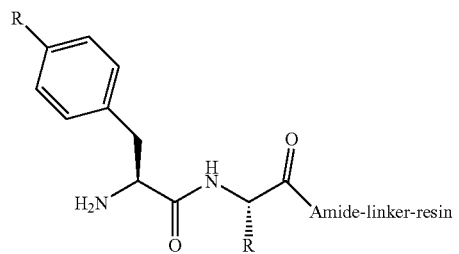

EXAMPLE 7

General Procedure for Preparation of Resin Containing biphenylalanine Residues at Both Positions 10 and 11

Utilizing the procedures described for position 11 modified analogs (Scheme 1) and carrying out the Suzuki coupling procedure two successive times produced dipeptidyl resins containing modified phenylalanine residues at both positions-10 and -11 as illustrated in Scheme 5.

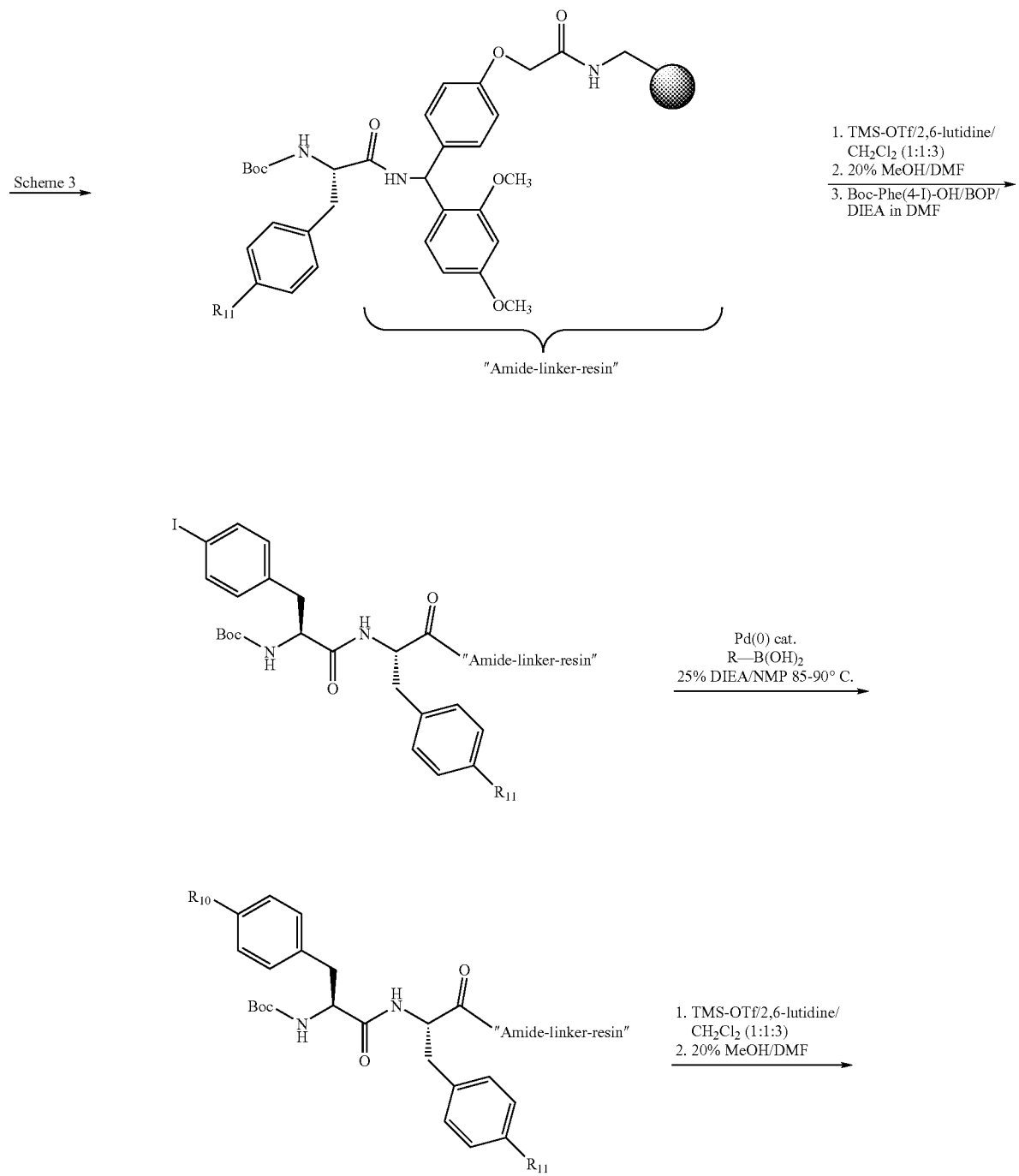

-continued

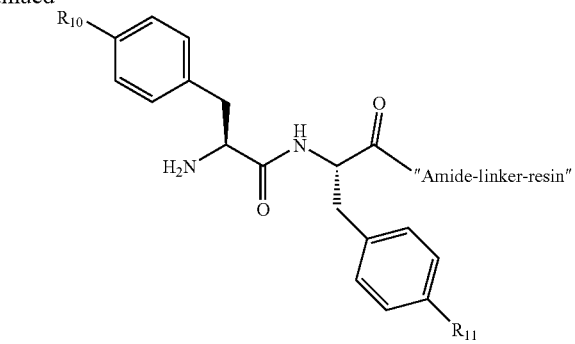

Approach B: Synthesis of Fmoc-biphenylalanine derivatives using Suzuki Condensation in solution.

Using this method, exemplified by the synthesis of Fmoc-2-methyl-biphenylalanine, several N-α-Fmoc protected biphenylalanine derivatives were prepared. They were utilized for the solid phase synthesis of 11-mers and other peptide analogs as described herein.

EXAMPLE 8

Synthesis of Fmoc-2-methyl-biphenylalanine

The following scheme 6 describes the synthesis of Fmoc-2-methyl-biphenylalanine.

Scheme 6

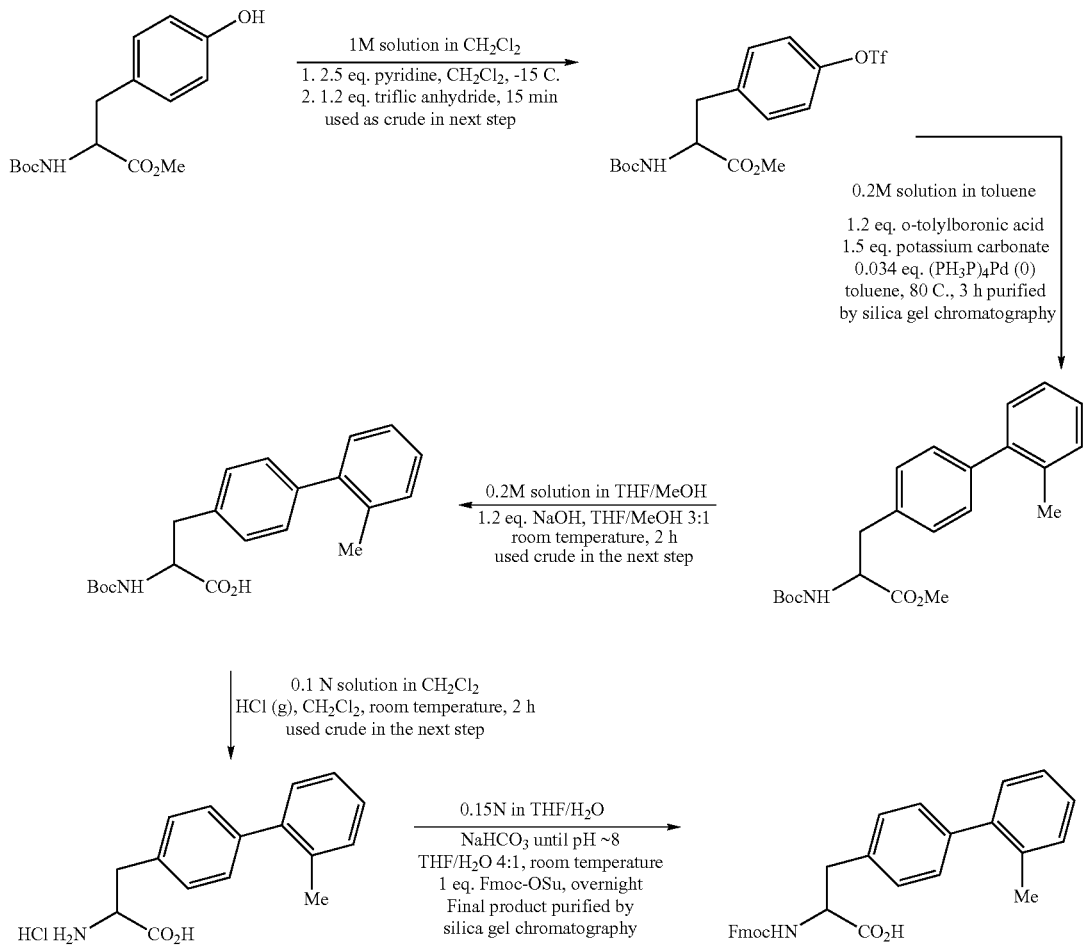

Boc-L-Tyrosine-O-triflate: To a solution of 37 g (126 mmol) of Boc-tyrosine methyl ester, and 25.4 mL (314 mmol, 2.5 eq.) of pyridine in 114 mL of dry dichloromethane, kept at −15° C. under $N_2$, was added slowly 25.4 mL (151 mmol, 1.2 eq.) of triflic anhydride. The solution was stirred at −15° C. for 15 min. HPLC analysis indicated that the reaction was complete. The reaction was quenched by addition of 150 mL of water. The layers were separated, and the organic layer washed with 2×150 mL of 0.5M NaOH, and 2×150 mL of 15% citric acid solution. The organic layer was dried over magnesium sulfate, filtered concentrated and dried in vacuo to give the crude product as a red oil. (Crude yield varied between 90% to quantitative).

Boc-(2-Me) biphenylalanine methyl ester: The above red oil was dissolved in 70 mL of toluene, and added to a degassed suspension containing 19.0 g (140 mmol, 1.2 eq.) of o-tolyllboronic acid, 24.1 g (175 mmol, 1.5 eq.) of potassium carbonate, and 4.6 g (4.0 mol, 0.034 eq.) of tetrakis(triphenylphosphine) palladium (0) in 580 mL of toluene preheated at 80° C. The mixture was heated at 80° C. under $N_2$ for 3 h, cooled to room temperature, and then filtered through celite. The reaction mixture was washed with 2×150 mL of 0.5% of NaOH, and 2×150 mL of 15% citric acid solution, dried over magnesium sulfate and concentrated. The crude mixture thus obtained was purified by silica gel chromatography using ethyl acetate/heptane (1:9) as eluant, [crude mixture was preabsorbed on silica gel (2 g silica gel/g crude mixture), 1:35::mixture:silica gel used for the column], yield varied from 50 to 80%.

Boc-(2-Me) biphenylalanine: To a solution of 44.5 g (120 mmol) of Boc-(2-Me) biphenylalanine methyl ester in 147 mL of methanol and 442 mL of tetrahydrofuran, kept at room temperature, was added 147.4 mL of 1N NaOH (147 mmol, 1.2 eq.). HPLC analysis indicated that the reaction was complete after 1 h. The reaction mixture was concentrated and partitioned between 500 mL of water and 300 mL of ether. The ethereal solution was discarded. Aqueous layer was acidified with 160 mL of 1 N HCl solution, and then extracted with 2×250 mL of ethyl ether. The ethereal solutions were combined, and dried over magnesium sulfate. After filtration, concentration and drying 41.5 g of product was obtained.

Fmoc-(2-Me) biphenylalanine: To a solution of 41.5 g (117 mmol) of Boc-(2-Me) biphenylalanine in 1 L of dichloromethane, kept at room temperature, was bubbled in gaseous HCl. A white solid started to precipitate in approximately 5 min. HPLC taken after 2 hours showed that the reaction was complete. The mixture was concentrated. The residue was redissolved in 600 mL of tetrahydrofuran and 150 mL of water, and solid $NaHCO_3$ was added slowly until the pH of the mixture was basic (a white solid precipitated out), followed by addition of 38.9 g (115 mmol, 1 eq.) of Fmoc-Osu. The mixture was then stirred at room temperature. A homogeneous biphasic solution was obtained within 1 h. The stirring was continued at room temperature under $N_2$ overnight. The layers were separated. The tetrahydrofuran layer was acidified with 58 mL 2N HCl, and then diluted with 400 mL of ethyl acetate. The layers were separated, and the organic layer washed with 2×100 mL of water, dried over magnesium sulfate, and concentrated. The crude product was purified using silica gel column chromatography using dichoromethane as eluant until most of the impurities had been removed. The solvent was then changed to 25% ethyl acetate in heptane containing 1% acetic acid, [approximately 23 g silica gel/g crude mixture used for the column]. The yield was >90% for the three steps.

EXAMPLE 9

General Synthesis of Various Fmoc-biphenylalanine Derivatives

Synthesis of various biphenyl alanine derivatives were carried out using the above described procedure, starting with the commercially available phenol derivative (e.g. Boc-Tyrosine methyl ester) to prepare the triflate and using the appropriate boronic acid to prepare the biphenylalanine analogs. When a required boronic acid was not available from commercial sources the synthesis of this intermediate was carried out as exemplified in the following example.

2-Ethylphenyl boronic acid: To a solution of 25 g (135 mmol) of 1-bromo-2-ethylbenzene in 280 mL of dry tetrahydrofuran, kept at −78° C. in an oven-dried 3 neck flask, was added slowly (keeping the temperature below −68° C.) 67.5 mL of 2.5N n-Butyl lithium in hexanes solution (169 mmol, 1.25 eq.). The reaction was stirred for an additional 1 h, and then 69 mL (405 mmol, 3 eq.) of triethylborate was added slowly, keeping the temperature below −68° C. The reaction was stirred for an additional 40 minutes and then the dry ice bath was removed, the reaction was allowed to warm up to room temperature, and then was poured into 300 mL of ice cold saturated ammonium chloride solution. 200 mL of ice cold ethyl acetate was added, and the mixture stirred for another 30 min. The layers were separated. The organic layer was washed with water, and brine. It was then dried over magnesium sulfate, and concentrated to give 19 g (92% yield) of product. The boronic acid was used without purification in the next step.

EXAMPLE 10

Synthesis of Fmoc-protected Biphenylalanine Analogs with Substitution in the Internal Phenyl Ring Synthesis of the Fmoc-protected biphenylalanine analogs with substitution in the phenyl ring directly attached to the β-carbon (internal ring) of the amino acid moiety was carried as depicted in the following scheme 7.

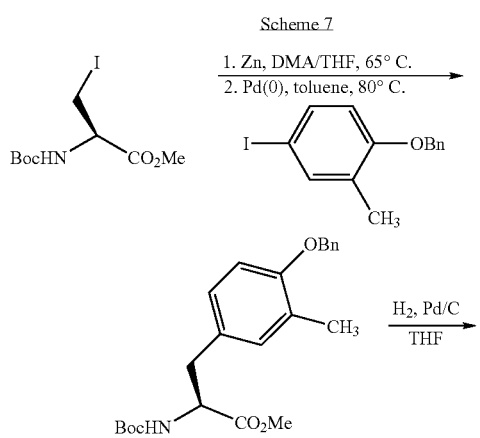

Scheme 7

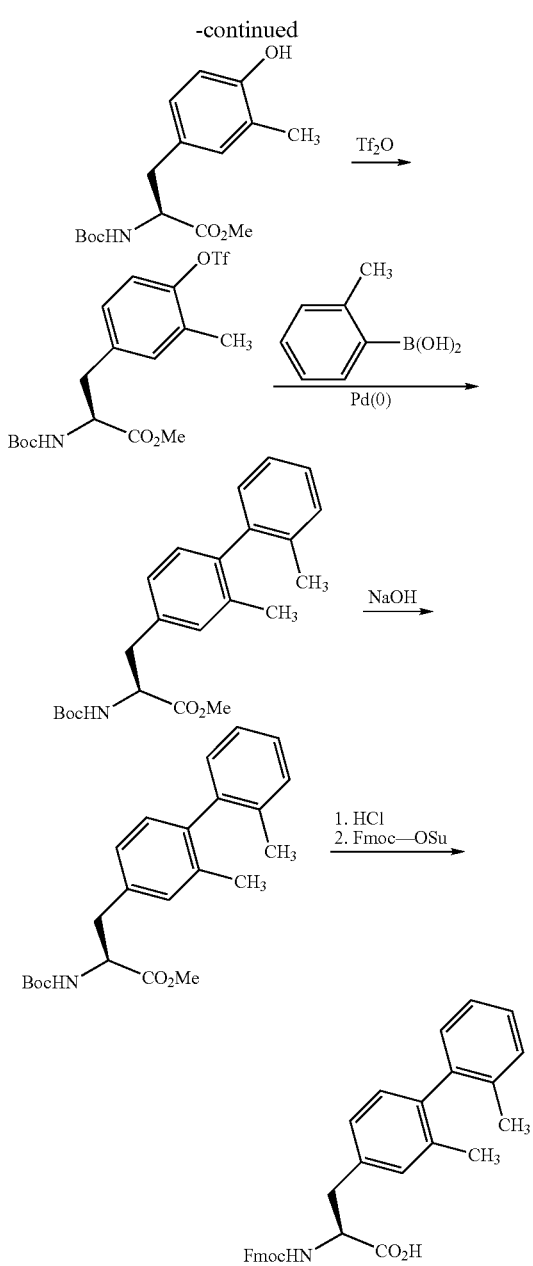

herein, to afford the required Fmoc-protected biphenylalanine analogs with substitution in the phenyl ring directly attached to the β-carbon (internal ring) of the amino acid moiety. Synthesis of a specific example, Fmoc-2'-methyl-2-methyl-biphenylalnine is given below.

Boc-2'-Methyl-Tyrosine benzyl ether methyl ester: 2.2 g (33 mmol) of oven-dried zinc dust was placed in an oven dried flask under nitrogen. 5.2 mL of dry tetrahydrofuran, and 140 µL (1.6 mmol) of 1,2-dibromoethane were added, and the mixture warmed briefly with a heat gun until the solvent began to boil, and then stirred vigorously for a few minutes. This procedure was repeated five times, and then the reaction mixture was cooled to 35° C. 40 µL (0.32 mmol) of chlorotrimethylsilane was added, and the mixture stirred vigorously at 35° C. for 30 min. A solution of 3 mL of 1.04 g (3.17 mmol) of Boc-iodoalanine methyl ester in 1:1 tetrahydrofuran: dimethylacetamide was added slowly, and the reaction mixture stirred at 35° C. for 30 min. A solution of 3 mL of 1:1 tetrahydrofuran:dimethylacetamide containing 819 mg (2.5 mmol) of 4-iodo-2-methyl-1-benzyloxy-benzene was added slowly, followed by 338 mg (1.11 mmol) of tri-o-tolylphosphine, and 288 mg (0.31 mmol) of $Pd_2(dba)_3$. The reaction mixture was degassed, and then stirred at 60° C. for 4 h. The reaction mixture was cooled to room temperature, diluted with ethyl acetate, and filtered through celite. The filtrate was washed with 2×25 mL of 1N HCl, dried over magnesium sulfate, filtered and concentrated. The product was purified by silica gel chromatography (72% yield).

Boc-2'-Methyl-Tyrosine methyl ester: A suspension of 7.5 g (18.7 mmol) of the above compound (Boc-2'-methyl-tyrosine benzyl ether methyl ester) in 30 mL of tetrahydrofuran, and 2.25 g 10% Degussa type 10% palladium on carbon was stirred under hydrogen atmosphere at room temperature and atmospheric presssure for 2 days. The reaction mixture was then filtered through celite, and concentrated. The product was purified by silica gel chromatography (74% yield).

Fmoc-2'-methyl-2-methyl-biphenyl alanine: This compound was prepared using the Suzuki Condensation procedure described herein, using Boc-2'-Methyl-Tyrosine methyl ester as the starting material. The product obtained in the above Suzuki condensation reaction, after removal of the Boc-group and reprotection with Fmoc-group using conditions described herein afforded the desired product.

As a general method, initially a suitably protected tyrosine derivative was prepared by reaction of Boc-β-iodo alanine with the required 4-iodophenol derivative using a zinc mediated condensation. The product from this reaction was subjected to Suzuki condensation reaction as described

EXAMPLE 11

Utilizing the Synthetic Methods Described Herein the Following GLP-1 Mimic Peptides Were Prepared

TABLE I

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| 1. | H | A | E | G | T | F | T | S | D | Bip | Phe(4-NO2) |
| 2. | H | A | E | G | T | F | T | S | D | Bip | 2-Nal |
| 3. | H | A | E | G | T | F | T | S | D | Bip | Bip |
| 4. | H | A | E | G | T | F | T | S | D | Bip | Phe(penta-Fluoro) |
| 5. | H | A | E | G | T | F | T | S | D | Bip | Phe(4-Me) |

TABLE I-continued

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| 6. | H | A | E | G | T | F | T | S | D | 2-Nal | Bip |
| 7. | H | A | E | G | T | F | T | S | D | Bip | F |
| 8. | H | A | E | G | T | F | T | S | D | Bip | Y |
| 9. | H | A | E | G | T | F | T | S | D | 2-Nal | Phe(penta-Fluoro) |
| 10. | H | A | E | G | T | F | T | S | D | Bip | Phe(4-Iodo) |
| 11. | H | A | E | G | T | F | T | S | D | Bip(2-Me) | Bip(4-OMe) |
| 12. | H | A | E | G | T | F | T | S | D | Bip(2-Me) | Bip(3,4-Methylenedioxy) |
| 13. | H | A | E | G | T | F | T | S | D | Bip(2-Me) | 4-(1-Naphthyl)-Phe |
| 14. | H | A | E | G | T | F | T | S | D | Bip(2-Me) | Bip(4-Me) |
| 15. | H | A | E | G | T | F | T | S | D | Bip(2-Me) | Bip(3-Me) |
| 16. | H | A | E | G | T | F | T | S | D | Bip(2,4-di-OMe) | Bip(2-Me) |
| 17. | H | A | E | G | T | F | T | S | D | Bip(2-Me,4-OMe) | Bip(2-Me) |
| 18. | H | A | D | G | T | F | T | S | D | Bip(2-Me) | Bip(2-Me) |
| 19. | H | A | E | G | Nle | F | T | S | D | Bip(2-Me) | Bip(2-Me) |
| 20. | H | A | E | G | T | Phe(penta-Fluoro) | T | S | D | Bip(2-Me) | Bip(2-Me) |
| 21. | H | A | H | G | T | Phe(penta-Fluoro) | T | S | D | Bip(2-Me) | Bip(2-Me) |
| 22. | H | A | D | G | Nle | F | T | S | D | Bip(2-Me) | Bip(2-Me) |
| 23. | H | A | E | G | Nle | Phe(penta-Fluoro) | T | S | D | Bip(2-Me) | Bip(2-Me) |
| 24. | H | A | E | G | Nle | F | T | H | D | Bip(2-Me) | Bip(2-Me) |
| 25. | H | ala | D | G | Nle | F | T | S | D | Bip(2-Me) | Bip(2-Me) |
| 26. | H | ala | D | G | T | Phe(penta-Fluoro) | T | S | D | Bip(2-Me) | Bip(2-Me) |
| 27. | H | A | H | G | Nle | Phe(penta-Fluoro) | T | S | D | Bip(2-Me) | Bip(2-Me) |
| 28. | H | A | H | G | T | Phe(penta-Fluoro) | T | H | D | Bip(2-Me) | Bip(2-Me) |
| 29. | H | A | D | G | T | Phe(penta-Fluoro) | T | H | D | Bip(2-Me) | Bip(2-Me) |
| 30. | H | A | D | G | Nle | F | T | H | D | Bip(2-Me) | Bip(2-Me) |
| 31. | H | ala | D | G | Nle | Phe(penta-Fluoro) | T | S | D | Bip(2-Me) | Bip(2-Me) |
| 32. | H | A | E | G | T | F | T | S | D | Bip(2-Et) | Bip |
| 33. | H | A | E | G | Nle | Phe(penta-Fluoro) | T | H | D | Bip(2-Me) | Bip(2-Me) |
| 34. | H | A | E | G | T | F | T | S | D | Bip(2-OEt) | Bip(2-Me) |
| 35. | H | A | E | G | T | F | T | S | D | Bip(2-Propyl) | Bip(2-Me) |
| 36. | H | A | E | G | T | F | T | S | D | Bip(2-Propyl,4-OMe) | Bip(2-Me) |
| 37. | H | A | E | G | T | F | T | S | D | Bip(2-Trifluoromethyl) | Bip |
| 38. | H | A | E | G | T | F | T | S | D | Bip(2-Chloro) | Bip |
| 39. | H | A | E | G | T | F | T | S | D | Bip(4-Fluoro) | Bip |
| 40. | H | A | E | G | T | F | T | S | D | Bip(4-Trifluoromethyl) | Bip |
| 41. | H | A | E | G | T | F | T | S | D | 4-(1-Naphthyl)-Phe | Bip |
| 42. | H | A | E | G | T | F | T | S | D | 4-(3-thiophene)-Phe | Bip |
| 43. | H | A | E | G | T | F | T | S | D | 4-(3-Quinoline)-Phe | Bip |
| 44. | H | A | E | G | T | F | T | S | D | Bip(2-Me) | Phe(penta-Fluoro) |
| 45. | H | A | E | G | T | F | T | S | D | Bip(2-OMe) | Phe(penta-Fluoro) |
| 46. | H | A | E | G | T | F | T | S | D | Bip(2-Trifluoromethyl) | Phe(penta-Fluoro) |
| 47. | H | A | E | G | T | F | T | S | D | Bip(2-Trifluoromethyl) | Phe(penta-Fluoro) |
| 48. | H | A | E | G | T | F | T | S | D | Bip(2-Chloro) | Phe(penta-Fluoro) |
| 49. | H | A | E | G | T | F | T | S | D | Bip(2-Fluoro) | Phe(penta-Fluoro) |
| 50. | H | A | E | G | T | F | T | S | D | Bip(4-OMe) | Phe(penta-Fluoro) |
| 51. | H | A | E | G | T | F | T | S | D | Bip(3,4-Methylenedioxy) | Phe(penta-Fluoro) |
| 52. | H | A | E | G | T | F | T | S | D | Bip(2-Me) | 2-Nal |
| 53. | H | A | E | G | T | F | T | S | D | Bip(2-OMe) | 2-Nal |
| 54. | H | A | E | G | T | F | T | S | D | Bip(2-Trifluoromethyl) | 2-Nal |
| 55. | H | A | E | G | T | F | T | S | D | Bip(2-Chloro) | 2-Nal |
| 56. | H | A | E | G | T | F | T | S | D | Bip(2-Fluoro) | 2-Nal |
| 57. | H | A | E | G | T | F | T | S | D | Bip(4-Me) | 2-Nal |
| 58. | H | A | E | G | T | F | T | S | D | Bip(4-OMe) | 2-Nal |
| 59. | H | A | E | G | T | F | T | S | D | Bip(3,4-Methylenedioxy) | 2-Nal |
| 60. | H | A | E | G | T | F | T | S | D | 4-(1-Naphthyl)-Phe | 2-Nal |
| 61. | H | A | E | G | T | F | T | S | D | 4-(3-thiophene)-Phe | 2-Nal |
| 62. | H | A | E | G | T | F | T | S | D | Bip(2-Me) | Phe(4-Me) |
| 63. | H | A | E | G | T | F | T | S | D | Bip(2-Trifluoromethyl) | Phe(4-Me) |
| 64. | H | A | E | G | T | F | T | S | D | Bip(2-Chloro) | Phe(4-Me) |
| 65. | H | A | E | G | T | F | T | S | D | Bip(2-Fluoro) | Phe(4-Me) |
| 66. | H | A | E | G | T | F | T | S | D | Bip(4-Chloro) | Phe(4-Me) |
| 67. | H | A | E | G | T | F | T | S | D | Bip(4-Me) | Phe(4-Me) |
| 68. | H | A | E | G | T | F | T | S | D | Bip(4-Fluoro) | Phe(4-Me) |
| 69. | H | A | E | G | T | F | T | S | D | Bip(4-OMe) | Phe(4-Me) |
| 70. | H | A | E | G | T | F | T | S | D | Bip(3,4-Methylenedioxy) | Phe(4-Me) |

TABLE I-continued

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| 71. | H | A | E | G | T | F | T | S | D | 4-(1-Naphthyl)-Phe | Phe(4-Me) |
| 72. | H | A | E | G | T | F | T | S | D | Bip(3-Phenyl) | Phe(4-Me) |
| 73. | H | A | E | G | T | F | T | S | D | Bip(2-Me) | Bip(2-Fluoro) |
| 74. | H | A | E | G | T | F | T | S | D | Bip(2-Me) | Bip(4-Phenyl) |
| 75. | H | A | E | G | T | F | T | S | D | Bip(2-Me) | Bip(3-OMe) |
| 76. | H | A | E | G | T | F | T | S | D | Bip(2-Me) | 4-(3-Pyridyl)-Phe |
| 77. | H | A | E | G | T | F | T | S | D | Phe(penta-Fluoro) | Bip(4-OMe) |
| 78. | H | A | E | G | T | F | T | S | D | Bip(2-Me) | Bip(3-Acetamido) |
| 79. | H | A | E | G | T | F | T | S | D | Bip(2-Me) | Bip(4-Isopropyl) |
| 80. | H | A | E | G | T | F | T | S | D | Bip | 4-(1-Naphthyl)-Phe |
| 81. | H | A | E | G | T | F | T | S | D | Bip | 4-(3-Pyridyl)-Phe |
| 82. | H | A | E | G | T | F | T | S | D | Phe(penta-Fluoro) | Bip(2-Me) |
| 83. | H | A | E | G | T | F | T | S | D | 2-Nal | Bip(2-Me) |
| 84. | H | A | E | G | T | F | T | S | D | Phe(4-Iodo) | Bip(2-Me) |
| 85. | H | A | E | G | T | F | T | S | D | Phe(3,4-di-Chloro) | Bip(2-Me) |
| 86. | H | A | E | G | T | F | T | S | D | Tyr(Bzl) | Bip(2-Me) |
| 87. | H | A | E | G | T | F | T | S | D | homoPhe | Bip(2-Me) |
| 88. | H | A | E | G | T | F | T | S | D | Bip(2,4-di-OMe) | Bip |
| 89. | H | A | E | G | T | F | T | S | D | 4-(4-(3,5-dimethylisoxazole))-Phe | Bip |
| 90. | H | A | E | G | T | F | T | S | D | Bip(2-Me,4-OMe) | Bip |
| 91. | H | A | E | G | T | F | T | S | D | Bip(2,6-di-Me) | Bip |
| 92. | H | A | E | G | T | F | T | S | D | Bip(2,4-di-Me) | Bip |
| 93. | H | A | E | G | T | F | T | S | D | Bip(2,3-di-Me) | Bip |
| 94. | H | A | E | G | T | F | T | S | D | Bip(4-Trifluoromethoxy) | Bip |
| 95. | H | A | E | G | T | F | T | S | D | Bip(4-Et) | Bip |
| 96. | H | A | E | G | T | F | T | S | D | 4-(2-Naphthyl)-Phe | Bip |
| 97. | H | A | E | G | T | F | T | S | D | 4-(4-Dibenzofuran)-Phe | Bip |
| 98. | H | A | E | G | T | F | T | S | D | Bip(2,6-di-OMe) | Bip(2-Me) |
| 99. | H | A | E | G | T | F | T | S | D | 4-(2,4-dimethoxy-pyrimidine)-Phe | Bip(2-Me) |
| 100. | H | A | E | G | T | F | T | S | D | Bip(2,4,6-Trimethyl) | Bip(2-Me) |
| 101. | H | A | E | G | T | F | T | S | D | 4-(4-(3,5-dimethylisoxazole))-Phe | Bip(2-Me) |
| 102. | H | A | E | G | T | F | T | S | D | Bip(2,4-di-Chloro) | Bip(2-Me) |
| 103. | H | A | E | G | T | F | T | S | D | Bip(2,6-di-Me) | Bip(2-Me) |
| 104. | H | A | E | G | T | F | T | S | D | Bip(2,4-di-Me) | Bip(2-Me) |
| 105. | H | A | E | G | T | F | T | S | D | Bip(2,3-di-Me) | Bip(2-Me) |
| 106. | H | A | E | G | T | F | T | S | D | Bip(4-Et) | Bip(2-Me) |
| 107. | H | A | E | G | T | F | T | S | D | Bip(4-SMe) | Bip(2-Me) |
| 108. | H | A | E | G | T | F | T | S | D | Bip(4-OEt) | Bip(2-Me) |
| 109. | H | A | E | G | T | F | T | S | D | 4-(2-Naphthyl)-Phe | Bip(2-Me) |
| 110. | H | A | E | G | T | F | T | S | D | 4-(2-Benzo(b)thiophene)-Phe | Bip(2-Me) |
| 111. | H | A | E | G | T | F | T | S | D | 4-(2-Benzo(b)furan)-Phe | Bip(2-Me) |
| 112. | H | A | E | G | T | F | T | S | D | 4-(4-Dibenzofuran)-Phe | Bip(2-Me) |
| 113. | H | A | E | G | T | F | T | S | D | 4-(4-Phenoxathiin)-Phe | Bip(2-Me) |
| 114. | H | A | E | G | T | F | T | S | D | Bip(2-Me) | Bip(4-Et) |
| 115. | H | A | E | G | T | F | T | S | D | Bip(2-Me) | Bip(4-SMe) |
| 116. | H | A | E | G | T | F | T | S | D | Bip(2-Me) | Bip(2,4-di-Me) |
| 117. | H | A | E | G | T | F | T | S | D | Bip(2-Me) | Bip(2-Me,4-OMe) |
| 118. | H | A | E | G | T | F | T | S | D | Bip(2-Me) | Bip(2,3-di-Me) |
| 119. | H | A | E | G | T | F | T | S | D | Bip(2-Me) | 4-(2-naphthyl)-Phe |
| 120. | H | A | E | G | T | F | T | S | D | Bip(2-Me) | Bip(2-OEt) |
| 121. | H | A | E | G | T | F | T | S | D | Bip(2-Me) | Bip(2-Et,4-OMe) |
| 122. | H | A | E | G | T | F | T | S | D | Bip(2-Et) | Bip(3-Et) |
| 123. | H | A | E | G | T | F | T | S | D | Bip(2-Et) | Bip(3-Propyl) |
| 124. | H | A | E | G | T | F | T | S | D | Bip(2-Et) | Bip(3-Phenyl) |
| 125. | H | A | E | G | T | F | T | S | D | Bip(2-Et) | Bip(3-OEt) |
| 126. | H | A | E | G | T | F | T | S | D | Bip(2-Et) | Bip(4-Et) |
| 127. | H | A | E | G | T | F | T | S | D | Bip(2-Et) | Bip(4-SMe) |
| 128. | H | A | E | G | T | F | T | S | D | Bip(2-Et) | Bip(4-OCF3) |
| 129. | H | A | E | G | T | F | T | S | D | Bip(2-Et) | Bip(4-OEt) |
| 130. | H | A | E | G | T | F | T | S | D | Bip(2-Et) | Bip(2-Me,4-OMe) |
| 131. | H | A | E | G | T | F | T | S | D | Bip(2-Et) | Bip(2,6-di-Me) |
| 132. | H | A | E | G | T | F | T | S | D | Bip(2-Et) | Bip(2,4,6-tri-Me) |
| 133. | H | A | E | G | T | F | T | S | D | Bip(2-Et) | Bip(2-Phenyl) |

TABLE I-continued

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| 134. | H | A | E | G | T | F | T | S | D | Bip(2-Et) | Bip(2-Isopropyl) |
| 135. | H | A | E | G | T | F | T | S | D | Bip(2-Et) | 4-(2-naphthyl)-Phe |
| 136. | H | A | E | G | T | F | T | S | D | Bip(2-Et) | Bip(2,5-di-OMe) |
| 137. | H | A | E | G | T | F | T | S | D | Bip(2-Et) | Bip(2-OEt) |
| 138. | H | A | E | G | T | F | T | S | D | Bip(3,4-di-OMe) | Bip(2-Me) |
| 139. | H | A | E | G | T | F | T | S | D | Bip(2-Et) | Bip(2-Et,4-OMe) |
| 140. | H | ala | E | G | Nle | Phe(penta-Fluoro) | T | S | D | Bip(2-Me) | Bip(2-Me) |
| 141. | H | A | H | G | T | F | T | H | D | Bip(2-Me) | Bip(2-Me) |
| 142. | H | A | H | G | T | F | T | S | D | Bip(2-Me) | Bip(2-Me) |
| 143. | H | A | E | G | T | F | T | S | D | Bip | Phe(4-Trifluoromethyl) |
| 144. | H | Aib | E | G | Nle | Phe(penta-Fluoro) | T | S | D | Bip(2-Et) | Bip(2-Me) |
| 145. | H | Aib | D | G | T | F | T | S | D | Bip(2-Et) | Bip(2-Me) |
| 146. | H | Aib | D | G | Nle | F | T | H | D | Bip(2-Et) | Bip(2-Me) |
| 147. | H | Aib | H | G | T | Phe(penta-Fluoro) | T | H | D | Bip(2-Et) | Bip(2-Me) |
| 148. | H | Aib | D | G | Nle | F | T | S | D | Bip(2-Et) | Bip(2-Me) |
| 149. | H | Aib | H | G | T | F | T | H | D | Bip(2-Et) | Bip(2-Me) |
| 150. | H | ala | asp | G | Nle | Phe(penta-Fluoro) | T | S | D | Bip(2-Me) | Bip(2-Me) |
| 151. | H | A | D | G | Nle | F | T | H | D | Bip(2-Et) | Bip(2-Me) |
| 152. | H | ala | D | G | Nle | Phe(penta-Fluoro) | T | H | D | Bip(2-Et) | Bip(2-Me) |
| 153. | H | A | D | G | T | (L)-Phe(2,4-di-Fluoro) | T | S | D | Bip(2-Me) | Bip(2-Me) |
| 154. | H | Aib | asp | G | Nle | Phe(penta-Fluoro) | T | S | D | Bip(2-Me) | Bip(2-Me) |
| 155. | H | A | D | G | T | (D)-Phe(2,4-di-Fluoro) | T | S | D | Bip(2-Me) | Bip(2-Me) |
| 156. | H | Aib | D | G | Nle | F | T | H | D | Bip(2-Me) | Bip(2-Me) |
| 157. | H | Aib | D | G | Nle | F | T | S | D | Bip(2-Me) | Bip(2-Me) |
| 158. | H | Aib | D | G | T | F | T | S | D | Bip(2-Me) | Bip(2-Me) |
| 159. | H | Aib | D | G | T | Phe(penta-Fluoro) | T | S | D | Bip(2-Me) | Bip(2-Me) |
| 160. | H | Aib | E | G | Nle | F | T | S | D | Bip(2-Me) | Bip(2-Me) |
| 161. | H | Aib | E | G | Nle | Phe(penta-Fluoro) | T | H | D | Bip(2-Me) | Bip(2-Me) |
| 162. | H | Aib | E | G | Nle | Phe(penta-Fluoro) | T | S | D | Bip(2-Me) | Bip(2-Me) |
| 163. | H | Aib | E | G | T | Phe(penta-Fluoro) | T | H | D | Bip(2-Me) | Bip(2-Me) |
| 164. | H | Aib | E | G | T | Phe(penta-Fluoro) | T | S | D | Bip(2-Me) | Bip(2-Me) |
| 165. | H | Aib | H | G | T | F | T | H | D | Bip(2-Me) | Bip(2-Me) |
| 166. | H | Aib | H | G | T | F | T | S | D | Bip(2-Me) | Bip(2-Me) |
| 167. | H | Aib | H | G | T | Phe(penta-Fluoro) | T | H | D | Bip(2-Me) | Bip(2-Me) |
| 168. | his | Aib | D | G | Nle | Phe(penta-Fluoro) | T | S | D | Bip(2-Me) | Bip(2-Me) |
| 169. | H | ala | D | G | Nle | Phe(penta-Fluoro) | T | S | D | Bip(2-Et) | Bip(2-Me) |
| 170. | H | Aib | D | G | Nle | Phe(penta-Fluoro) | T | S | D | Bip(2-Et) | Bip(2-Me) |
| 171. | H | Aib | D | G | Nle | Phe(penta-Fluoro) | T | S | D | Bip(2-Me) | Bip(2-Et) |
| 172. | H | Aib | D | G | Nle | Phe(penta-Fluoro) | T | S | D | Phe(penta-Fluoro) | Bip(2-Me) |
| 173. | H | ala | D | G | T | Phe(penta-Fluoro) | T | S | D | Bip(2-Et) | Bip(2-Me) |
| 174. | H | Aib | E | G | T | Phe(penta-Fluoro) | T | S | D | Bip(2-Et) | Bip(2-Me) |
| 175. | H | A | D | G | T | (L)-Phe(2,5-di-F) | T | S | D | Bip(2-Me) | Bip(2-Me) |
| 176. | H | A | Dpr | G | T | Phe(penta-Fluoro) | T | S | D | Bip(2-Et) | Bip(2-Me) |
| 177. | H | Aib | Dpr | G | T | Phe(penta-Fluoro) | T | S | D | Bip(2-Et) | Bip(2-Me) |
| 178. | H | ala | Dpr | G | Nle | Phe(penta-Fluoro) | T | S | D | Bip(2-Et,2'-Me) | Bip(2-Me) |
| 179. | H | A | Dpr | G | T | Phe(penta-Fluoro) | T | S | D | Bip(2-Et,2'-Me) | Bip(2-Me) |
| 180. | H | A | Dpr | G | T | F | T | S | D | Bip(2-Et,2'-Me) | Bip(2-Me) |
| 181. | H | Iva | E | G | T | F | T | S | D | Bip(2-Me) | Bip(2-Me) |
| 182. | H | A | E | G | homo-Leu | F | T | S | D | Bip(2-Me) | Bip(2-Me) |
| 183. | H | A | E | G | T | homoLeu | T | S | D | Bip(2-Me) | Bip(2-Me) |
| 184. | H | A | E | G | T | F | T | S | D | 2-(9,10-Dihydro-phenanthrenyl)-Ala | Bip(2-Me) |
| 185. | H | A | E | G | T | F | T | S | D | Bip(2-Et) | 2-(9,10-Dihydro-phenanthrenyl)-Ala |
| 186. | H | A | E | G | T | F | T | S | D | Bip(2-Et) | 2-(9,10-Dihydro-phenanthrenyl)-Ala |
| 187. | H | A | E | G | T | F | T | S | D | 2-(9,10-Dihydro-phenanthrenyl)-Ala | 2-(9,10-Dihydro-phenanthrenyl)-Ala |
| 188. | H | A | E | G | T | F | T | S | D | 2-(9,10-Dihydro-phenanthrenyl)-Ala | 2-(9,10-Dihydro-phenanthrenyl)-Ala |
| 189. | H | A | E | G | T | F | T | S | D | 2-FluorenylAla | 2-(9,10-Dihydro-phenanthrenyl)-Ala |
| 190. | H | A | E | G | T | F | T | S | D | 2-(9,10-Dihydro-phenanthrenyl)-Ala | 2-FluorenylAla |
| 191. | H | A | E | G | T | F | T | S | D | 2-(9,10-Dihydro- | 2-FluorenylAla |

TABLE I-continued

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| | | | | | | | | | | phenanthrenyl)-Ala | |
| 192. | H | A | E | G | T | F | T | S | D | Bip(2-Et,2'-Et) | Bip |
| 193. | H | A | E | D | T | F | T | S | D | Bip(2-Et,2'-Et) | Bip(2-Me) |
| 194. | H | ala | D | G | Nle | Phe(penta-Fluoro) | T | S | D | Bip(2-Et,4-OMe) | Bip(2-Me) |
| 195. | H | A | E | G | T | F | T | S | D | Bip(2-Propyl,2'-Me) | Bip |
| 196. | H | A | D | G | T | L-α-Me-Phe | T | S | D | Bip | Bip(2-Et) |
| 197. | H | A | D | G | T | L-α-Me-Phe | T | S | D | Bip(2-Et) | Bip(2-Et) |
| 198. | H | A | D | G | T | L-α-Me-Phe | T | S | D | Bip(2-Me) | Bip(2-Et) |
| 199. | H | ala | E | G | T | L-α-Me-Phe | T | S | D | Bip(2-Et) | Bip(2-Me) |
| 200. | H | A | D | G | T | L-α-Me-Phe | T | S | D | Bip | Bip |
| 201. | H | ala | asp | G | Nle | L-α-Me-Phe | T | S | D | Bip(2-Me) | Bip(2-Me) |
| 202. | H | ala | D | G | nle | L-α-Me-Phe | T | S | D | Bip(2-Me) | Bip(2-Me) |
| 203. | H | Aib | D | G | nle | L-α-Me-Phe | T | S | D | Bip(2-Me) | Bip(2-Me) |
| 204. | H | Aib | D | G | Nle | L-α-Me-Phe | thr | S | D | Bip(2-Me) | Bip(2-Me) |
| 205. | H | Aib | D | G | Nle | L-α-Me-Phe | T | ser | D | Bip(2-Me) | Bip(2-Me) |
| 206. | H | Aib | D | G | Nle | L-α-Me-Phe | T | S | D | Bip(2-Me) | Bip |
| 207. | H | G | E | G | T | F | T | S | D | Bip(2-Me) | Bip(2-Me) |
| 208. | H | A | E | G | T | F | T | S | D | Bip(2-Et,4-OMe) | Bip(2,4-di-Me) |
| 209. | H | A | E | G | T | F | T | S | D | Bip(2-Et,4-OMe) | Bip(4-OMe) |
| 210. | H | A | E | G | T | F | T | S | D | Bip(2-Et,4-OMe) | Bip(3-Me) |
| 211. | H | A | E | G | T | F | T | S | D | Bip(2-CH2OH,4-OMe) | Bip(2-Me) |
| 212. | H | A | E | G | T | F | T | S | D | Bip(2-Me) | Bip(2-Propyl,2'-Me) |
| 213. | H | A | E | G | T | F | T | S | D | Bip(2-Et,4-OMe) | Bip(2,3,4,5-tetra-Me) |
| 214. | H | A | E | G | T | F | T | S | D | Bip(2-Et) | Bip(2,2'-di-Me) |
| 215. | H | A | D | G | T | Phe(2-OMe) | T | S | D | Bip(2-Me) | Bip(2-Me) |
| 216. | H | A | D | G | T | Phe(2-Hydroxy) | T | S | D | Bip(2-Me) | Bip(2-Me) |
| 217. | H | A | D | G | T | Phe(2-Iodo) | T | S | D | Bip(2-Me) | Bip(2-Me) |
| 218. | H | A | D | G | T | Phe(3-OMe) | T | S | D | Bip(2-Me) | Bip(2-Me) |
| 219. | H | A | D | G | T | Tyr(3-Iodo) | T | S | D | Bip(2-Me) | Bip(2-Me) |
| 220. | H | A | D | G | T | Tyr(3-NO2) | T | S | D | Bip(2-Me) | Bip(2-Me) |
| 221. | H | A | D | G | T | (L)-Phe(2,3-di-Fluoro) | T | S | D | Bip(2-Me) | Bip(2-Me) |
| 222. | H | A | D | G | T | Tyr(2,6-di-Me) | T | S | D | Bip(2-Me) | Bip(2-Me) |
| 223. | H | A | D | G | T | 2-ThienylAla | T | S | D | Bip(2-Me) | Bip(2-Me) |
| 224. | H | A | D | G | T | (D)-Phe(2,3-di-Fluoro) | T | S | D | Bip(2-Me) | Bip(2-Me) |
| 225. | H | A | E | G | T | F | T | S | D | Bip(2-Et,2'-Me) | Bip(2-Et) |
| 226. | H | ala | D | G | Nle | F | T | S | D | Bip(2-Et,2'-Me) | Bip(2-Me) |
| 227. | H | Acc3 | D | G | Nle | Phe(penta-Fluoro) | T | S | D | Bip(2-Me) | Bip(2-Me) |
| 228. | H | Acc3 | D | G | Nle | F | T | H | D | Bip(2-Me) | Bip(2-Me) |
| 229. | H | Acc3 | D | G | T | Phe(penta-Fluoro) | T | H | D | Bip(2-Me) | Bip(2-Me) |
| 230. | H | Acc3 | D | G | Nle | Phe(penta-Fluoro) | T | H | D | Bip(2-Me) | Bip(2-Me) |
| 231. | H | A | D | G | T | Phe(2-Trifluoromethyl) | T | S | D | Bip(2-Me) | Bip(2-Me) |
| 232. | H | A | D | G | T | Phe(2,4-di-Chloro) | T | S | D | Bip(2-Me) | Bip(2-Me) |
| 233. | H | 2-Abu | E | G | T | F | T | S | D | Bip(2-Me) | Bip(2-Me) |
| 234. | his | A | asp | G | Nle | Phe(penta-Fluoro) | T | S | D | Bip(2-Me) | Bip(2-Me) |
| 235. | H | A | E | G | Nle | Phe(penta-Fluoro) | T | H | D | Bip(2-Et) | Bip(2-Et) |
| 236. | H | Aib | D | G | T | Phe(penta-Fluoro) | T | S | D | Bip(2-Et) | Bip(2-Me) |
| 237. | H | Aib | E | G | Nle | Phe(penta-Fluoro) | T | H | D | Bip(2-Et) | Bip(2-Me) |
| 238. | H | A | E | G | T | Phe(2-Me) | T | S | D | Bip(2-Me) | Bip(2-Me) |
| 239. | H | A | E | G | T | F | T | S | D | Bip(2-Et) | Bip(2-Et) |
| 240. | H | A | E | G | T | F | T | S | D | Bip(2-Et,4-OMe) | Bip |
| 241. | H | A | E | G | T | Phe(2-Chloro) | T | S | D | Bip(2-Me) | Bip(2-Me) |
| 242. | H | A | E | G | T | F | T | S | D | Bip(2-Et,2'-Me) | Bip(2,2'-di-Me) |
| 243. | H | A | γ-carboxy-Glu | G | T | F | T | S | D | Bip(2-Me) | Bip(2-Me) |
| 244. | H | A | C | G | T | F | T | S | D | Bip(2-Me) | Bip(2-Me) |
| 245. | H | ala | E | G | Nle | L-α-Me-Phe | T | S | D | Bip(2-Et) | Bip(2-Me) |
| 246. | H | L-4-ThioPro | E | G | T | F | T | S | D | Bip | Bip |
| 247. | H | A | E | G | T | F | T | S | D | Bip | Bip(2,2'-di-Me) |
| 248. | H | A | E | G | T | F | T | S | D | Bip(2-Me) | Bip(2,2'-di-Me) |
| 249. | H | A | E | G | T | F | T | S | D | Bip(2'-Me) | Bip(2-Me) |
| 250. | H | A | E | G | T | F | T | S | D | Bip | Bip(2'-Me) |
| 251. | H | A | E | G | T | F | T | S | D | Bip(2-Me) | Bip(2'-Me) |
| 252. | H | A | E | G | T | F | T | S | D | Bip(2'-Me) | Bip |
| 253. | H | Aib | E | G | Nle | Phe(penta-Fluoro) | T | S | D | bip(2'-Me) | Bip(2-Me) |
| 254. | H | A | E | G | T | F | T | S | D | Bip(2'-Me) | Bip(2,2'-di-Me) |
| 255. | H | A | E | G | T | F | T | S | D | Bip(2'-Me) | Bip(2'-Me) |
| 256. | H | A | E | G | T | F | T | S | D | Bip(2,2'-di-Me) | Bip |
| 257. | H | A | E | G | T | F | T | S | D | Bip(2,2'-di-Me) | Bip(2-Me) |
| 258. | H | A | E | G | T | F | T | S | D | Bip(2,2'-di-Me) | Bip(2-Et) |

TABLE I-continued

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| 259. | H | A | E | G | T | F | T | S | D | Bip(2,2'-di-Me) | Bip(2,2'-di-Me) |
| 260. | H | A | E | G | T | F | T | S | D | Bip(2-Me) | Phe(4-n-Butyl) |
| 261. | H | A | E | G | T | F | T | S | D | Bip(2-Me) | Phe(3-Phenyl) |
| 262. | H | A | E | G | T | F | T | S | D | Bip(2-Me) | Phe(4-Cyclohexyl) |
| 263. | H | A | E | G | T | F | T | S | D | Bip(2-Me) | Phe(4-Phenoxy) |
| 264. | H | A | E | G | T | F | T | S | D | Phe(4-n-Butyl) | Bip(2-Me) |
| 265. | H | A | E | G | T | F | T | S | D | Phe(4-Cyclohexyl) | Bip(2-Me) |
| 266. | H | A | E | G | T | F | T | S | D | Phe(4-Phenoxy) | Bip(2-Me) |
| 267. | H | A | D | G | T | Phe(3-Fluoro) | T | S | D | Bip(2-Me) | Bip(2-Me) |
| 268. | H | A | D | G | T | Phe(4-Fluoro) | T | S | D | Bip(2-Me) | Bip(2-Me) |
| 269. | H | A | D | G | T | Phe(3,4-di-Fluoro) | T | S | D | Bip(2-Me) | Bip(2-Me) |
| 270. | H | A | D | G | T | Phe(3,5-di-Fluoro) | T | S | D | Bip(2-Me) | Bip(2-Me) |
| 271. | H | A | D | G | T | Phe(3,4,5-tri-Fluoro) | T | S | D | Bip(2-Me) | Bip(2-Me) |
| 272. | H | ala | D | G | Nle | F | T | H | D | Bip(2-Me) | Bip(2-Me) |
| 273. | H | ala | D | G | T | Phe(penta-Fluoro) | T | H | D | Bip(2-Me) | Bip(2-Me) |
| 274. | H | ala | E | G | Nle | Phe(penta-Fluoro) | T | H | D | Bip(2-Me) | Bip(2-Me) |
| 275. | H | A | H | G | Nle | Phe(penta-Fluoro) | T | H | D | Bip(2-Me) | Bip(2-Me) |
| 276. | H | A | D | G | Nle | Phe(penta-Fluoro) | T | S | D | Bip(2,4-di-OMe) | Bip(2-Me) |
| 277. | H | A | E | G | T | F | T | S | D | Bip(2-Me,4-OMe) | Bip(3,4-Methylenedioxy) |
| 278. | H | A | E | G | T | F | T | S | D | Bip(2-Et) | Bip(3,4-Methylenedioxy) |
| 279. | H | A | D | G | T | F | T | S | D | Bip(2,4-di-OMe) | 4-(1-Naphthyl)-Phe |
| 280. | H | A | E | G | T | F | T | S | D | Bip(2-Me,4-OMe) | 4-(1-Naphthyl)-Phe |
| 281. | H | A | D | G | T | F | T | S | D | Bip(2,4-di-OMe) | Bip(4-OMe) |
| 282. | H | A | E | G | T | F | T | S | D | Bip(2-Me,4-OMe) | Bip(4-OMe) |
| 283. | H | A | E | G | T | F | T | S | D | Bip(2,4-di-OMe) | Bip(4-Me) |
| 284. | H | A | E | G | T | F | T | S | D | Bip(2-Me,4-OMe) | Bip(4-Me) |
| 285. | H | A | D | G | T | F | T | S | D | Bip(2,4-di-OMe) | Bip(2,4-di-OMe) |
| 286. | H | A | E | G | T | F | T | S | D | Bip(2-Me,4-OMe) | Bip(2-Me,4-OMe) |
| 287. | H | A | D | G | T | F | T | S | D | Bip(2,4-di-Me) | Bip(2,4-di-Me) |
| 288. | H | A | E | G | T | F | T | S | D | Bip(2,4-di-OMe) | Bip(3-Me) |
| 289. | H | A | E | G | T | F | T | S | D | Bip(2-Me,4-OMe) | Bip(3-Me) |
| 290. | H | A | 4-Thiazoyl-Ala | G | T | F | T | S | D | Bip(2-Me) | Bip(2-Me) |
| 291. | H | ala | D | G | Nle | Phe(penta-Fluoro) | T | H | D | Bip(2-Me) | Bip(2-Me) |
| 292. | H | A | E | G | T | F | T | S | D | Bip(2-Et,4,5-Methylenedioxy) | Bip(2-Me) |
| 293. | H | N-Me-Ala | E | G | Nle | Phe(penta-Fluoro) | T | H | D | Bip(2-Et) | Bip(2-Me) |
| 294. | H | N-Me-Ala | D | G | Nle | Phe(penta-Fluoro) | T | S | D | Bip(2-Me) | Bip(2-Me) |
| 295. | H | N-Me-Ala | D | G | T | Phe(penta-Fluoro) | T | S | D | Bip(2-Me) | Bip(2-Me) |
| 296. | H | N-Me-Ala | E | G | Nle | Phe(penta-Fluoro) | T | H | D | Bip(2-Me) | Bip(2-Me) |
| 297. | H | N-Me-Ala | E | G | T | Phe(penta-Fluoro) | T | S | D | Bip(2-Me) | Bip(2-Me) |
| 298. | H | Sarcosyl | E | G | T | F | T | S | D | Bip(2-Me) | Bip(2-Me) |
| 299. | H | A | E | G | T | F | T | S | D | Bip(3-CH2NH2) | Bip(2-Me) |
| 300. | H | A | E | G | T | F | T | S | D | Bip(2-CH2NH2) | Bip(2-Me) |
| 301. | H | A | E | G | T | F | T | S | D | Bip(4-CH2NH2) | Bip(2-Me) |
| 302. | H | A | E | G | T | F | T | S | D | Bip(3-CH2—COOH) | Bip(2-Me) |
| 303. | H | A | E | G | T | F | T | S | D | Bip(2-Me) | Bip(2'-CH2—COOH) |
| 304. | H | A | E | G | T | F | T | S | D | Bip(2-Me) | (D,L)-Bip(2-CH2—COOH) |
| 305. | H | A | E | G | T | F | T | S | D | Bip(2-Me) | Bip(4-CH2—COOH) |
| 306. | H | A | E | G | T | F | T | S | D | Bip(2-Me) | Bip(3-CH2—COOH) |
| 307. | H | A | E | G | T | F | T | S | D | Bip(2-Me) | Bip(3-CH2NH2) |
| 308. | H | A | E | G | T | F | T | S | D | Bip(2-Me) | Bip(4-CH2NH2) |
| 309. | H | A | E | G | T | F | T | S | D | Bip(2-Me) | Bip(2-CH2NH2) |
| 310. | H | A | E | G | T | F | T | S | D | Phe[4-(1-propargyl)] | Bip(2-Me) |
| 311. | H | A | E | G | T | F | T | S | D | Phe[4-(1-propenyl)] | Bip(2-Me) |
| 312. | H | A | asp | G | T | L-α-Me-Phe | T | S | D | Bip(2-Et) | Bip(2-Me) |
| 313. | H | A | D | G | thr | L-α-Me-Phe | T | S | D | Bip(2-Et) | Bip(2-Me) |
| 314. | H | A | D | G | T | L-α-Me-Phe | T | S | asp | Bip(2-Et) | Bip(2-Me) |
| 315. | H | A | D | G | T | L-α-Me-Phe | T | S | D | bip(2-Et) | Bip(2-Me) |
| 316. | H | ala | asp | G | T | L-α-Me-Phe | T | S | D | Bip(2-Et) | Bip(2-Me) |
| 317. | H | Aib | D | G | T | L-α-Me-Phe | thr | S | D | Bip(2-Et) | Bip(2-Me) |
| 318. | H | Aib | D | G | T | L-α-Me-Phe | T | S | asp | Bip(2-Et) | Bip(2-Me) |
| 319. | H | ala | D | G | Nle | Phe(penta-Fluoro) | T | S | D | Bip(2-Me) | Bip(2-Me) |
| 320. | H | ala | D | G | Nle | Phe(penta-Fluoro) | T | S | D | bip(2-Et) | Bip(2-Me) |
| 321. | H | ala | D | G | Nle | Phe(penta-Fluoro) | T | S | D | Bip(2-Me) | bip(2-Me) |
| 322. | H | ala | D | G | Nle | Phe(penta-Fluoro) | T | S | D | Bip(2-Me) | bip(2-Et) |
| 323. | H | Aib | D | G | Nle | Phe(penta-Fluoro) | T | S | D | bip(2-Me) | Bip(2-Me) |

TABLE I-continued

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| 324. | H | Aib | D | G | Nle | Phe(penta-Fluoro) | T | S | D | bip(2-Et) | Bip(2-Me) |
| 325. | H | Aib | D | G | Nle | Phe(penta-Fluoro) | T | S | D | Bip(2-Me) | bip(2-Me) |
| 326. | H | Aib | D | G | Nle | Phe(penta-Fluoro) | T | S | D | Bip(2-Me) | bip(2-Et) |
| 327. | H | A | E | G | T | F | T | S | D | Bip(2-Me) | (D,L)-α-Me-Bip |
| 328. | H | A | E | G | T | F | T | S | D | Bip | (D,L)-α-Me-Bip |
| 329. | H | A | D | G | allo-Thr | L-α-Me-Phe | T | S | D | Bip(2-Et) | Bip(2-Me) |
| 330. | H | A | D | G | T | L-α-Me-Phe | allo-Thr | S | D | Bip(2-Et) | Bip(2-Me) |
| 331. | H | A | D | G | T | L-α-Me-Phe | T | hSer | D | Bip(2-Et) | Bip(2-Me) |
| 332. | H | A | D | G | T | L-α-Me-Phe | T | T | D | Bip(2-Et) | Bip(2-Me) |
| 333. | H | A | D | G | T | L-α-Me-Phe | T | S | E | Bip(2-Et) | Bip(2-Me) |
| 334. | H | A | E | G | Nle | F | T | S | D | Bip(2-Et) | Bip(2-Me) |
| 335. | H | A | asp | G | T | L-α-Me-Phe | T | S | D | Bip(2-Et) | Bip(2-Me) |
| 336. | H | Aib | D | G | thr | L-α-Me-Phe | T | S | D | Bip(2-Et) | Bip(2-Me) |
| 337. | H | Aib | D | G | T | L-α-Me-Phe | thr | S | D | Bip(2-Et) | Bip(2-Me) |
| 338. | H | Aib | D | G | T | L-α-Me-Phe | T | S | asp | Bip(2-Et) | Bip(2-Me) |
| 339. | H | A | D | G | T | L-α-Me-Phe | T | S | D | Bip(2-Et)-NH-[2-(penta-Fluoro-phenyl)ethyl] | |
| 340. | H | A | D | G | Nle | L-α-Me-Phe | T | S | D | Bip(2-Et)-NH-[2-(penta-Fluoro-phenyl)ethyl] | |
| 341. | H | Aib | E | G | T | L-α-Me-Phe | T | S | D | Bip(2-Et)-NH-[2-(penta-Fluoro-phenyl)ethyl] | |
| 342. | H | Aib | D | G | Nle | L-α-Me-Phe | T | S | D | Bip(2-Et)-NH-[2-(penta-Fluoro-phenyl)ethyl] | |
| 343. | H | Aib | asp | G | T | L-α-Me-Phe | T | S | D | Bip(2-Et) | Bip(2-Me) |
| 344. | H | ala | E | G | T | L-α-Me-Phe | T | S | D | Bip(2-Et) | Bip(2-Me) |
| 345. | H | ala | E | G | T | L-Phe(2,6-di-Fluoro) | T | S | D | Bip(2-Et) | Bip(2-Me) |
| 346. | H | N-Me-Ala | E | G | T | L-α-Me-Phe | T | S | D | Bip(2-Et) | Bip(2-Me) |
| 347. | H | A | N-Me-Glu | G | T | L-α-Me-Phe | T | S | D | Bip(2-Et) | Bip(2-Me) |
| 348. | H | A | E | N-Me-Gly | T | L-α-Me-Phe | T | S | D | Bip(2-Et) | Bip(2-Me) |
| 349. | H | A | D | G | Nle | (D,L)-α-Me-Phe(penta-Fluoro) | T | S | D | Bip(2-Et,4-OMe) | Bip(2-Me) |
| 350. | H | ala | D | G | Nle | (D,L)-α-Me-Phe(penta-Fluoro) | T | S | D | Bip(2-Et,4-OMe) | Bip(2-Me) |
| 351. | H | Aib | D | G | Nle | (D,L)-α-Me-Phe(penta-Fluoro) | T | S | D | Bip(2-Et,4-OMe) | Bip(2-Me) |
| 352. | H | ala | E | G | T | D-Phe(2,6-di-Fluoro) | T | S | D | Bip(2-Et) | Bip(2-Me) |
| 353. | H | Aib | D | G | T | D-Phe(2,6-di-Fluoro) | T | S | D | Bip(2-Et) | Bip(2-Me) |
| 354. | H | A | E | G | T | (D,L)-α-Me-Phe(penta-Fluoro) | T | S | D | Bip(2-Et,4-OMe) | Bip(2-Me) |
| 355. | H | A | D | G | T | (D,L)-α-Me-Phe(penta-Fluoro) | T | S | D | Bip(2-Et,4-OMe) | Bip(2-Me) |
| 356. | H | ala | E | G | T | (D,L)-α-Me-Phe(penta-Fluoro) | T | S | D | Bip(2-Et,4-OMe) | Bip(2-Me) |
| 357. | H | A | D | G | T | L-α-Me-Phe | T | S | D | Bip(2-Et) | bip(2-Et) |
| 358. | H | Aib | D | G | T | L-α-Me-Phe | T | S | D | Bip(2-Et) | bip(2-Me) |
| 359. | H | A | E | G | T | L-α-Me-Phe | T | S | D | Bip(3-OH) | Bip(2-Me) |
| 360. | H | A | E | G | T | L-α-Me-Phe | T | S | D | Bip(4-OH) | Bip(2-Me) |
| 361. | H | A | E | G | T | L-α-Me-Phe | T | S | D | Bip(2-OEt) | Bip(2-Me) |
| 362. | H | A | E | G | T | L-α-Me-Phe | T | S | D | Bip(3-OEt) | Bip(2-Me) |
| 363. | H | A | E | G | T | L-α-Me-Phe | T | S | D | Bip(3-OCF3) | Bip(2-Me) |
| 364. | H | A | E | G | T | L-α-Me-Phe | T | S | D | Bip(3-NO2) | Bip(2-Me) |
| 365. | H | A | E | G | T | L-α-Me-Phe | T | S | D | Bip(3-CF3) | Bip(2-Me) |
| 366. | H | A | E | G | T | L-α-Me-Phe | T | S | D | Bip(3-F) | Bip(2-Me) |
| 367. | H | A | E | G | T | L-α-Me-Phe | T | S | D | Bip(3-Cl) | Bip(2-Me) |
| 368. | H | A | E | G | T | L-α-Me-Phe | T | S | D | Bip(3-Ph) | Bip(2-Me) |
| 369. | H | A | E | G | T | L-α-Me-Phe | T | S | D | Bip(3-Et) | Bip(2-Me) |
| 370. | H | A | E | G | T | L-α-Me-Phe | T | S | D | Bip(3-i-Pr) | Bip(2-Me) |
| 371. | H | A | E | G | T | L-α-Me-Phe | T | S | D | Bip(4-i-Pr) | Bip(2-Me) |
| 372. | H | A | E | G | T | L-α-Me-Phe | T | S | D | Bip(4-Pr) | Bip(2-Me) |
| 373. | H | A | E | G | T | L-α-Me-Phe | T | S | D | Bip(3-Pr) | Bip(2-Me) |
| 374. | H | A | E | G | T | L-α-Me-Phe | T | S | D | Bip(2,5-di-Cl) | Bip(2-Me) |
| 375. | H | A | E | G | T | L-α-Me-Phe | T | S | D | Bip(2,5-di-F) | Bip(2-Me) |
| 376. | H | A | E | G | T | L-α-Me-Phe | T | S | D | Bip(3,4-di-F) | Bip(2-Me) |
| 377. | H | A | E | G | T | L-α-Me-Phe | T | S | D | Bip(3,4-di-Cl) | Bip(2-Me) |
| 378. | H | A | E | G | T | L-α-Me-Phe | T | S | D | Bip(2,3-di-Cl) | Bip(2-Me) |
| 379. | H | A | E | G | T | L-α-Me-Phe | T | S | D | Bip(3-NHAc) | Bip(2-Me) |
| 380. | H | A | E | G | T | L-α-Me-Phe | T | S | D | Bip(4-NHAc) | Bip(2-Me) |
| 381. | H | A | E | G | Aoc | L-α-Me-Phe | T | S | D | Bip(2-Et) | Bip(2-Me) |

TABLE I-continued

| SEQ ID NO: | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|
| 382. | H | A | D | G | Nle | F | T | S | D | Bip(2-Et) | Bip(2-Me) |
| 383. | H | ala | E | G | T | L-Phe(2-Fluoro) | T | S | D | Bip(2-Et) | Bip(2-Me) |
| 384. | H | Aib | D | G | Nle | (D,L)-α-Et-Phe | T | S | D | Bip(2-Et) | Bip(2-Me) |
| 385. | H | Aib | D | G | T | L-α-Me-Phe | T | (D,L)-α-Me-Ser | D | Bip(2-Et) | Bip(2-Me) |
| 386. | H | A | D | G | T | (L)-α-Me-Phe(2,6-di-Fluoro) | T | S | D | Bip(2-Et,4-OMe) | Bip(2-Me) |
| 387. | H | A | E | G | T | L-α-Me-Phe | T | S | D | Bip(4-t-Bu) | Bip(2-Me) |
| 388. | H | ala | E | G | Nle | (L)-α-Me-Phe(2,6-di-Fluoro) | T | S | D | Bip(2-Et,4-OMe) | Bip(2-Me) |
| 389. | H | ala | D | G | Nle | (L)-α-Me-Phe(2,6-di-Fluoro) | T | S | D | Bip(2-Et,4-OMe) | Bip(2-Me) |
| 390. | H | Aib | E | G | Nle | (L)-α-Me-Phe(2,6-di-Fluoro) | T | S | D | Bip(2-Et,4-OMe) | Bip(2-Me) |
| 391. | H | Aib | D | G | Nle | (L)-α-Me-Phe(2,6-di-Fluoro) | T | S | D | Bip(2-Et,4-OMe) | Bip(2-Me) |
| 392. | H | A | D | G | Nle | (L)-α-Me-Phe(2,6-di-Fluoro) | T | S | D | Bip(2-Et) | Bip(2-Me) |
| 393. | H | A | D | G | T | F | T | S | D | Bip(2-Et) | Bip(2-Me) |

Amino Acid Abbreviations and Structures

A = L-Ala; ala = D-Ala
Aib = α-aminoisobutyric acid
Bip = L-biphenylalanine; bip = D-biphenylalanine
C = L-Cys
D = L-Asp; asp = D-Asp
E = L-Glu
G = Gly
H = L-His; his = D-His
K = L-Lys
Nle = L-norleucine; nle = D-norleucine
F = L-Phe
S = L-Ser, ser = D-Ser
T = L-Thr; thr = D-Thr
Y = L-Tyr
W = L-Trp

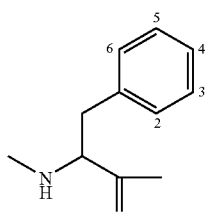

Numbering of the phenylalanine ring carbons

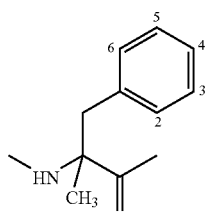

Numbering of the α-methyl-phenylalanine (α-Me-Phe) ring carbons

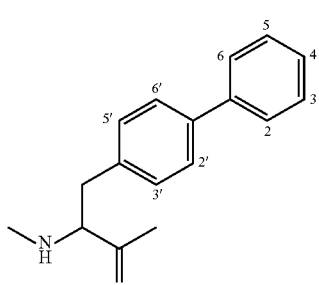

Numbering of the biphenylalanine ring carbons

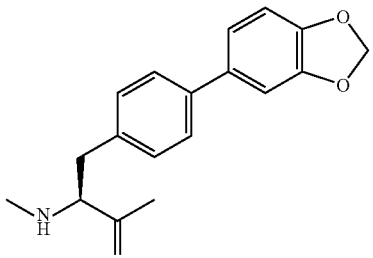

Bip(3,4-Methylenedioxy)

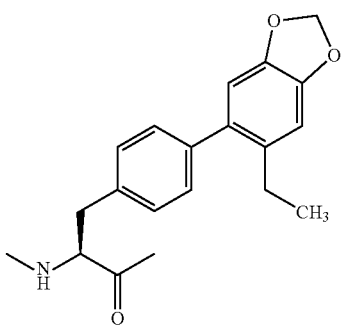

Bip(2-Et, 4-5-Methylenedioxy)

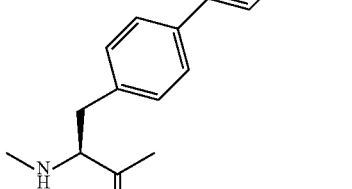

4-(2-Naphthyl)-Phe

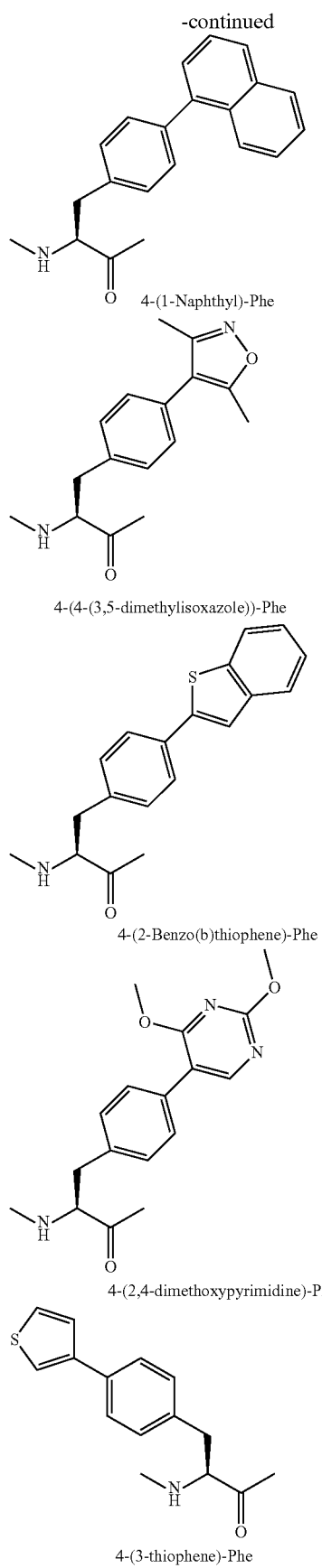
4-(1-Naphthyl)-Phe
4-(4-(3,5-dimethylisoxazole))-Phe
4-(2-Benzo(b)thiophene)-Phe
4-(2,4-dimethoxypyrimidine)-Phe
4-(3-thiophene)-Phe
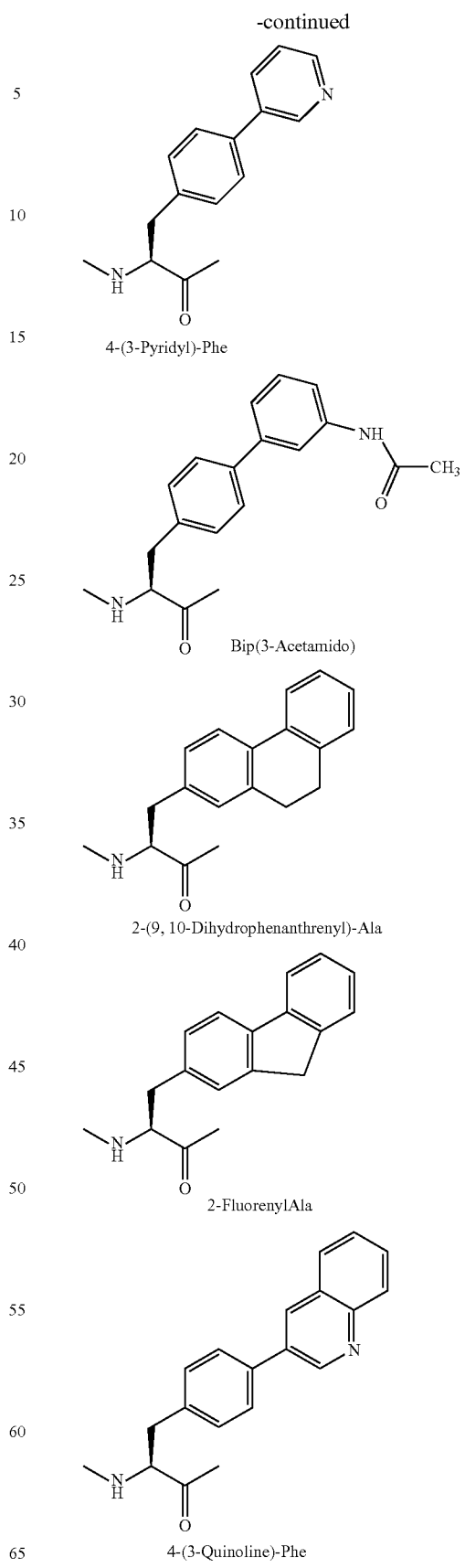
4-(3-Pyridyl)-Phe
Bip(3-Acetamido)
2-(9, 10-Dihydrophenanthrenyl)-Ala
2-FluorenylAla
4-(3-Quinoline)-Phe

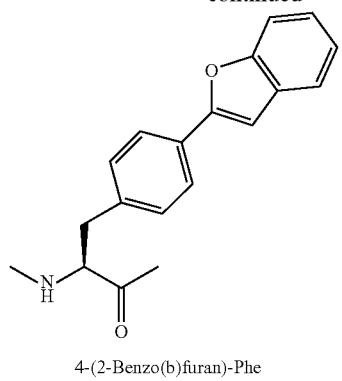
4-(2-Benzo(b)furan)-Phe
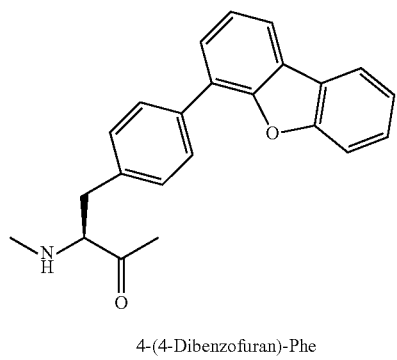
4-(4-Dibenzofuran)-Phe
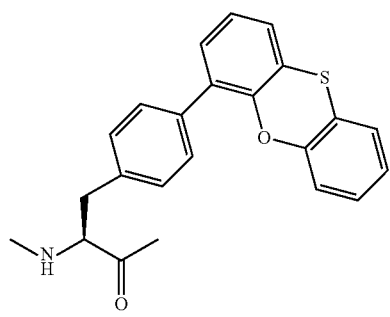
4-(4-Phenoxathiin)-Phe
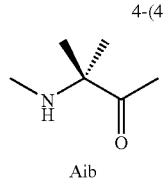
Aib
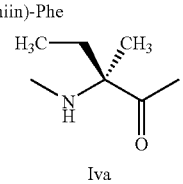
Iva
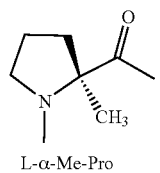
L-α-Me-Pro
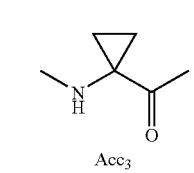
Acc₃
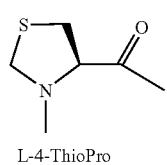
L-4-ThioPro
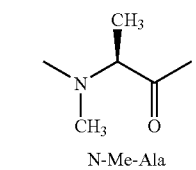
N-Me-Ala
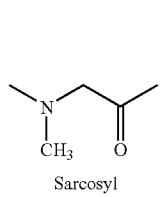
Sarcosyl
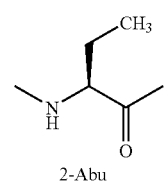
2-Abu
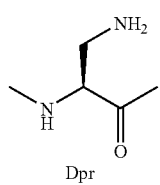
Dpr
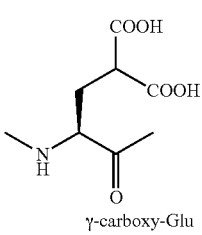
γ-carboxy-Glu
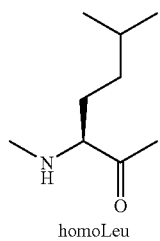
homoLeu
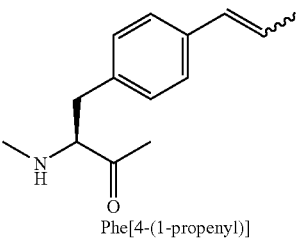
Phe[4-(1-propenyl)]
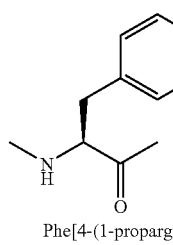
Phe[4-(1-propargyl)]
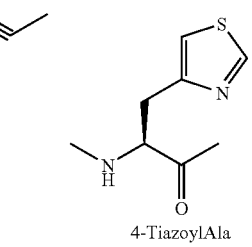
4-TiazoylAla
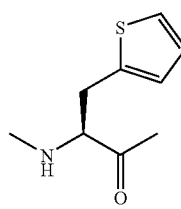
2-Thienyl-Ala
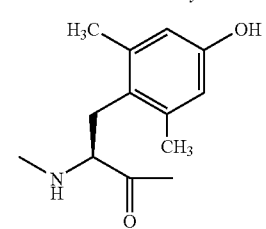
Tyr(2,6-di-Me)
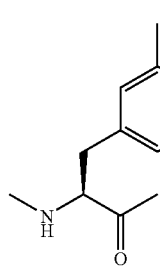
Tyr(3-Iodo)
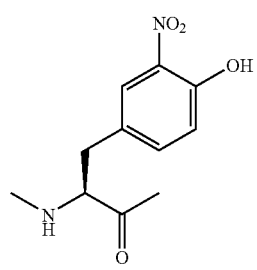
Tyr(3-Nitro)

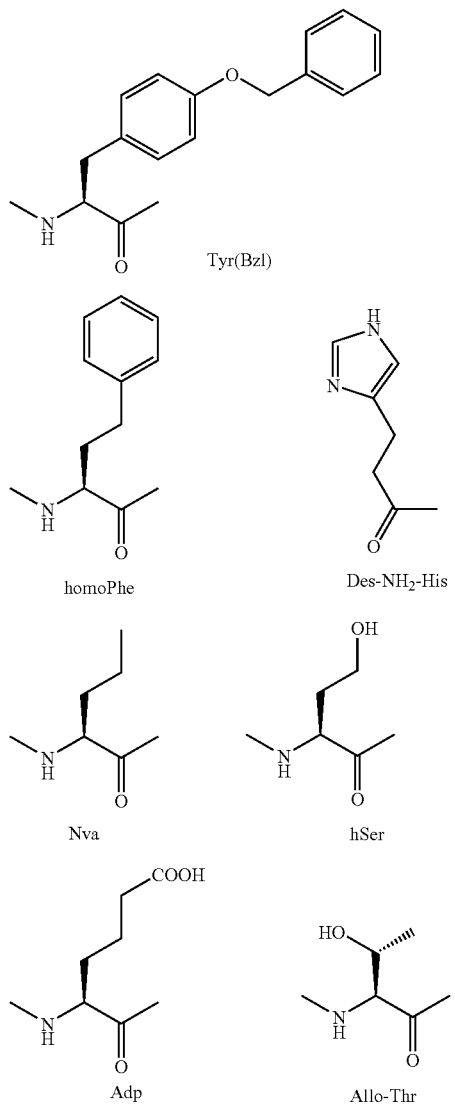
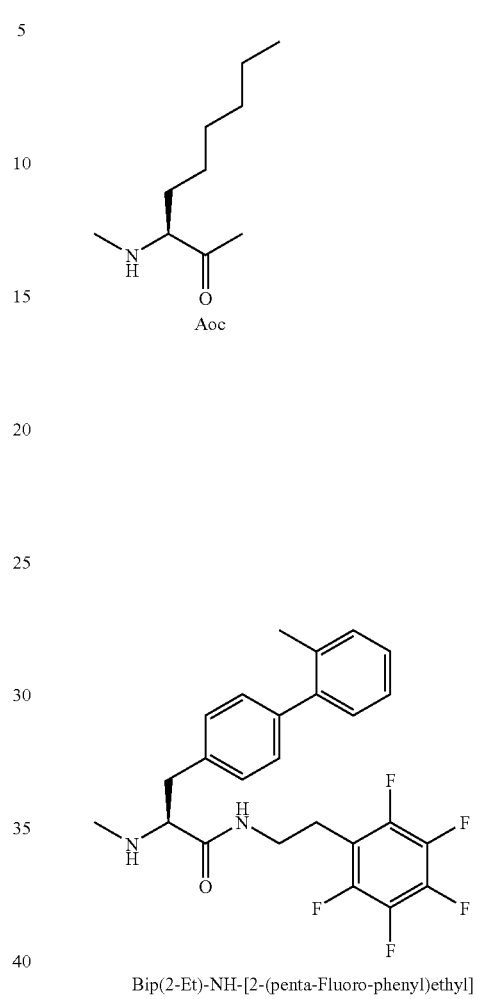

TABLE II

| SEQ ID No: | A | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|---|
| 394. | Acetyl | H | A | E | G | T | F | T | S | D | Bip | Bip |
| 395. | β-Ala | H | A | E | G | T | F | T | S | D | Bip | Bip |
| 396. | Ahx | H | A | E | G | T | F | T | S | D | Bip | Bip |
| 397. | D | H | A | E | G | T | F | T | S | D | Bip | Bip |
| 398. | E | H | A | E | G | T | F | T | S | D | Bip | Bip |
| 399. | F | H | A | E | G | T | F | T | S | D | Bip | Bip |
| 400. | G | H | A | E | G | T | F | T | S | D | Bip | Bip |
| 401. | K | H | A | E | G | T | F | T | S | D | Bip | Bip |
| 402. | Nva | H | A | E | G | T | F | T | S | D | Bip | Bip |
| 403. | N | H | A | E | G | T | F | T | S | D | Bip | Bip |
| 404. | R | H | A | E | G | T | F | T | S | D | Bip | Bip |
| 405. | S | H | A | E | G | T | F | T | S | D | Bip | Bip |
| 406. | T | H | A | E | G | T | F | T | S | D | Bip | Bip |
| 407. | V | H | A | E | G | T | F | T | S | D | Bip | Bip |
| 408. | W | H | A | E | G | T | F | T | S | D | Bip | Bip |
| 409. | Y | H | A | E | G | T | F | T | S | D | Bip | Bip |

TABLE II-continued

| SEQ ID No: | A | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|---|
| 410. | Caprolactam | H | A | E | G | T | F | T | S | D | Bip | Bip |
| 411. | Bip | H | A | E | G | T | F | T | S | D | Bip | Bip |
| 412. | Ser(Bzl) | H | A | E | G | T | F | T | S | D | Bip | Bip |
| 413. | 3-PyridylAla | H | A | E | G | T | F | T | S | D | Bip | Bip |
| 414. | Phe(4-Me) | H | A | E | G | T | F | T | S | D | Bip | Bip |
| 415. | Phe(pentafluoro) | H | A | E | G | T | F | T | S | D | Bip | Bip |

TABLE III

| SEQ ID NO: | R—CH$_2$— | Xaa1 | Xaa2 | Xaa3 | Xaa4 | Xaa5 | Xaa6 | Xaa7 | Xaa8 | Xaa9 | Y | Z |
|---|---|---|---|---|---|---|---|---|---|---|---|---|
| 416. | 4-Methylbenzyl | H | A | E | G | T | F | T | S | D | Bip(2-Me) | Bip(2-Me) |
| 417. | 4-Fluorobenzyl | H | A | E | G | T | F | T | S | D | Bip(2-Me) | Bip(2-Me) |
| 418. | Propyl | H | A | E | G | T | F | T | S | D | Bip(2-Me) | Bip(2-Me) |
| 419. | Hexyl | H | A | E | G | T | F | T | S | D | Bip(2-Me) | Bip(2-Me) |
| 420. | Cyclohexylmethyl | H | A | E | G | T | F | T | S | D | Bip(2-Me) | Bip(2-Me) |
| 421. | 6-Hydroxypentyl | H | A | E | G | T | F | T | S | D | Bip(2-Me) | Bip(2-Me) |
| 422. | 2-Thienylmethyl | H | A | E | G | T | F | T | S | D | Bip(2-Me) | Bip(2-Me) |
| 423. | 3-Thienylmethyl | H | A | E | G | T | F | T | S | D | Bip(2-Me) | Bip(2-Me) |
| 424. | Pentafluorobenzyl | H | A | E | G | T | F | T | S | D | Bip(2-Me) | Bip(2-Me) |
| 425. | 2-Naphthylmethyl | H | A | E | G | T | F | T | S | D | Bip(2-Me) | Bip(2-Me) |
| 426. | 4-Biphenylmethyl | H | A | E | G | T | F | T | S | D | Bip(2-Me) | Bip(2-Me) |
| 427. | 9-Anthracenylmethyl | H | A | E | G | T | F | T | S | D | Bip(2-Me) | Bip(2-Me) |
| 428. | Benzyl | H | A | E | G | T | F | T | S | D | Bip(2-Me) | Bip(2-Me) |
| 429. | (S)-(2-Amino-3-phenyl)propyl | H | A | E | G | T | F | T | S | D | Bip(2-Me) | Bip(2-Me) |
| 430. | Methyl | H | A | E | G | T | F | T | S | D | Bip | Bip |
| 431. | Benzyl- | H | A | E | G | T | F | T | S | D | Bip | Bip |
| 432. | 2-aminoethyl | H | A | E | G | T | F | T | S | D | Bip(2-Me) | Bip(2-Me) |
| 433. | (S)-2-Aminopropyl | H | A | E | G | T | F | T | S | D | Bip(2-Me) | Bip(2-Me) |

TABLE IV

| SEQ ID NO: | Xaa1 | Xaa2 | Xaa3 | Xaa4 | Xaa5 | Xaa6 | Xaa7 | Xaa8 | Xaa9 | Y | Z | B |
|---|---|---|---|---|---|---|---|---|---|---|---|---|
| 434. | H | A | E | G | T | F | T | S | D | Bip | 2-Nal | W |
| 435. | H | A | E | G | T | F | T | S | D | Bip | Phe(penta-Fluoro) | 2-Nal |
| 436. | H | A | E | G | T | F | T | S | D | Bip | Phe(penta-Fluoro) | Phe(penta-Fluoro) |
| 437. | H | A | E | G | T | F | T | S | D | Bip | Phe(penta-Fluoro) | Ser(Bzl) |
| 438. | H | A | E | G | T | F | T | S | D | Bip | Phe(penta-Fluoro) | Phe(4-NO$_2$) |
| 439. | H | A | E | G | T | F | T | S | D | Bip | Phe(penta-Fluoro) | 3-PyridylAla |
| 440. | H | A | E | G | T | F | T | S | D | Bip | Phe(penta-Fluoro) | Nva |
| 441. | H | A | E | G | T | F | T | S | D | Bip | Phe(penta-Fluoro) | K |
| 442. | H | A | E | G | T | F | T | S | D | Bip | Phe(penta-Fluoro) | D |
| 443. | H | A | E | G | T | F | T | S | D | Bip | Phe(penta-Fluoro) | S |
| 444. | H | A | E | G | T | F | T | S | D | Bip | Phe(penta-Fluoro) | H |
| 445. | H | A | E | G | T | F | T | S | D | Bip | Phe(penta-Fluoro) | Y |
| 446. | H | A | E | G | T | F | T | S | D | Bip | Phe(penta-Fluoro) | W |
| 447. | H | A | E | G | T | F | T | S | D | Bip | Phe(penta-Fluoro) | F |
| 448. | H | A | E | G | T | F | T | S | D | 2-Nal | Phe(penta-Fluoro) | W |
| 449. | H | A | E | G | T | F | T | S | D | Bip | Bip | Bip |
| 450. | H | A | E | G | T | F | T | S | D | Bip | Bip | Nva |
| 451. | H | A | E | G | T | F | T | S | D | Bip(2-Me) | Bip(2-Me) | ser |
| 452. | H | A | E | G | T | F | T | S | D | Bip(2-Me) | Bip(2-Me) | Gly-OH |
| 453. | H | A | E | G | T | F | T | S | D | Bip(2-Me) | Bip(2-Me) | β-Ala-OH |
| 454. | H | A | E | G | T | F | T | S | D | Bip(2-Me) | Bip(2-Me) | GABA-OH |
| 455. | H | A | E | G | T | F | T | S | D | Bip(2-Me) | Bip(2-Me) | APA-OH |

Additional compounds according to the present invention are shown here in Table V.

TABLE V

| SEQ ID NO: | A | Xaa1 | Xaa2 | Xaa3 | Xaa4 | Xaa5 | Xaa6 | Xaa7 | Xaa8 | Xaa9 | Y | Z—NH2 |
|---|---|---|---|---|---|---|---|---|---|---|---|---|
| 456. | Y | H | Aib | E | G | T | (L)-α-Me-Phe(2-Fluoro) | T | S | D | Bip(2-Et,4-OMe) | Bip(2-Me)-NH2 |
| 457. | Bip | H | Aib | E | G | T | (L)-α-Me-Phe(2-Fluoro) | T | S | D | Bip(2-Et,4-OMe) | Bip(2-Me)-NH2 |
| 458. | CH3CO | H | Aib | E | G | T | (L)-α-Me-Phe(2-Fluoro) | T | S | D | Bip(2-Et,4-OMe) | Bip(2-Me)-NH2 |
| 459. | CH3CH2CO | H | Aib | E | G | T | (L)-α-Me-Phe(2-Fluoro) | T | S | D | Bip(2-Et,4-OMe) | Bip(2-Me)-NH2 |
| 460. | Des-NH2-Tyr | H | Aib | E | G | T | (L)-α-Me-Phe(2-Fluoro) | T | S | D | Bip(2-Et,4-OMe) | Bip(2-Me)-NH2 |
| 461. | CH3OCO | H | Aib | E | G | T | (L)-α-Me-Phe(2-Fluoro) | T | S | D | Bip(2-Et,4-OMe) | Bip(2-Me)-NH2 |
| 462. | CH3NHCO | H | Aib | E | G | T | (L)-α-Me-Phe(2-Fluoro) | T | S | D | Bip(2-Et,4-OMe) | Bip(2-Me)-NH2 |
| 463. | CH3SO2 | H | Aib | E | G | T | (L)-α-Me-Phe(2-Fluoro) | T | S | D | Bip(2-Et,4-OMe) | Bip(2-Me)-NH2 |
| 464. | (L)-OH—CH(CH3)CO | H | Aib | E | G | T | (L)-α-Me-Phe(2-Fluoro) | T | S | D | Bip(2-Et,4-OMe) | Bip(2-Me)-NH2 |
| 465. | HO—CH2—CO— | H | Aib | E | G | T | (L)-α-Me-Phe(2-Fluoro) | T | S | D | Bip(2-Et,4-OMe) | Bip(2-Me)-NH2 |

Additional compounds according to the present invention are shown here in Table VI.

TABLE VI

| SEQ ID NO: | Xaa1 | Xaa2 | Xaa3 | Xaa4 | Xaa5 | Xaa6 | Xaa7 | Xaa8 | Xaa9 | Y | Z | B |
|---|---|---|---|---|---|---|---|---|---|---|---|---|
| 466. | H | Aib | E | G | T | (L)-α-Me-Phe(2-Fluoro) | T | S | D | Bip(2-Et,4-OMe) | Bip(2-Me) | Gly-OH |
| 467. | H | Aib | E | G | T | (L)-α-Me-Phe(2-Fluoro) | T | S | D | Bip(2-Et,4-OMe) | Bip(2-Me) | β-Ala-OH |
| 468. | H | Aib | E | G | T | (L)-α-Me-Phe(2-Fluoro) | T | S | D | Bip(2-Et,4-OMe) | Bip(2-Me) | GABA-OH |

EXAMPLE 12

Synthesis and Testing of a Peptide Corresponding to the "Message" Sequence of GLP-1 and of the Same Peptide to which an "address" Biphenylalanine Dipeptide Unit is Attached at the C-terminus The peptide corresponding to the N-terminal 1-9 sequence of GLP-1, His-Ala-Glu-Gly-Thr-Phe-Thr-Ser-Asp-NH2, which in this invention is referred to as the "message" sequence of GLP-1, and the GLP-1 11-mer peptide analog His-Ala-Glu-Gly-Thr-Phe-Thr-Ser-Asp-Bip-Bip-NH2, which is comprised of the message sequence of GLP-1 and of a C-terminal biphenylalanine dipeptide unit, were prepared using the methods described herein and tested in the cAMP cell-based assay describe in Example 13. The GLP-1 11-mer peptide analog stimulated cAMP production in a dose-response manner corresponding to an $EC_{50}$ value of 1.1 micromolar, determined as in Example 13. In the same assay, the $EC_{50}$ value determined for the peptide corresponding to the "message" sequence of GLP-1 was greater than 1 millimolar. The $EC_{50}$ value for GLP-1, used in the assay as a positive control, was less than 0.100 nanomolar.

EXAMPLE 13

Cyclic AMP Determination

The GLP-1 receptor is a G-protein coupled receptor. GLP-1 (7-36)-amide, the biologically active form, binds to the GLP-1 receptor and through signal transduction causes activation of adenylate cyclase and raises intracellular cAMP levels. To monitor agonism of peptide compounds in stimulating the GLP-1 receptor, adenyl cyclase activity was monitored by assaying for cellular cAMP levels. Full-length human glucagon-like peptide 1 receptor was stably expressed in CHO-K1 cells. The clones were screened for best expression of GLP-1R and CHO-GLP1R-19 was selected. Cells were cultured in Ham's F12 nutritional media (Gibco #11765-054), 10% FBS, 1× L-Glutamine, 1× Pen/Strep, and 0.4 mg/ml G418. CHO-GLP-1R-19 cells (2,500 in 100 µl of media) were plated into each well of a 96-well tissue culture microtiter plate and incubated in 5% $CO_2$ atmosphere at 37° C., for 72 h. On the day of the assay, cells were washed once with 100 µl of PBS. To cells in each well, 10 µl of compound and 90 µl of reaction media (Phenol red free DMEM media with low glucose (Gibco#11054-020), 0.1% BSA (Sigma #A7284), 0.3 mM IBMX (3-isobutyl-1 methylxanthine, Sigma #I5879) were added and incubated at 37° C. for 1 h. The compounds were initially screened at 1 µM and 10 µM for stimulation of cAMP. Dose dependence for compounds showing 50% of maximal GLP-1 (at 100 nM) activity was determined at half-log concentrations in duplicate. After incubation, medium was removed and cells were washed once with 100 µl of PBS. Fifty µl of lysis reagent-1 from the cyclic AMP SPA kit (Amersham Pharmacia Biotech, RPA 559; reagents were reconstituted according to the kit instructions) was added into each well. The plate was shaken at room temperature for 15 min. Twenty µl of lysate was transferred into each well of a 96-well OptiPlate (Packard #6005190) and 60 µl of SPA immunoreagent from the kit was added. After incubation at room temperature for 15-18 h, plates were counted 2 min each/well in a TopCount NXT(Packard).

In each 96-well plate, GLP-1 (control), and five compounds (in duplicate) were run at seven half-log doses. Ten nM GLP-1 was plated into ten additional wells to serve as a reference standard for determination of maximal activity. The data obtained was processed in Excel-fit database. From a cyclic AMP standard curve, the amounts of released cAMP were determined and the % maximal activity was calculated and plotted against log compound concentration. The data was analyzed by nonlinear regression curve fit (sigmoidal dose) to determine the $EC_{50}$ of the compounds.

EXAMPLE 14

In-Vivo Studies

Figure 2:
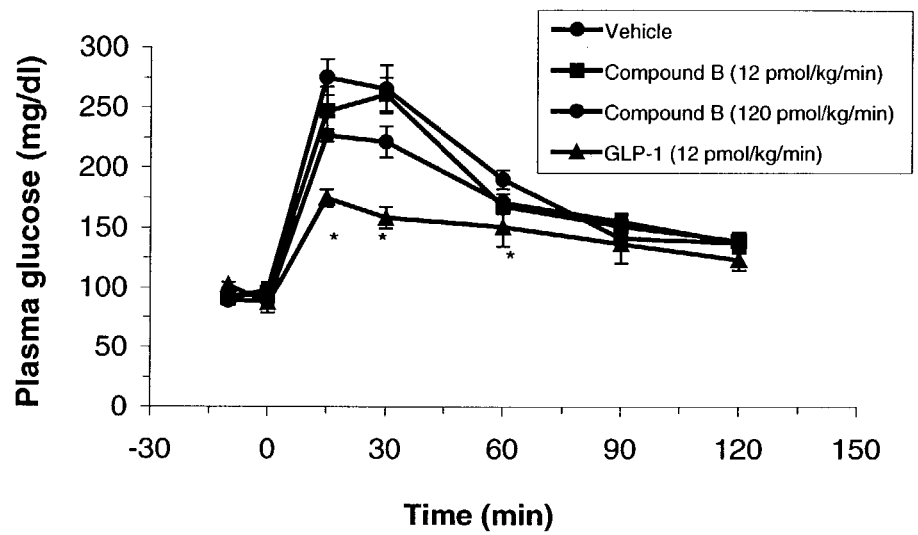
FIG. 2 illustrates the effects of intravenous infusion of Compound B and GLP-1 on plasma glucose in scGT in rats.
Figure 3:
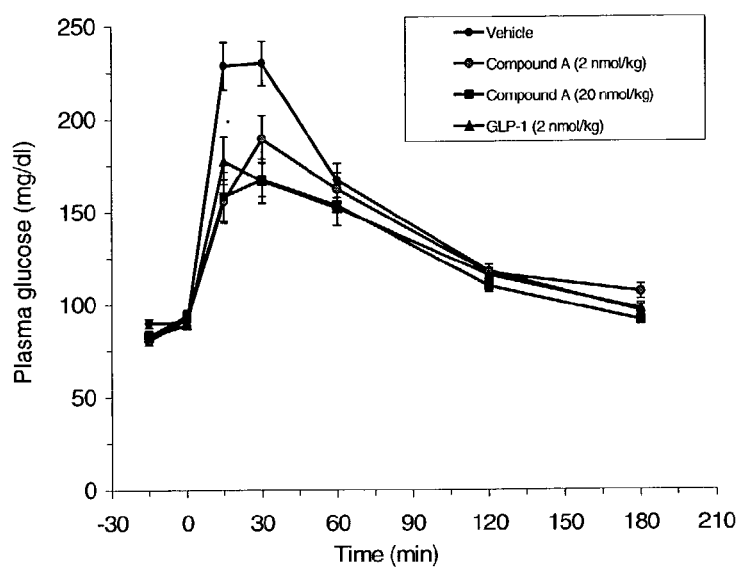
FIG. 3 illustrates the effects of subcutaneous injection of Compound A and GLP-1 on plasma glucose in scGTT in rats.
Figure 4:
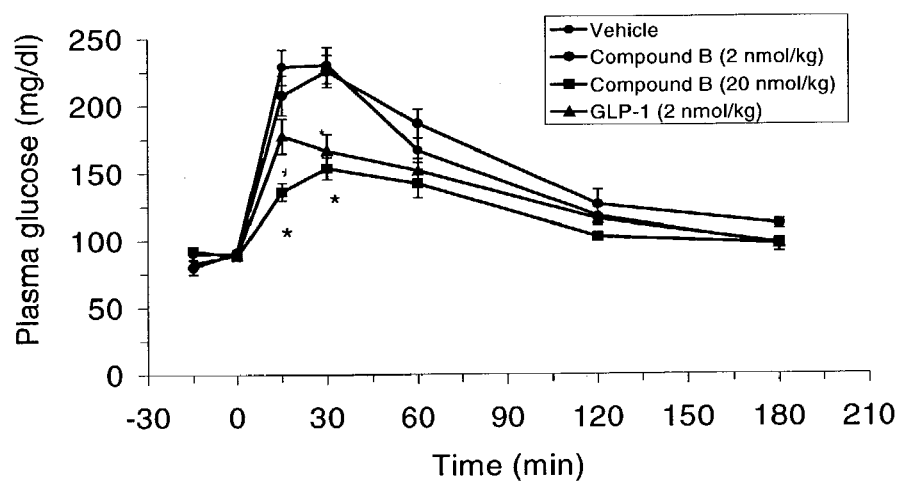
FIG. 4 illustrates the effects of subcutaneous injection of Compound B and GLP-1 on plasma glucose in scGTT in rats.

The in-vivo glucose lowering properties for four representative 11-mer peptides, compound A, compound B, compound C and compound D in a rat model is described below. Continuous intravenous infusion of compound A and compound B significantly attenuated the postprandial glucose excursion curve in subcutaneous glucose tolerance test (scGTT) (see FIG. 1 and FIG. 2). In addition, these two 11-mer peptides administered by subcutaneous injection also produced a significant glucose lowering effect in this model (see FIG. 3 and FIG. 4). A clear dose-response relationship was observed following both continuous intravenous infusion and subcutaneous bolus injection of the analogs for their glucose lowering effects. The significant glucose lowering effect for compound A and compound B was observed at 12 and 120 pmol/kg/min, respectively, when the compound was administered by continuous infusion. For the subcutaneous administration, the maximum effective doses for Compound A and Compound B were about 2 and 20 nmol/kg, respectively.

Figure 5:
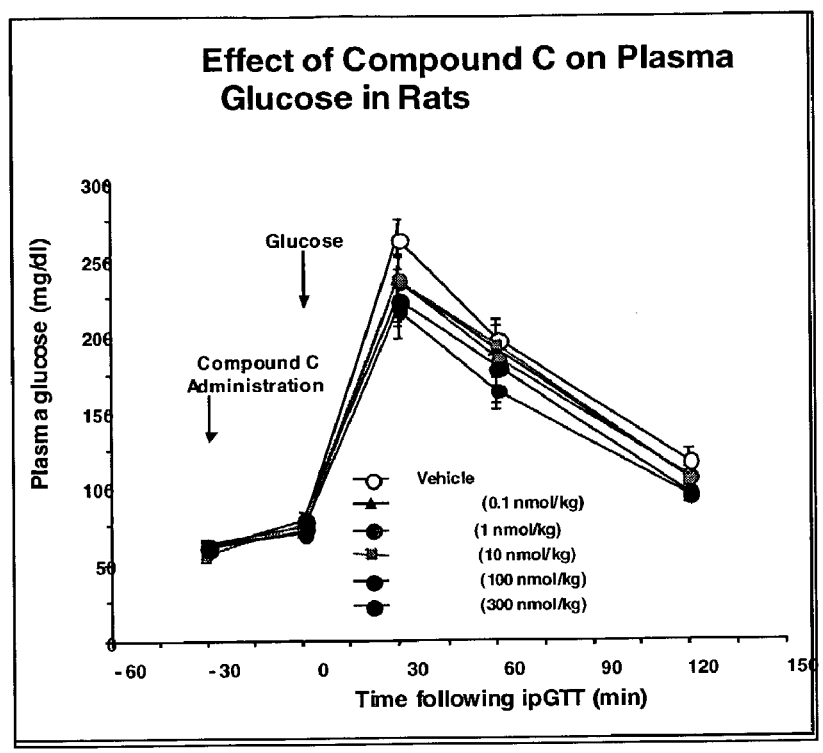
FIG. 5 illustrates the effects of subcutaneous injection of Compound C on plasma glucose in an ipGTT model in rats.
Figure 6:
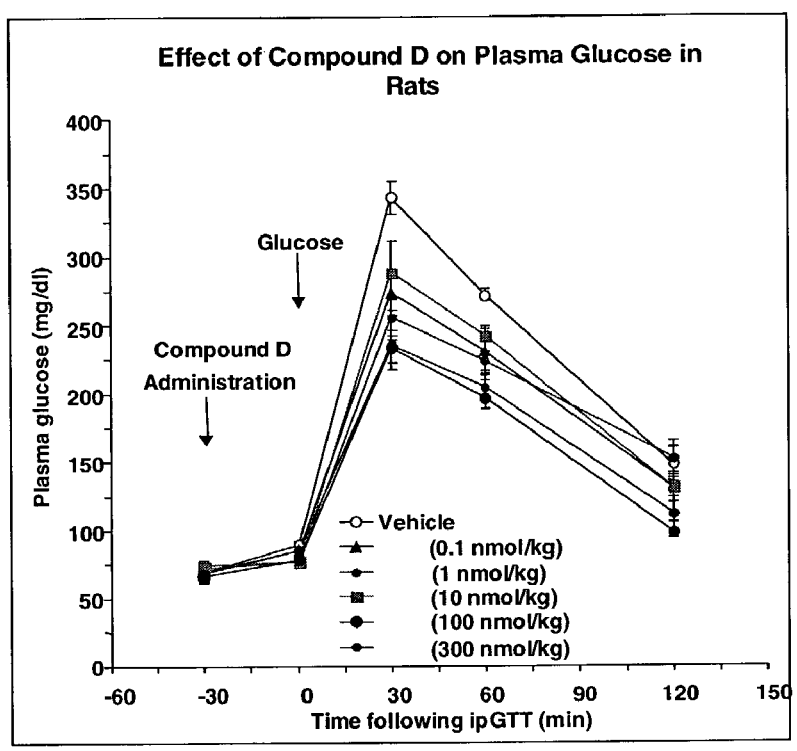
FIG. 6 illustrates the effects of subcutaneous injection of Compound D on plasma glucose in an ipGTT model in rats.
Figure 7:
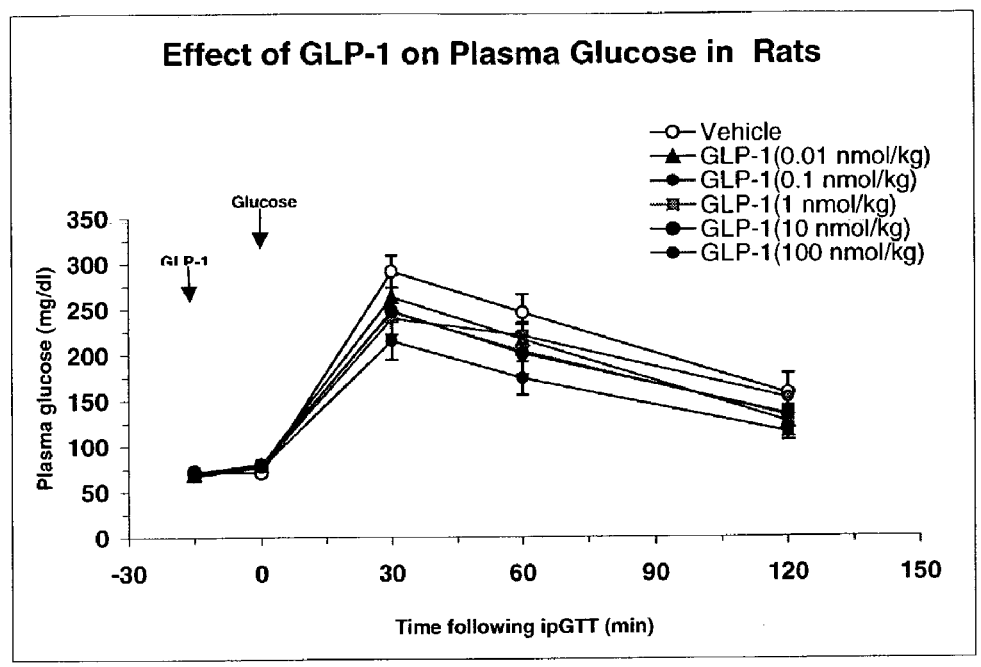
FIG. 7 illustrates the effects of subcutaneous injection of GLP-1 on plasma glucose in an ipGTT model in rats.

For compounds C and D, studies using subcutaneous injection in a rat intraperitoneal glucose tolerance test (ipGTT) model showed that significant glucose excursion attenuation could be achieved for both compounds in a dose-related fashion (see FIGS. 5 and 6). FIG. 7 shows the effects of native GLP-1 in this model.

UTILITY & COMBINATIONS

A. Utilities

The present invention provides novel GLP peptide mimics, with a preference for mimicking GLP-1, such that the compounds of the present invention have agonist activity for the GLP-1 receptor. Further, the GLP peptide mimics of the present invention exhibit incresased stability to proteolytic cleavage as compared to GLP-1 native sequences.

Accordingly, the compounds of the present invention can be administered to mammals, preferably humans, for the treatment of a variety of conditions and disorders, including, but not limited to, treating or delaying the progression or onset of diabetes (preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis, hypertension, AIDS, intestinal diseases (such as necrotizing enteritis, microvillus inclusion disease or celiac disease), inflammatory bowel syndrome, chemotherapy-induced intestinal mucosal atrophy or injury, anorexia nervosa, osteoporosis, dysmetabolic syndrome, as well as inflammatory bowel disease (such as Crohn's disease and ulcerative colitis). The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GLP-1 peptide mimics or other suitable therapeutic agents useful in the treatment of the aforementioned disorders including: anti-diabetic agents; anti-hyperglycemic agents; hypolipidemic/lipid lowering agents; anti-obesity agents (including appetite supressants/modulators) and anti-hypertensive agents. In addition, the compounds of the present invention may be combined with one or more of the following therapeutic agents; infertility agents, agents for treating polycystic ovary syndrome, agents for treating growth disorders, agents for treating frailty, agents for treating arthritis, agents for preventing allograft rejection in transplantation, agents for treating autoimmune diseases, anti-AIDS agents, anti-osteoporosis agents, agents for treating immunomodulatory diseases, antithrombotic agents, agents for the treatment of cardiovascular disease, antibiotic agents, anti-psychotic agents, agents for treating chronic inflammatory bowel disease or syndrome and/or agents for treating anorexia nervosa.

Examples of suitable anti-diabetic agents for use in combination with the compounds of the present invention include biguanides (e.g., metformin or phenformin), glucosidase inhibitors (e.g, acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), DPP-IV inhibitors, and SGLT2 inhibitors.

Other suitable thiazolidinediones include Mitsubishi's MCC-555 (disclosed in U.S. Pat. No. 5,594,016), GlaxoWelcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), and in U.S. application Ser. No. 09/644,598, filed Sep. 18, 2000, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable DPP4 inhibitors that may be used in combination with the compounds of the invention include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540, 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996) employing dosages as set out in the above references.

Suitable meglitinides include nateglinide (Novartis) or KAD1229 (PF/Kissei).

Examples of other suitable glucagon-like peptide-1 (GLP-1, ) compounds that may be used in combination with the GLP-1 mimics of the present invention include GLP-1(1-36) amide, GLP-1(7-36) amide, GLP-1(7-37) (as disclosed in U.S. Pat. No. 5,614,492 to Habener), as well as AC2993 (Amylin), LY-315902 (Lilly) and NN-2211 (NovoNordisk).

Examples of suitable hypolipidemic/lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination with one or more compounds of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel).

(1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds of the invention include SCH48461 (Schering-Plough), as well as those disclosed in Atherosclerosis 115, 45-63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a NPY receptor antagonist, a MCH antagonist, a GHSR antagonist, a CRH antagonist, a beta 3 adrenergic agonist, a lipase inhibitor, a serotonin (and dopamine) reuptake inhibitor, a thyroid receptor beta drug and/or an anorectic agent.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064, with AJ9677, L750,355 and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

Examples of thyroid receptor beta compounds which may be optionally employed in combination with compounds of the present invention include thyroid receptor ligands, such as those disclosed in WO97/21993 (U. Cal SF), WO99/00353 (KaroBio) and GB98/284425 (KaroBio), with compounds of the KaroBio applications being preferred.

The anorectic agent which may be optionally employed in combination with compounds of the present invention include dexamphetamine, phentermine, phenylpropanolamine or mazindol, with dexamphetamine being preferred.

Examples of suitable anti-psychotic agents include clozapine, haloperidol, olanzapine (Zyprexa®), Prozac® and aripiprazole (Abilify®).

The aforementioned patents and patent applications are incorporated herein by reference.

The above other therapeutic agents, when employed in combination with the compounds of the present invention may be used, for example, in those amounts indicated in the Physician's Desk Reference, as in the patents set out above or as otherwise determined by one of ordinary skill in the art.

Dosage and Formulation

A suitable GLP-1 peptide mimic can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraocular, intravenous, or intestinal administration. The compound is formulated according to the route of administration based on acceptable pharmacy practice (Fingl et al., in *The Pharmacological Basis of Therapeutics*, Ch. 1, p. 1, 1975; *Remington's Pharmaceutical Sciences*, $18^{th}$ ed., Mack Publishing Co, Easton, Pa., 1990).

The pharmaceutically acceptable GLP-1 peptide mimic composition of the present invention can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The composition of the present invention can also be administered in oral, intravenous (bolus or infusion), intraperitoneal, subcutaneous, transdermally or intramuscular form, all using dosage forms well known to those of ordinary skill in the pharmaceutical arts. The composition may be administered alone, but generally will be administered with a pharmaceutical carrier selected on the basis of the chosen route of administration and standard pharmaceutical practice.

The dosage regimen for the composition of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.1 ng to 10.0 mg per min per Kg body weight. The composition of this invention may be administered in a single daily dose, or the total daily dosage may be administered in divided doses of two, three, or four times daily. The composition of this invention may also be administered by a depot formulation that will allow sustained release of the drug over a period of days/weeks/months as desired.

The composition of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The composition is typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propallant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The composition of the present invention may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same and compositions containing the same.

The compositions of the present invention may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the composition of the present invention may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.1 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company, 1995, a standard reference text in this field Representative useful pharmaceutical dosage forms for administration of the compound of this invention can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring for example, 1.5% by weight of active ingredient in 10% by volume propylene glycol and water. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

Obviously, numerous modifications and variations of the present invention are possible in light of the above teachings. It is therefore understood that within the scope of the appended claims, the invention may be practiced otherwise than as specifically described herein.

The present invention is not to be limited in scope by the specific embodiments described that are intended as single illustrations of individual aspects of the invention. Functionally equivalent methods and components in addition to those shown and described herein will become apparent to those skilled in the art from the foregoing description and accompanying drawings. Such modifications are intended to fall within the scope of the appended claims.

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial
<220> FEATURE:
<223> OTHER INFORMATION: naturally or non-naturally occurring
<220> FEATURE:
<221> NAME/KEY: MISC_FEATURE
<222> LOCATION: (1)..(1)
<223> OTHER INFORMATION: wherein xaa is derivatized with A, as defined
                        in the specification
<220> FEATURE:
<221> NAME/KEY: misc_feature
<222> LOCATION: (2)..(8)
<223> OTHER INFORMATION: Xaa can be any naturally or non-naturally
                        occurring amino acid
<220> FEATURE:
<221> NAME/KEY: MISC_FEATURE
<222> LOCATION: (9)..(9)
<223> OTHER INFORMATION: wherein xaa is derivatized with Y and Z, which
                        are amino acid residues, and B, as defined in
                        the specification

<400> SEQUENCE: 1
```

```
Xaa Xaa Xaa Xaa Xaa Xaa Xaa Xaa Xaa
1               5

<210> SEQ ID NO 2
<211> LENGTH: 2
<212> TYPE: PRT
<213> ORGANISM: Artificial
<220> FEATURE:
<223> OTHER INFORMATION: naturally or non-naturally occurring
<220> FEATURE:
<221> NAME/KEY: misc_feature
<222> LOCATION: (1)..(1)
<223> OTHER INFORMATION: Xaa can be any naturally or non-naturally
                        occurring amino acid
<220> FEATURE:
<221> NAME/KEY: MISC_FEATURE
<222> LOCATION: (2)..(2)
<223> OTHER INFORMATION: wherein xaa is derivatized with Y and Z, which
                        are amino acid residues

<400> SEQUENCE: 2

Xaa Xaa
1

<210> SEQ ID NO 3
<211> LENGTH: 9
<212> TYPE: PRT
<213> ORGANISM: Artificial
<220> FEATURE:
<223> OTHER INFORMATION: naturally or non-naturally occurring
<220> FEATURE:
<221> NAME/KEY: MISC_FEATURE
<222> LOCATION: (1)..(1)
<223> OTHER INFORMATION: wherein xaa is esterified with a modified
                        amino acid
<220> FEATURE:
<221> NAME/KEY: misc_feature
<222> LOCATION: (2)..(8)
<223> OTHER INFORMATION: Xaa can be any naturally or non-naturally
                        occurring amino acid
<220> FEATURE:
<221> NAME/KEY: MISC_FEATURE
<222> LOCATION: (9)..(9)
<223> OTHER INFORMATION: wherein xaa is derivatized with Y and Z,
                        which are amino acid residues, and B, as
                        defined in the specification, and NH2

<400> SEQUENCE: 3

Xaa Xaa Xaa Xaa Xaa Xaa Xaa Xaa Xaa
1               5

<210> SEQ ID NO 4
<211> LENGTH: 8
<212> TYPE: PRT
<213> ORGANISM: Artificial
<220> FEATURE:
<223> OTHER INFORMATION: naturally or non-naturally occurring
<220> FEATURE:
<221> NAME/KEY: MISC_FEATURE
<222> LOCATION: (1)..(1)
<223> OTHER INFORMATION: wherein xaa is esterified with a modified
                        amino acid
<220> FEATURE:
<221> NAME/KEY: misc_feature
<222> LOCATION: (2)..(7)
<223> OTHER INFORMATION: Xaa can be any naturally or non-naturally
                        occurring amino acid
<220> FEATURE:
<221> NAME/KEY: MISC_FEATURE
<222> LOCATION: (8)..(8)
<223> OTHER INFORMATION: wherein xaa is derivatized with Y and Z,
                        which are amino acid residues, and resin

<400> SEQUENCE: 4
```

```
Xaa Xaa Xaa Xaa Xaa Xaa Xaa Xaa
1               5

<210> SEQ ID NO 5
<211> LENGTH: 8
<212> TYPE: PRT
<213> ORGANISM: Artificial
<220> FEATURE:
<223> OTHER INFORMATION: naturally or non-naturally occurring
<220> FEATURE:
<221> NAME/KEY: MISC_FEATURE
<222> LOCATION: (1)..(1)
<223> OTHER INFORMATION: wherein xaa is derivatized with a modified
                         amino acid
<220> FEATURE:
<221> NAME/KEY: misc_feature
<222> LOCATION: (2)..(7)
<223> OTHER INFORMATION: Xaa can be any naturally or non-naturally
                         occurring amino acid
<220> FEATURE:
<221> NAME/KEY: MISC_FEATURE
<222> LOCATION: (8)..(8)
<223> OTHER INFORMATION: wherein xaa is derivatized with Y and Z, which
                         are amino acid residues, and NH2

<400> SEQUENCE: 5

Xaa Xaa Xaa Xaa Xaa Xaa Xaa Xaa
1               5

<210> SEQ ID NO 6
<211> LENGTH: 8
<212> TYPE: PRT
<213> ORGANISM: Artificial
<220> FEATURE:
<223> OTHER INFORMATION: naturally or non-naturally occurring
<220> FEATURE:
<221> NAME/KEY: MISC_FEATURE
<222> LOCATION: (1)..(1)
<223> OTHER INFORMATION: wherein xaa is derivatized with a modified
                         amino acid
<220> FEATURE:
<221> NAME/KEY: misc_feature
<222> LOCATION: (2)..(7)
<223> OTHER INFORMATION: Xaa can be any naturally or non-naturally
                         occurring amino acid
<220> FEATURE:
<221> NAME/KEY: MISC_FEATURE
<222> LOCATION: (8)..(8)
<223> OTHER INFORMATION: wherein xaa is derivatized with Y and Z, which
                         are amino acid residues, and NH2

<400> SEQUENCE: 6

Xaa Xaa Xaa Xaa Xaa Xaa Xaa Xaa
1               5
```

What is claimed is:

1. An isolated polypeptide which binds and activates a GLP-1 receptor, said polypeptide comprising: an amino terminus comprising a first amino acid or a des-amino group; said amino terminus further comprising a capping moiety selected from the group consisting of acyl, lactic acid, hydroxy-acyl, urea, carbamate, and sulfonyl; said polypeptide further comprising SEQ ID NO: 469 wherein position five of SEQ ID NO: 469 optionally terminates as a carboxamide, substituted carboxamide, an ester, a free carboxylic acid, or an amino alcohol.

2. A pharmaceutical composition comprising a polypeptide of claim 1 and a pharmaceutically acceptable carrier.

3. A pharmaceutical combination comprising a polypeptide of claim 1 and at least one therapeutic agent selected from the group consisting of an antidiabetic agent, an anti-obesity agent, an anti-hypertensive agent, an anti-atherosclerotic agent and a lipid-lowering agent.

4. The combination of claim 3 wherein the antidiabetic agent is at least one agent selected from the group consisting of a biguanide, a sulfonyl urea, a glucosidase inhibitor, a peroxisome proliferator-activated receptor (PPAR) γ agonist, a PPAR α/γ dual agonist, an adipocyte lipid binding protein (aP2) inhibitor, a dipeptidyl peptidase 4 (DP4) inhibitor, an insulin sensitizer, a glucagon-like peptide-I (GLP-I), insulin and a meglitinide.

5. The combination of claim 4 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, fargiltizar, isaglitazone, reglitizar, balaglitazone, (Z)-1,4-bis{4-[(3,5-Dioxo-1,2,4-oxadiazolidin-2-yl)methyl]phenoxy}but-2-ene, rivoglitazone, rafaegron, repaglinide, nateglinide, (S)-2-benzyl-4-oxo-4-(cis-perhydmisoindol-2yl)butyric acid calcium salt, tesaglitizar, L-phenylalanine,N-[(1Z)-1-methyl-3-oxo-3-phenyl-1-propenyl]-4-[3-(5-methyl-2-phenyl-4-oxazolyl) propyl], 5-[(2,4-dioxo-5-thiazolidinyl)methyl]-2-methoxy-N-[[4-(trifluoromethyl) phenyl]methyl]-benzamide, exenatide, 8-37-glucagon-like peptide I (human)-N-[3-(1H-imidazol-4-yl)-1-oxopropyl]-26-L-arginine-34-[N6-(1-oxooctyl)-L-lysine], and vildagliptin.

6. The combination of claim 3 wherein the anti-obesity agent is at least one agent selected from the group consisting of a beta 3 adrenergic agonist, a lipase inhibitor, a serotonin reuptake inhibitor, a dopamine reuptake inhibitor, a serotonin and dopamine reuptake inhibitor, a thyroid receptor beta compound, and an anorectic agent.

7. The combination of claim 6 wherein the anti-obesity agent is at least one agent selected from the group consisting of orlistat, cetilistat, rafabregon, N-[4-[2-[[(2S)-3-[(6-amino-3-pyridinyl)oxy]-2-hydroxypropyl]amino]ethyl]phenyl]-4-(1-methylethyl)-benzenesulfonamide, sibutramine, topiramate, axokine, dexamphetamine, phentermine, pheniylpropanolamine and mazindol.

8. The combination of claim 3 wherein the lipid lowering agent is at least one agent selected from the group consisting of a microsomal triglyceride transfer protein (MTP) inhibitor, cholesterol ester transfer protein, a hydroxy-3-methyl-glutaryl-coenzyme A (HMG CoA) reductase inhibitor, a squalene synthetase inhibitor, a fibric acid derivative, an upregulator of low-density lipoprotein (LDL) receptor activity, a lipoxygenase inhibitor, or an acyl coenzyme A-cholesterol acyltransferase (ACAT) inhibitor.

9. The combination of claim 8 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate, avasimibe, N-[2,6-bis(1-methylethyl)phenyl]-2-(tetradecylthio)-acetamide, 3-(13-hydroxy-10-oxotetradecyl)-5,7-dimethoxy-1(3H)-isobenzofuranone, torcetrapib, and (3 alpha,4 alpha,5 alpha)-4-(2-propenyl-cholestan-3-ol).

10. An isolated polypeptide of claim 1 selected from the group consisting of SEQ ID NOs: 456-468.

11. An isolated polypeptide selected from the group consisting of SEQ ID NOs: 456-468.

12. A pharmaceutical composition comprising a polypeptide of claim 11 and a pharmaceutically acceptable carrier.

13. A pharmaceutical combination comprising a polypeptide of claim 11 and at least one therapeutic agent selected from the group consisting of an antidiabetic agent, an anti-obesity agent, an anti-hypertensive agent, an anti-atherosclerotic agent and a lipid-lowering agent.

14. The combination of claim 13 wherein the antidiabetic agent is at least one agent selected from the group consisting of a biguanide, a sulfonyl urea, a glucosidase inhibitor, a peroxisome proliferator-activated receptor (PPAR) γ agonist, PPAR α/γ dual agonist, an adipocyte lipid binding protein (aP2) inhibitor, a dipeptidyl peptidase 4 (DP4) inhibitor, an insulin sensitizer, a glucagon-like peptide-I (GLP-I), insulin and a meglitinide.

15. The combination of claim 14 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, fargiltizar, isaglitazone, reglitizar, balaglitazone, (Z)-1,4-bis{4-[(3,5-Dioxo-1,2,4-oxadiazolidin-2-yl)methyl]phenoxy}but-2-ene, rivoglitazone, rafaegron, repaglinide, nateglinide, (S)-2-benzyl-4-oxo-4-(cis-perhydroisoindol-2yl)butyric acid calcium salt, tesaglitizar, L-phenylalanine,N-[(1Z)-1-methyl-3-oxo-3-phenyl-1-propenyl]-4-[3-(5-methyl-2-phenyl-4-oxazolyl) propyl], 5-[(2,4-dioxo-5-thiazolidinyl)methyl]-2-methoxy-N-[[4-(trifluoromethyl)phenyl]methyl]-benzamide, exenatide, 8-37-glucagon-like peptide I (human)-N-[3-(1H-imidazol-4-yl)-1-oxopropyl]-26-L-arginine-34-[N6-(1-oxooctyl)-L-lysine], and vildagliptin.

16. The combination of claim 13 wherein the anti-obesity agent is at least one agent selected from the group consisting of a beta 3 adrenergic agonist, a lipase inhibitor, a serotonin reuptake inhibitor, a dopamine reuptake inhibitor, a serotonin and dopamine reuptake inhibitor, a thyroid receptor beta compound, and an anorectic agent.

17. The combination of claim 16 wherein the anti-obesity agent is at least one agent selected from the group consisting of orlistat, cetilistat, rafabregon, N-[4-[2-[[(2S)-3-[(6-amino-3-pyridinyl)oxy]-2-hydroxypropyl]amino]ethyl]phenyl]-4-(1-methylethyl)-benzenesulfonamide, sibutramine, topiramate, axokine, dexamphetamine, phentermine, phenylprapanolamine and mazindol.

18. The combination of claim 13 wherein the lipid lowering agent is at least one agent selected from the group consisting of a microsomal triglyceride transfer protein (MTP) inhibitor, cholesterol ester transfer protein, a hydroxy-3-methyl-glutaryl-coenzyme A (HMG CoA) reductase inhibitor, a squalene synthetase inhibitor, a trio acid derivative, an upregulator of low-density lipoprotein (LDL) receptor activity, a lipoxygenase inhibitor, or an acyl coenzyme A-cholesterol acyltransferase (ACAT) inhibitor.

19. The combination of claim 18 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate, avasimibe, N-[2,6-bis(1-methylethyl)phenyl]-2-(tetradecylthio)-acetamide, 3-(13-hydroxy-10-oxotetradecyl)-5,7-dimethoxy-1(3H)-isobenzofuranone, torcetrapib, and (3 alpha,4 alpha,5 alpha)-4-(2-propenylcholestan-3-ol).

* * * * *

UNITED STATES PATENT AND TRADEMARK OFFICE
CERTIFICATE OF CORRECTION

| | | |
|---|---|---|
| PATENT NO. | : 7,238,671 B2 | Page 1 of 224 |
| APPLICATION NO. | : 10/419399 | |
| DATED | : July 3, 2007 | |
| INVENTOR(S) | : Sesha Iyer Natarajan et al. | |

It is certified that error appears in the above-identified patent and that said Letters Patent is hereby corrected as shown below:

At column 37/38, under the "Table I" heading, insert -- The peptide sequences listed below contain a free amino group at the N-terminus and a carboximide at the C-terminus. The amino acids shown in Table I – IV are contiguous --

At column 57/58, under the "Table II" heading, insert -- The peptides listed below are carboximide at the C-terminus. --

At column 59/60, under the Table III" heading, insert

-- 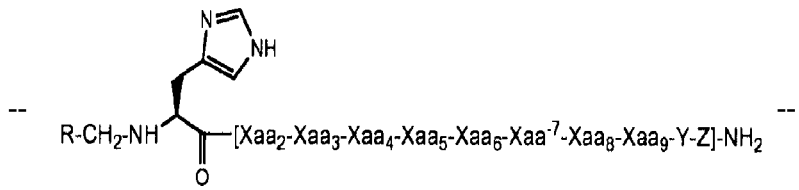 --

At column 59/60, as a footnote to Table III, insert -- *All of the compounds in Table III were prepared as C-terminal carboxamides. --

UNITED STATES PATENT AND TRADEMARK OFFICE
CERTIFICATE OF CORRECTION

PATENT NO.       : 7,238,671 B2
APPLICATION NO.  : 10/419399
DATED            : July 3, 2007
INVENTOR(S)      : Sesha Iyer Natarajan et al.

It is certified that error appears in the above-identified patent and that said Letters Patent is hereby corrected as shown below:

At column 71/72, delete the incorrect sequence listing and insert the correct sequence listing as follows:

--

```
                       SEQUENCE LISTING

<110>   Bristol-Myers Squibb Company
        Natarajan, Sesha I
        Mapelli, Claudio
        Bastos, Margarita M
        Bernatowicz, Michael
        Lee, Ving G
        Ewing, William R <120>   HUMAN GLUCAGON-LIKE PEPTIDE-1 MIMICS AND THEIR USE IN THE
        TREATMENT OF DIABETES AND RELATED CONDITIONS

<130>   D0103A CIP

<140>   10/419,399
<141>   2003-04-21

<150>   US 60/342,015
<151>   2001-10-18

<150>   US 10/273,975
<151>   2002-10-18

<160>   469

<170>   PatentIn version 3.3

<210>   1
<211>   11
<212>   PRT
<213>   Artificial Sequence

<220>
<223>   Synthetic Peptide

<220>
<221>   MISC_FEATURE
<222>   (10)..(10)
<223>   X is biphenylalanine
```

```
<220>
<221>  MISC_FEATURE
<222>  (11)..(11)
<223>  Phe is Phe(4-NO2)

<400>  1

His Ala Glu Gly Thr Phe Thr Ser Asp Xaa Phe
1               5                   10

<210>  2
<211>  11
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
<223>  X is 2-Nal

<400>  2

His Ala Glu Gly Thr Phe Thr Ser Asp Xaa Xaa
1               5                   10

<210>  3
<211>  11
<212>  PRT
<213>  Artificial Sequence

<220>
<223>  Synthetic Peptide

<220>
<221>  MISC_FEATURE
<222>  (10)..(11)
<223>  X is biphenylalanine

<400>  3

His Ala Glu Gly Thr Phe Thr Ser Asp Xaa Xaa
1               5                   10

<210>  4
<211>  11
```

```
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(penta-Fluoro)

<400>   4

His Ala Glu Gly Thr Phe Thr Ser Asp Xaa Phe
1               5                   10

<210>   5
<211>   11
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(4-Me)

<400>   5

His Ala Glu Gly Thr Phe Thr Ser Asp Xaa Phe
1               5                   10

<210>   6
<211>   11
<212>   PRT
<213>   Artificial Sequence

<220>
<223>   Synthetic Peptide

<220>
<221>   MISC_FEATURE
```

```
<222>   (10)..(10)
<223>   X is 2-Nal

<220>
<221>   MISC_FEATURE
<222>   (11)..(11)
<223>   X is biphenylalanine

<400>   6

His Ala Glu Gly Thr Phe Thr Ser Asp Xaa Xaa
1               5                   10

<210>   7
<211>   11
<212>   PRT
<213>   Artificial Sequence

<220>
<223>   Synthetic Peptide

<220>
<221>   MISC_FEATURE
<222>   (10)..(10)
<223>   X is biphenylalanine

<400>   7

His Ala Glu Gly Thr Phe Thr Ser Asp Xaa Phe
1               5                   10

<210>   8
<211>   11
<212>   PRT
<213>   Artificial Sequence

<220>
<223>   Synthetic Peptide

<220>
<221>   MISC_FEATURE
<222>   (10)..(10)
<223>   X is biphenylalanine

<400>   8

His Ala Glu Gly Thr Phe Thr Ser Asp Xaa Tyr
1               5                   10

<210>   9
<211>   11
<212>   PRT
<213>   Artificial Sequence
```

```
<220>
<223>   Synthetic Peptide

<220>
<221>   MISC_FEATURE
<222>   (10)..(10)
<223>   X is 2-Nal

<220>
<221>   MISC_FEATURE
<222>   (11)..(11)
<223>   Phe is Phe(penta-Fluoro)

<400>   9

His Ala Glu Gly Thr Phe Thr Ser Asp Xaa Phe
1               5                   10

<210>   10
<211>   11
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(4-Iodo)

<400>   10

His Ala Glu Gly Thr Phe Thr Ser Asp Xaa Phe
1               5                   10

<210>   11
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)
```

```
<220>
<221>  MISC_FEATURE
<222>  (11)..(11)
<223>  X is biphenylalanine(4-OMe)

<400>  11

His Ala Glu Gly Thr Phe Thr Ser Asp Xaa Xaa
1               5                   10

<210>  12
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(3,4-Methylenedioxy)

<400>  12

His Ala Glu Gly Thr Phe Thr Ser Asp Xaa Xaa
1               5                   10

<210>  13
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  Phe is 4-(1-Naphthyl)-Phe

<400>  13

His Ala Glu Gly Thr Phe Thr Ser Asp Xaa Phe
1               5                   10
```

```
<210>  14
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(4-Me)

<400>  14

His Ala Glu Gly Thr Phe Thr Ser Asp Xaa Xaa
1               5                   10

<210>  15
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(3-Me)

<400>  15

His Ala Glu Gly Thr Phe Thr Ser Asp Xaa Xaa
1               5                   10

<210>  16
<211>  11
<212>  PRT
<213>  Artificial Sequence

<220>
<223>  Synthetic Peptide
```

```
<220>
<221>  MISC_FEATURE
<222>  (10)..(10)
<223>  X is biphenylalanine(2,4-di-OMe)

<220>
<221>  MISC_FEATURE
<222>  (11)..(11)
<223>  X is biphenylalanine(2-Me)

<400>  16

His Ala Glu Gly Thr Phe Thr Ser Asp Xaa Xaa
1               5                   10

<210>  17
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me, 4-OMe)

<220>
<221>  MISC_FEATURE
<222>  (11)..(11)
<223>  X is biphenylalanine(2-Me)

<400>  17

His Ala Glu Gly Thr Phe Thr Ser Asp Xaa Xaa
1               5                   10

<210>  18
<211>  11
<212>  PRT
<213>  Artificial Sequence

<220>
<223>  Synthetic Peptide

<220>
<221>  MISC_FEATURE
<222>  (10)..(11)
<223>  X is biphenylalanine(2-Me)

<400>  18
```

```
His Ala Asp Gly Thr Phe Thr Ser Asp Xaa Xaa
1               5                   10

<210>   19
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (10)..(11)
<223>   X is biphenylalanine(2-Me)

<400>   19

His Ala Glu Gly Leu Phe Thr Ser Asp Xaa Xaa
1               5                   10

<210>   20
<211>   11
<212>   PRT
<213>   Artificial Sequence

<220>
<223>   Synthetic Peptide

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   20

His Ala Glu Gly Thr Phe Thr Ser Asp Xaa Xaa
1               5                   10

<210>   21
<211>   11
<212>   PRT
<213>   Artificial Sequence
```

```
<220>
<223>  Synthetic Peptide

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  21

His Ala His Gly Thr Phe Thr Ser Asp Xaa Xaa
1               5                   10

<210>  22
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (10)..(11)
<223>  X is biphenylalanine(2-Me)

<400>  22

His Ala Asp Gly Leu Phe Thr Ser Asp Xaa Xaa
1               5                   10

<210>  23
<211>  11
<212>  PRT
<213>  Artificial Sequence

<220>
<223>  Synthetic Peptide

<220>
<221>  MOD_RES
<222>  (5)..(5)
```

```
<223>   Nle

<220>
<221>   MISC_FEATURE
<222>   (10)..(11)
<223>   X is biphenylalanine(2-Me)

<400>   23

His Ala Glu Gly Leu Phe Thr Ser Asp Xaa Xaa
1               5                   10

<210>   24
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (10)..(11)
<223>   X is biphenylalanine(2-Me)

<400>   24

His Ala Glu Gly Leu Phe Thr His Asp Xaa Xaa
1               5                   10

<210>   25
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (10)..(11)
<223>   X is biphenylalanine(2-Me)

<400>   25
```

```
His Ala Asp Gly Leu Phe Thr Ser Asp Xaa Xaa
1               5                   10

<210>   26
<211>   11
<212>   PRT
<213>   Artificial Sequence

<220>
<223>   Synthetic Peptide

<220>
<221>   MISC_FEATURE
<222>   (6)..(6)
<223>   Phe is phe(penta-Fluoro)

<220>
<221>   MISC_FEATURE
<222>   (10)..(11)
<223>   X is biphenylalanine(2-Me)

<400>   26

His Ala Asp Gly Thr Phe Thr Ser Asp Xaa Xaa
1               5                   10

<210>   27
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   27

His Ala His Gly Leu Phe Thr Ser Asp Xaa Xaa
1               5                   10
```

```
<210>   28
<211>   11
<212>   PRT
<213>   Artificial Sequence

<220>
<223>   Synthetic Peptide

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   28

His Ala His Gly Thr Phe Thr His Asp Xaa Xaa
1               5                   10

<210>   29
<211>   11
<212>   PRT
<213>   Artificial Sequence

<220>
<223>   Synthetic Peptide

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   29

His Ala Asp Gly Thr Phe Thr His Asp Xaa Xaa
1               5                   10

<210>   30
<211>   11
<212>   PRT
<213>   Artificial Sequence

<220>
<223>   Synthetic Peptide
```

```
<220>
<221>  MOD_RES
<222>  (5)..(5)
<223>  Nle

<220>
<221>  MISC_FEATURE
<222>  (10)..(11)
<223>  X is biphenylalanine(2-Me)

<400>  30

His Ala Asp Gly Leu Phe Thr His Asp Xaa Xaa
1               5                   10

<210>  31
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  31

His Ala Asp Gly Leu Phe Thr Ser Asp Xaa Xaa
1               5                   10

<210>  32
<211>  11
<212>  PRT
<213>  Artificial Sequence

<220>
<223>  Synthetic Peptide

<220>
<221>  MISC_FEATURE
<222>  (10)..(10)
```

```
<223>   X is biphenylalanine(2-Et)

<220>
<221>   MISC_FEATURE
<222>   (11)..(11)
<223>   X is biphenylalanine

<400>   32

His Ala Glu Gly Thr Phe Thr Ser Asp Xaa Xaa
1               5                   10

<210>   33
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (10)..(11)
<223>   X is biphenylalanine(2-Me)

<400>   33

His Ala Glu Gly Leu Phe Thr His Asp Xaa Xaa
1               5                   10

<210>   34
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-OEt)

<220>
<221>   MISC_FEATURE
<222>   (11)..(11)
<223>   X is biphenylalanine(2-Me)

<400>   34
```

```
His Ala Glu Gly Thr Phe Thr Ser Asp Xaa Xaa
1               5                   10

<210>   35
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Propyl)

<220>
<221>   MISC_FEATURE
<222>   (11)..(11)
<223>   X is biphenylalanine(2-Me)

<400>   35

His Ala Glu Gly Thr Phe Thr Ser Asp Xaa Xaa
1               5                   10

<210>   36
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Propyl, 4-OMe)

<220>
<221>   MISC_FEATURE
<222>   (11)..(11)
<223>   X is biphenylalanine(2-Me)

<400>   36

His Ala Glu Gly Thr Phe Thr Ser Asp Xaa Xaa
1               5                   10

<210>   37
<211>   11
<212>   PRT
<213>   Artificial Sequence
```

```
<220>
<223>   Synthetic Peptide

<220>
<221>   MISC_FEATURE
<222>   (10)..(10)
<223>   X is biphenylalanine(2-Trifluoromethyl)

<220>
<221>   MISC_FEATURE
<222>   (11)..(11)
<223>   X is biphenylalanine

<400>   37

His Ala Glu Gly Thr Phe Thr Ser Asp Xaa Xaa
1               5                   10

<210>   38
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Chloro)

<220>

<221>   MISC_FEATURE
<222>   (11)..(11)
<223>   X is Biphenylalanine

<400>   38

His Ala Glu Gly Thr Phe Thr Ser Asp Xaa Xaa
1               5                   10

<210>   39
<211>   11
<212>   PRT
<213>   Artificial Sequence

<220>
<223>   Synthetic Peptide

<220>
<221>   MISC_FEATURE
<222>   (10)..(10)
```

```
<223>   X is biphenylalanine(4-Fluoro)

<220>
<221>   MISC_FEATURE
<222>   (11)..(11)
<223>   X is biphenylalanine

<400>   39

His Ala Glu Gly Thr Phe Thr Ser Asp Xaa Xaa
1               5                   10

<210>   40
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-Trifluoromethyl)

<220>
<221>   MISC_FEATURE
<222>   (11)..(11)
<223>   X is biphenylalanine

<400>   40

His Ala Glu Gly Thr Phe Thr Ser Asp Xaa Xaa
1               5                   10

<210>   41
<211>   11
<212>   PRT
<213>   Artificial Sequence

<220>
<223>   Synthetic Peptide

<220>
<221>   MISC_FEATURE
<222>   (10)..(10)
<223>   X is 4-(1-Naphtyl)-Phe

<220>
<221>   MISC_FEATURE
<222>   (11)..(11)
<223>   X is biphenylalanine

<400>   41
```

```
His Ala Glu Gly Thr Phe Thr Ser Asp Xaa Xaa
1               5                   10

<210>   42
<211>   11
<212>   PRT
<213>   Artificial Sequence

<220>
<223>   Synthetic Peptide

<220>
<221>   MISC_FEATURE
<222>   (10)..(10)
<223>   X is 4-(3-thiophene)-Phe

<220>
<221>   MISC_FEATURE
<222>   (11)..(11)
<223>   X is biphenylalanine

<400>   42

His Ala Glu Gly Thr Phe Thr Ser Asp Xaa Xaa
1               5                   10

<210>   43
<211>   11
<212>   PRT
<213>   Artificial Sequence

<220>
<223>   Synthetic Peptide

<220>
<221>   MISC_FEATURE
<222>   (10)..(10)
<223>   X is 4-(3-Quinoline)-Phe

<220>
<221>   MISC_FEATURE
<222>   (11)..(11)
<223>   X is biphenylalanine

<400>   43

His Ala Glu Gly Thr Phe Thr Ser Asp Xaa Xaa
1               5                   10

<210>   44
<211>   11
<212>   PRT
<213>   Artificial Sequence
```

```
<220>
<223>    Synthetic Peptide

<220>
<221>    MISC_FEATURE
<222>    (10)..(10)
<223>    X is Biphenylalanine(2-Me)

<220>
<221>    MISC_FEATURE
<222>    (11)..(11)
<223>    Phe is Phe(penta-Fluoro)

<400>    44

His Ala Glu Gly Thr Phe Thr Ser Asp Xaa Phe
1               5                   10

<210>    45
<211>    11
<212>    PRT
<213>    Artificial Sequence

<220>
<223>    Synthetic Peptide

<220>
<221>    MISC_FEATURE
<222>    (10)..(10)
<223>    X is biphenylalanine(2-OMe)

<220>
<221>    MISC_FEATURE
<222>    (11)..(11)
<223>    Phe is Phe(penta-Fluoro)

<400>    45

His Ala Glu Gly Thr Phe Thr Ser Asp Xaa Phe
1               5                   10

<210>    46
<211>    11
<212>    PRT
<213>    Artificial Sequence

<220>
<223>    Synthetic Peptide

<220>
<221>    MISC_FEATURE
<222>    (10)..(10)
<223>    X is Biphenylalanine(2-Trifluoromethyl)
```

```
<220>
<221>  MISC_FEATURE
<222>  (11)..(11)
<223>  Phe is Phe(penta-Fluoro)

<400>  46

His Ala Glu Gly Thr Phe Thr Ser Asp Xaa Phe
1               5                   10

<210>  47
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Trifluoromethyl)

<220>
<221>  MISC_FEATURE
<222>  (11)..(11)
<223>  Phe is Phe(penta-Fluoro)

<400>  47

His Ala Glu Gly Thr Phe Thr Ser Asp Xaa Phe
1               5                   10

<210>  48
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Chloro)

<220>
<221>  MISC_FEATURE
<222>  (11)..(11)
<223>  Phe is Phe(penta-Fluoro)

<400>  48

His Ala Glu Gly Thr Phe Thr Ser Asp Xaa Phe
1               5                   10
```

```
<210>  49
<211>  11
<212>  PRT
<213>  Artificial Sequence

<220>
<223>  Synthetic Peptide

<220>
<221>  MISC_FEATURE
<222>  (10)..(10)
<223>  X is Biphenylalanine(2-Fluoro)

<220>
<221>  MISC_FEATURE
<222>  (11)..(11)
<223>  Phe is Phe(penta-Fluoro)

<400>  49

His Ala Glu Gly Thr Phe Thr Ser Asp Xaa Phe
1               5                   10

<210>  50
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(4-OMe)

<220>
<221>  MISC_FEATURE
<222>  (11)..(11)
<223>  Phe is Phe(penta-Fluoro)

<400>  50

His Ala Glu Gly Thr Phe Thr Ser Asp Xaa Phe
1               5                   10

<210>  51
<211>  11
<212>  PRT
<213>  Artificial Sequence

<220>
<223>  Synthetic Peptide
```

```
<220>
<221>  MISC_FEATURE
<222>  (10)..(10)
<223>  X is biphenylalanine(3,4-Methylenedioxy)

<220>
<221>  MISC_FEATURE
<222>  (11)..(11)
<223>  Phe is Phe(penta-Fluoro)

<400>  51

His Ala Glu Gly Thr Phe Thr Ser Asp Xaa Phe
1               5                   10

<210>  52
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is 2-Nal

<400>  52

His Ala Glu Gly Thr Phe Thr Ser Asp Xaa Xaa
1               5                   10

<210>  53
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-OMe)

<220>
<221>  MISC_FEATURE
```

```
<222>   (11)..(11)
<223>   X is 2-Nal

<400>   53

His Ala Glu Gly Thr Phe Thr Ser Asp Xaa Xaa
1               5                   10

<210>   54
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Trifluoromethyl)

<220>
<221>   MISC_FEATURE
<222>   (11)..(11)
<223>   X is 2-Nal

<400>   54

His Ala Glu Gly Thr Phe Thr Ser Asp Xaa Xaa
1               5                   10

<210>   55
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Chloro)

<220>
<221>   MISC_FEATURE
<222>   (11)..(11)
<223>   X is 2-Nal

<400>   55

His Ala Glu Gly Thr Phe Thr Ser Asp Xaa Xaa
1               5                   10
```

```
<210>  56
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Fluoro)

<220>
<221>  MISC_FEATURE
<222>  (11)..(11)
<223>  X is 2-Nal

<400>  56

His Ala Glu Gly Thr Phe Thr Ser Asp Xaa Xaa
1               5                   10

<210>  57
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(4-Me)

<220>
<221>  MISC_FEATURE
<222>  (11)..(11)
<223>  X is 2-Nal

<400>  57

His Ala Glu Gly Thr Phe Thr Ser Asp Xaa Xaa
1               5                   10

<210>  58
<211>  11
<212>  PRT
<213>  Artificial Sequence

<220>
<223>  Synthetic Peptide
```

```
<220>
<221>   MISC_FEATURE
<222>   (10)..(10)
<223>   X is biphenylalanine(4-OMe)

<220>
<221>   MISC_FEATURE
<222>   (11)..(11)
<223>   X is 2-Nal

<400>   58

His Ala Glu Gly Thr Phe Thr Ser Asp Xaa Xaa
1               5                   10

<210>   59
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(3,4-Methylenedioxy)

<220>
<221>   MISC_FEATURE
<222>   (11)..(11)
<223>   X is 2-Nal

<400>   59

His Ala Glu Gly Thr Phe Thr Ser Asp Xaa Xaa
1               5                   10

<210>   60
<211>   11
<212>   PRT

<213>   Artificial Sequence

<220>
<223>   Synthetic Peptide

<220>
<221>   MISC_FEATURE
<222>   (10)..(10)
<223>   X is 4-(1-Naphthyl)-Phe

<220>
<221>   MISC_FEATURE
```

```
<222>   (11)..(11)
<223>   X is 2-Nal

<400>   60

His Ala Glu Gly Thr Phe Thr Ser Asp Xaa Xaa
1               5                   10

<210>   61
<211>   11
<212>   PRT
<213>   Artificial Sequence

<220>
<223>   Synthetic Peptide

<220>
<221>   MISC_FEATURE
<222>   (10)..(10)
<223>   X is 4-(3-thiophene)-Phe

<220>
<221>   MISC_FEATURE
<222>   (11)..(11)
<223>   X is 2-Nal

<400>   61

His Ala Glu Gly Thr Phe Thr Ser Asp Xaa Xaa
1               5                   10

<210>   62
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   Phe is Phe(4-Me)

<400>   62

His Ala Glu Gly Thr Phe Thr Ser Asp Xaa Phe
1               5                   10
```

```
<210>  63
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Trifluoromethyl)

<220>
<221>  MISC_FEATURE
<222>  (11)..(11)
<223>  Phe is Phe(4-Me)

<400>  63

His Ala Glu Gly Thr Phe Thr Ser Asp Xaa Phe
1               5                   10

<210>  64
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Chloro)

<220>
<221>  MISC_FEATURE
<222>  (11)..(11)
<223>  Phe is Phe(4-Me)

<400>  64

His Ala Glu Gly Thr Phe Thr Ser Asp Xaa Phe
1               5                   10

<210>  65
<211>  11
<212>  PRT
<213>  Artificial Sequence

<220>
<223>  Synthetic Peptide
```

```
<220>
<221>   MISC_FEATURE
<222>   (10)..(10)
<223>   X is biphenylalanine(2-Fluoro)

<220>
<221>   MISC_FEATURE
<222>   (11)..(11)
<223>   Phe is Phe(4-Me)

<400>   65

His Ala Glu Gly Thr Phe Thr Ser Asp Xaa Phe
1               5                   10

<210>   66
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-Chloro)

<220>
<221>   MISC_FEATURE
<222>   (11)..(11)
<223>   Phe is Phe(4-Me)

<400>   66

His Ala Glu Gly Thr Phe Thr Ser Asp Xaa Phe
1               5                   10

<210>   67
<211>   11
<212>   PRT

<213>   Artificial Sequence

<220>
<223>   Synthetic Peptide

<220>
<221>   MISC_FEATURE
<222>   (10)..(10)
<223>   X is biphenylalanine(4-Me)

<220>
<221>   MISC_FEATURE
```

```
<222>   (11)..(11)
<223>   Phe is Phe(4-Me)

<400>   67

His Ala Glu Gly Thr Phe Thr Ser Asp Xaa Phe
1               5                   10

<210>   68
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-Fluoro)

<220>
<221>   MISC_FEATURE
<222>   (11)..(11)
<223>   Phe is Phe(4-Me)

<400>   68

His Ala Glu Gly Thr Phe Thr Ser Asp Xaa Phe
1               5                   10

<210>   69
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-OMe)

<220>
<221>   MISC_FEATURE
<222>   (11)..(11)
<223>   Phe is Phe(4-Me)

<400>   69

His Ala Glu Gly Thr Phe Thr Ser Asp Xaa Phe
1               5                   10
```

```
<210>   70
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(3,4-Methylenedioxy)

<220>
<221>   MISC_FEATURE
<222>   (11)..(11)
<223>   Phe is Phe(4-Me)

<400>   70

His Ala Glu Gly Thr Phe Thr Ser Asp Xaa Phe
1               5                   10

<210>   71
<211>   11
<212>   PRT
<213>   Artificial Sequence

<220>
<223>   Synthetic Peptide

<220>
<221>   MISC_FEATURE
<222>   (10)..(10)
<223>   X is 4-(1-Naphthyl)-Phe

<220>
<221>   MISC_FEATURE
<222>   (11)..(11)
<223>   Phe is Phe(4-Me)

<400>   71

His Ala Glu Gly Thr Phe Thr Ser Asp Xaa Phe
1               5                   10

<210>   72
<211>   11
<212>   PRT
<213>   Artificial Sequence

<220>
<223>   Synthetic Peptide
```

```
<220>
<221>   MISC_FEATURE
<222>   (10)..(10)
<223>   X is biphenylalanine(3-phenyl)

<220>
<221>   MISC_FEATURE
<222>   (11)..(11)
<223>   Phe is Phe(4-Me)

<400>   72

His Ala Glu Gly Thr Phe Thr Ser Asp Xaa Phe
1               5                   10

<210>   73
<211>   11
<212>   PRT

<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(2-Fluoro)

<400>   73

His Ala Glu Gly Thr Phe Thr Ser Asp Xaa Xaa
1               5                   10

<210>   74
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
```

```
<222>  (11)..(11)
<223>  X is biphenylalanine(4-phenyl)

<400>  74

His Ala Glu Gly Thr Phe Thr Ser Asp Xaa Xaa
1               5                   10

<210>  75
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(3-OMe)

<400>  75

His Ala Glu Gly Thr Phe Thr Ser Asp Xaa Xaa
1               5                   10

<210>  76
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  Phe is 4-(3-Pyridyl)-Phe

<400>  76

His Ala Glu Gly Thr Phe Thr Ser Asp Xaa Phe
1               5                   10
```

```
<210>  77
<211>  11
<212>  PRT
<213>  Artificial Sequence

<220>
<223>  Synthetic Peptide

<220>
<221>  MISC_FEATURE
<222>  (10)..(10)
<223>  Phe is Phe(penta-Fluoro)

<220>
<221>  MISC_FEATURE
<222>  (11)..(11)
<223>  X is biphenylalanine(4-OMe)

<400>  77

His Ala Glu Gly Thr Phe Thr Ser Asp Phe Xaa
1               5                   10

<210>  78
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(3-Acetamido)

<400>  78

His Ala Glu Gly Thr Phe Thr Ser Asp Xaa Xaa
1               5                   10

<210>  79
<211>  11
<212>  PRT
<213>  Artificial Sequence

<220>
<223>  Synthetic Peptide
```

```
<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(4-Isopropyl)

<400>   79

His Ala Glu Gly Thr Phe Thr Ser Asp Xaa Xaa
1               5                   10

<210>   80
<211>   11
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is 4-(1-Naphthyl)-Phe

<400>   80

His Ala Glu Gly Thr Phe Thr Ser Asp Xaa Phe
1               5                   10

<210>   81
<211>   11
<212>   PRT
<213>   Artificial Sequence

<220>
<223>   Synthetic Peptide

<220>
<221>   MISC_FEATURE
<222>   (10)..(10)
<223>   X is Biphenylalanine

<220>
<221>   MISC_FEATURE
<222>   (11)..(11)
<223>   Phe is 4-(3-Pyridyl)-Phe
```

```
<400> 81

His Ala Glu Gly Thr Phe Thr Ser Asp Xaa Phe
1               5                   10

<210> 82
<211> 11
<212> PRT
<213> Artificial Sequence

<220>
<223> Synthetic Peptide

<220>
<221> MISC_FEATURE
<222> (10)..(10)
<223> Phe is Phe(penta-Fluoro)

<220>
<221> MISC_FEATURE
<222> (11)..(11)
<223> X is biphenylalanine(2-Me)

<400> 82

His Ala Glu Gly Thr Phe Thr Ser Asp Phe Xaa
1               5                   10

<210> 83
<211> 11
<212> PRT
<213> Artificial Sequence

<220>
<223> Synthetic Peptide

<220>
<221> MISC_FEATURE
<222> (10)..(10)
<223> X is 2-Nal

<220>
<221> MISC_FEATURE
<222> (11)..(11)
<223> X is biphenylalanine(2-Me)

<400> 83

His Ala Glu Gly Thr Phe Thr Ser Asp Xaa Xaa
1               5                   10

<210> 84
<211> 11
```

```
<212>   PRT
<213>   Artificial Sequence

<220>
<223>   Synthetic Peptide

<220>
<221>   MISC_FEATURE
<222>   (10)..(10)
<223>   Phe is Phe(4-Iodo)

<220>
<221>   MISC_FEATURE
<222>   (11)..(11)
<223>   X is biphenylalanine(2-Me)

<400>   84

His Ala Glu Gly Thr Phe Thr Ser Asp Phe Xaa
1               5                   10

<210>   85
<211>   11
<212>   PRT
<213>   Artificial Sequence

<220>
<223>   Synthetic Peptide

<220>
<221>   MISC_FEATURE
<222>   (10)..(10)
<223>   Phe is Phe(3,4-di-Chloro)

<220>
<221>   MISC_FEATURE
<222>   (11)..(11)
<223>   X is biphenylalanine(2-Me)

<400>   85

His Ala Glu Gly Thr Phe Thr Ser Asp Phe Xaa
1               5                   10

<210>   86
<211>   11
<212>   PRT

<213>   Artificial Sequence

<220>
<223>   Synthetic Peptide
```

```
<220>
<221>  MISC_FEATURE
<222>  (10)..(10)
<223>  Tyr is Tyr(Bzl)

<220>
<221>  MISC_FEATURE
<222>  (11)..(11)
<223>  X is biphenylalanine(2-Me)

<400>  86

His Ala Glu Gly Thr Phe Thr Ser Asp Tyr Xaa
1               5                   10

<210>  87
<211>  11
<212>  PRT
<213>  Artificial Sequence

<220>
<223>  Synthetic Peptide

<220>
<221>  MISC_FEATURE
<222>  (10)..(10)
<223>  Phe is homoPhe

<220>
<221>  MISC_FEATURE
<222>  (11)..(11)
<223>  X is biphenylalanine(2-Me)

<400>  87

His Ala Glu Gly Thr Phe Thr Ser Asp Phe Xaa
1               5                   10

<210>  88
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2,4-di-OMe)

<220>
<221>  MISC_FEATURE
<222>  (11)..(11)
<223>  X is biphenylalanine
```

```
<400>   88

His Ala Glu Gly Thr Phe Thr Ser Asp Xaa Xaa
1               5                   10

<210>   89
<211>   11
<212>   PRT
<213>   Artificial Sequence

<220>
<223>   Synthetic Peptide

<220>
<221>   MISC_FEATURE
<222>   (10)..(10)
<223>   Phe is 4-(4-(3,5-dimethylisoxazole))-Phe <220>
<221>   MISC_FEATURE
<222>   (11)..(11)
<223>   X is biphenylalanine

<400>   89

His Ala Glu Gly Thr Phe Thr Ser Asp Phe Xaa
1               5                   10

<210>   90
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me, 4-OMe)

<220>
<221>   MISC_FEATURE
<222>   (11)..(11)
<223>   X is biphenylalanine

<400>   90

His Ala Glu Gly Thr Phe Thr Ser Asp Xaa Xaa
1               5                   10

<210>   91
<211>   11
```

```
<212>   PRT
<213>   Artificial Sequence

<220>
<223>   Synthetic Peptide

<220>
<221>   MISC_FEATURE
<222>   (10)..(10)
<223>   X is biphenylalanine(2,6-di-Me)

<220>
<221>   MISC_FEATURE
<222>   (11)..(11)
<223>   X is biphenylalanine

<400>   91

His Ala Glu Gly Thr Phe Thr Ser Asp Xaa Xaa
1               5                   10

<210>   92
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2,4-di-Me)

<220>
<221>   MISC_FEATURE
<222>   (11)..(11)
<223>   X is biphenylalanine

<400>   92

His Ala Glu Gly Thr Phe Thr Ser Asp Xaa Xaa
1               5                   10

<210>   93
<211>   11
<212>   PRT
<213>   Artificial Sequence

<220>
<223>   Synthetic Peptide

<220>
<221>   MISC_FEATURE
```

```
<222>   (10)..(10)
<223>   X is biphenylalanine(2,3-di-Me)

<220>
<221>   MISC_FEATURE
<222>   (11)..(11)
<223>   X is biphenylalanine

<400>   93

His Ala Glu Gly Thr Phe Thr Ser Asp Xaa Xaa
1               5                   10

<210>   94
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-trifluoromethoxy)

<220>
<221>   MISC_FEATURE
<222>   (11)..(11)
<223>   X is biphenylalanine

<400>   94

His Ala Glu Gly Thr Phe Thr Ser Asp Xaa Xaa
1               5                   10

<210>   95
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-Et)

<220>
<221>   MISC_FEATURE
<222>   (11)..(11)
<223>   X is biphenylalanine

<400>   95
```

```
His Ala Glu Gly Thr Phe Thr Ser Asp Xaa Xaa
1               5                   10

<210>   96
<211>   11
<212>   PRT
<213>   Artificial Sequence

<220>
<223>   Synthetic Peptide

<220>
<221>   MISC_FEATURE
<222>   (10)..(10)
<223>   Phe is 4-(2-Naphthyl)-Phe

<220>
<221>   MISC_FEATURE
<222>   (11)..(11)
<223>   X is biphenylalanine

<400>   96

His Ala Glu Gly Thr Phe Thr Ser Asp Phe Xaa
1               5                   10

<210>   97
<211>   11
<212>   PRT
<213>   Artificial Sequence

<220>
<223>   Synthetic Peptide

<220>
<221>   MISC_FEATURE
<222>   (10)..(10)
<223>   Phe is 4-(4-Dibenzofuran)-Phe <220>
<221>   MISC_FEATURE
<222>   (11)..(11)
<223>   X is biphenylalanine

<400>   97

His Ala Glu Gly Thr Phe Thr Ser Asp Phe Xaa
1               5                   10

<210>   98
<211>   11
<212>   PRT
<213>   Artificial Sequence
```

```
<220>
<223>  Synthetic Peptide

<220>
<221>  MISC_FEATURE
<222>  (10)..(10)
<223>  X is biphenylalanine(2,6-di-OMe)

<220>
<221>  MISC_FEATURE
<222>  (11)..(11)
<223>  X is biphenylalanine(2-Me)

<400>  98

His Ala Glu Gly Thr Phe Thr Ser Asp Xaa Xaa
1               5                   10

<210>  99
<211>  11
<212>  PRT
<213>  Artificial Sequence

<220>
<223>  Synthetic Peptide

<220>
<221>  MISC_FEATURE
<222>  (10)..(10)
<223>  Phe is 4-(2,4-dimethoxypyrimidine)-Phe <220>
<221>  MISC_FEATURE
<222>  (11)..(11)
<223>  X is biphenylalanine(2-Me)

<400>  99

His Ala Glu Gly Thr Phe Thr Ser Asp Phe Xaa
1               5                   10

<210>  100
<211>  11
<212>  PRT
<213>  Artificial Sequence

<220>
<223>  Synthetic Peptide

<220>
<221>  MISC_FEATURE
<222>  (10)..(10)
```

```
<223>   X is biphenylalanine(2,4,6-Trimethyl)

<220>
<221>   MISC_FEATURE
<222>   (11)..(11)
<223>   X is biphenylalanine(2-Me)

<400>   100

His Ala Glu Gly Thr Phe Thr Ser Asp Xaa Xaa
1               5                   10

<210>   101

<211>   11
<212>   PRT
<213>   Artificial Sequence

<220>
<223>   Synthetic Peptide

<220>
<221>   MISC_FEATURE
<222>   (10)..(10)
<223>   Phe is 4-(4-(3,5-dimethylisoxazole))-Phe <220>
<221>   MISC_FEATURE
<222>   (11)..(11)
<223>   X is biphenylalanine(2-Me)

<400>   101

His Ala Glu Gly Thr Phe Thr Ser Asp Phe Xaa
1               5                   10

<210>   102
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2,4-di-Chloro)

<220>
<221>   MISC_FEATURE
<222>   (11)..(11)
<223>   X is biphenylalanine(2-Me)
```

```
<400>  102

His Ala Glu Gly Thr Phe Thr Ser Asp Xaa Xaa
1               5                   10

<210>  103
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2,6-di-Me)

<220>
<221>  MISC_FEATURE
<222>  (11)..(11)
<223>  X is biphenylalanine(2-Me)

<400>  103

His Ala Glu Gly Thr Phe Thr Ser Asp Xaa Xaa
1               5                   10

<210>  104
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2,4-di-Me)

<220>
<221>  MISC_FEATURE
<222>  (11)..(11)
<223>  X is biphenylalanine(2-Me)

<400>  104

His Ala Glu Gly Thr Phe Thr Ser Asp Xaa Xaa
1               5                   10

<210>  105
<211>  11
<212>  PRT
```

```
<213>  Artificial Sequence

<220>
<223>  Synthetic Peptide

<220>
<221>  MISC_FEATURE
<222>  (10)..(10)
<223>  X is biphenylalanine(2,3-di-Me)

<220>
<221>  MISC_FEATURE
<222>  (11)..(11)
<223>  X is biphenylalanine(2-Me)

<400>  105

His Ala Glu Gly Thr Phe Thr Ser Asp Xaa Xaa
1               5                   10

<210>  106
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(4-Et)

<220>
<221>  MISC_FEATURE
<222>  (11)..(11)
<223>  X is biphenylalanine(4-Me)

<400>  106

His Ala Glu Gly Thr Phe Thr Ser Asp Xaa Xaa
1               5                   10

<210>  107
<211>  11
<212>  PRT
<213>  Artificial Sequence

<220>
<223>  Synthetic Peptide

<220>
<221>  MISC_FEATURE
<222>  (10)..(10)
```

```
<223>   X is biphenylalanine(4-SMe)

<220>
<221>   MISC_FEATURE
<222>   (11)..(11)
<223>   X is biphenylalanine(2-Me)

<400>   107

His Ala Glu Gly Thr Phe Thr Ser Asp Xaa Xaa
1               5                   10

<210>   108
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-OEt)

<220>
<221>   MISC_FEATURE
<222>   (11)..(11)
<223>   X is biphenylalanine(2-Me)

<400>   108

His Ala Glu Gly Thr Phe Thr Ser Asp Xaa Xaa
1               5                   10

<210>   109
<211>   11
<212>   PRT
<213>   Artificial Sequence

<220>
<223>   Synthetic Peptide

<220>
<221>   MISC_FEATURE
<222>   (10)..(10)
<223>   Phe is 4-(2-Naphthyl)-Phe

<220>
<221>   MISC_FEATURE
<222>   (11)..(11)
<223>   X is biphenylalanine(2-Me)

<400>   109
```

```
His Ala Glu Gly Thr Phe Thr Ser Asp Phe Xaa
1               5                   10

<210>   110
<211>   11
<212>   PRT
<213>   Artificial Sequence

<220>
<223>   Synthetic Peptide

<220>
<221>   MISC_FEATURE
<222>   (10)..(10)
<223>   Phe is 4-(2-Benzo(b)thiophene)-Phe <220>
<221>   MISC_FEATURE
<222>   (11)..(11)
<223>   X is biphenylalanine(2-Me)

<400>   110

His Ala Glu Gly Thr Phe Thr Ser Asp Phe Xaa
1               5                   10

<210>   111
<211>   11
<212>   PRT
<213>   Artificial Sequence

<220>
<223>   Synthetic Peptide

<220>
<221>   MISC_FEATURE
<222>   (10)..(10)
<223>   Phe is 4-(2-Benzo(b)furan)-Phe <220>
<221>   MISC_FEATURE
<222>   (11)..(11)
<223>   X is biphenylalanine(2-Me)

<400>   111

His Ala Glu Gly Thr Phe Thr Ser Asp Phe Xaa
1               5                   10

<210>   112
<211>   11
<212>   PRT
<213>   Artificial Sequence
```

```
<220>
<223>  Synthetic Peptide

<220>
<221>  MISC_FEATURE
<222>  (10)..(10)

<223>  Phe is 4-(4-Dibenzofuran)-Phe

<220>
<221>  MISC_FEATURE
<222>  (11)..(11)
<223>  X is biphenylalanine(2-Me)

<400>  112

His Ala Glu Gly Thr Phe Thr Ser Asp Phe Xaa
1               5                   10

<210>  113
<211>  11
<212>  PRT
<213>  Artificial Sequence

<220>
<223>  Synthetic Peptide

<220>
<221>  MISC_FEATURE
<222>  (10)..(10)
<223>  Phe is 4-(4-phenoxathiin)-Phe <220>
<221>  MISC_FEATURE
<222>  (11)..(11)
<223>  X is biphenylalanine(2-Me)

<400>  113

His Ala Glu Gly Thr Phe Thr Ser Asp Phe Xaa
1               5                   10

<210>  114
<211>  11
<212>  PRT
<213>  Artificial Sequence

<220>
<223>  Synthetic Peptide

<220>
<221>  MISC_FEATURE
<222>  (10)..(10)
```

```
<223>   X is biphenylalanine(2-Me)

<220>
<221>   MISC_FEATURE
<222>   (11)..(11)
<223>   X is biphenylalanine(4-Et)

<400>   114

His Ala Glu Gly Thr Phe Thr Ser Asp Xaa Xaa
1               5                   10

<210>   115
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(4-SMe)

<400>   115

His Ala Glu Gly Thr Phe Thr Ser Asp Xaa Xaa
1               5                   10

<210>   116
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(2,4-di-Me)
```

```
<400>  116

His Ala Glu Gly Thr Phe Thr Ser Asp Xaa Xaa
1               5                   10

<210>  117
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(2-Me, 4-OMe)

<400>  117

His Ala Glu Gly Thr Phe Thr Ser Asp Xaa Xaa
1               5                   10

<210>  118
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(2,3-di-Me)

<400>  118

His Ala Glu Gly Thr Phe Thr Ser Asp Xaa Xaa
1               5                   10

<210>  119
<211>  11
<212>  PRT
```

```
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   Phe is 4-(2-naphthyl)-Phe

<400>   119

His Ala Glu Gly Thr Phe Thr Ser Asp Xaa Phe
1               5                   10

<210>   120
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(2-OEt)

<400>   120

His Ala Glu Gly Thr Phe Thr Ser Asp Xaa Xaa
1               5                   10

<210>   121
<211>   11
<212>   PRT
<213>   Artificial Sequence

<220>
<223>   Synthetic Peptide

<220>
<221>   MISC_FEATURE
<222>   (10)..(10)
```

```
<223>   X is biphenylalanine(2-Me)

<220>
<221>   MISC_FEATURE
<222>   (11)..(11)
<223>   X is biphenylalanine(2-Et, 4-OMe)

<400>   121

His Ala Glu Gly Thr Phe Thr Ser Asp Xaa Xaa
1               5                   10

<210>   122
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(3-Et)

<400>   122

His Ala Glu Gly Thr Phe Thr Ser Asp Xaa Xaa
1               5                   10

<210>   123
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(3-Propyl)

<400>   123
```

```
His Ala Glu Gly Thr Phe Thr Ser Asp Xaa Xaa
1               5                   10
```

<210> 124
<211> 11
<212> PRT
<213> Artificial Sequence

<220>
<223> Synthetic Peptide

<220>
<221> MISC_FEATURE
<222> (10)..(10)
<223> X is biphenylalanine(2-Et)

<220>
<221> MISC_FEATURE
<222> (11)..(11)
<223> X is biphenylalanine(3-phenyl)

<400> 124

```
His Ala Glu Gly Thr Phe Thr Ser Asp Xaa Xaa
1               5                   10
```

<210> 125
<211> 11
<212> PRT
<213> Artificial Sequence

<220>
<223> Synthetic Peptide

<220>
<221> MISC_FEATURE
<222> (10)..(10)
<223> X is biphenylalanine(2-Et)

<220>
<221> MISC_FEATURE
<222> (11)..(11)
<223> X is biphenylalanine(3-OEt)

<400> 125

```
His Ala Glu Gly Thr Phe Thr Ser Asp Xaa Xaa
1               5                   10
```

<210> 126
<211> 11
<212> PRT
<213> Artificial Sequence

```
<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(4-Et)

<400>  126

His Ala Glu Gly Thr Phe Thr Ser Asp Xaa Xaa
1               5                   10

<210>  127
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(4-SMe)

<400>  127

His Ala Glu Gly Thr Phe Thr Ser Asp Xaa Xaa
1               5                   10

<210>  128
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)
```

```
<220>
<221>  MISC_FEATURE
<222>  (11)..(11)
<223>  X is biphenylalanine(4-OCF3)

<400>  128

His Ala Glu Gly Thr Phe Thr Ser Asp Xaa Xaa
1               5                   10

<210>  129
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(4-OEt)

<400>  129

His Ala Glu Gly Thr Phe Thr Ser Asp Xaa Xaa
1               5                   10

<210>  130
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me, 4-OMe)

<400>  130

His Ala Glu Gly Thr Phe Thr Ser Asp Xaa Xaa
```

```
<210>   131
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2,6-di-Me)

<400>   131

His Ala Glu Gly Thr Phe Thr Ser Asp Xaa Xaa
1               5                   10

<210>   132
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2,4,6-tri-Me)

<400>   132

His Ala Glu Gly Thr Phe Thr Ser Asp Xaa Xaa
1               5                   10

<210>   133
<211>   11
<212>   PRT
<213>   Artificial Sequence

<220>
```

```
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-phenyl)

<400>   133

His Ala Glu Gly Thr Phe Thr Ser Asp Xaa Xaa
1               5                   10

<210>   134
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Isopropyl)

<400>   134

His Ala Glu Gly Thr Phe Thr Ser Asp Xaa Xaa
1               5                   10

<210>   135
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
```

```
<221>  MISC_FEATURE
<222>  (11)..(11)
<223>  Phe is 4-(2-naphthyl)-Phe

<400>  135

His Ala Glu Gly Thr Phe Thr Ser Asp Xaa Phe
1               5                   10

<210>  136
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2,5-di-OMe)

<400>  136

His Ala Glu Gly Thr Phe Thr Ser Asp Xaa Xaa
1               5                   10

<210>  137
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-OEt)

<400>  137

His Ala Glu Gly Thr Phe Thr Ser Asp Xaa Xaa
1               5                   10
```

```
<210>   138
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(3,4-di-OMe)

<400>   138

His Ala Glu Gly Thr Phe Thr Ser Asp Xaa Xaa
1               5                   10

<210>   139
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Et, 4-OMe)

<400>   139

His Ala Glu Gly Thr Phe Thr Ser Asp Xaa Xaa
1               5                   10

<210>   140
<211>   11
<212>   PRT
<213>   Artificial Sequence

<220>
<223>   Synthetic Peptide
```

```
<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  140

His Ala Glu Gly Leu Phe Thr Ser Asp Xaa Xaa
1               5                   10

<210>  141
<211>  11
<212>  PRT
<213>  Artificial Sequence

<220>
<223>  Synthetic Peptide

<220>
<221>  MISC_FEATURE
<222>  (10)..(11)
<223>  X is biphenylalanine(2-Me)

<400>  141

His Ala His Gly Thr Phe Thr His Asp Xaa Xaa
1               5                   10

<210>  142
<211>  11
<212>  PRT
<213>  Artificial Sequence

<220>
<223>  Synthetic Peptide

<220>
<221>  MISC_FEATURE
<222>  (10)..(11)
<223>  X is biphenylalanine(2-Me)

<400>  142

His Ala His Gly Thr Phe Thr Ser Asp Xaa Xaa
```

```
<210>   143
<211>   11
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(4-Trifluoromethyl)

<400>   143

His Ala Glu Gly Thr Phe Thr Ser Asp Xaa Phe
1               5                   10

<210>   144
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MOD_RES
<222>   (5)..(5)
<223>   Nle

<220>

<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)
```

```
<220>
<221>  MISC_FEATURE
<222>  (11)..(11)
<223>  X is biphenylalanine(2-Me)

<400>  144

His Xaa Glu Gly Leu Phe Thr Ser Asp Xaa Xaa
1               5                   10

<210>  145
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  145

His Xaa Asp Gly Thr Phe Thr Ser Asp Xaa Xaa
1               5                   10

<210>  146
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle
```

```
<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  146

His Xaa Asp Gly Leu Phe Thr His Asp Xaa Xaa
1               5                   10

<210>  147
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is Phe(penta-Fluoro)

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  147

His Xaa His Gly Thr Phe Thr His Asp Xaa Xaa
1               5                   10

<210>  148
<211>  11
<212>  PRT
<213>  Artificial Sequence

<220>
<223>  Synthetic Peptide
```

```
<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  148

His Xaa Asp Gly Leu Phe Thr Ser Asp Xaa Xaa
1               5                   10

<210>  149
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  149

His Xaa His Gly Thr Phe Thr His Asp Xaa Xaa
1               5                   10

<210>  150
```

```
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
<223>  Phe is phe(penta-Fluoro)

<220>
<221>  MISC_FEATURE
<222>  (10)..(11)
<223>  X is biphenylalanine(2-Me)

<400>  150

His Ala Asp Gly Leu Phe Thr Ser Asp Xaa Xaa
1               5                   10

<210>  151
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  151

His Ala Asp Gly Leu Phe Thr His Asp Xaa Xaa
1               5                   10
```

```
<210>   152
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   152

His Ala Asp Gly Leu Phe Thr His Asp Xaa Xaa
1               5                   10

<210>   153
<211>   11
<212>   PRT
<213>   Artificial Sequence

<220>
<223>   Synthetic Peptide

<220>
<221>   MISC_FEATURE
<222>   (6)..(6)

<223>   Phe is (L)-Phe(2,4-di-Fluoro)

<220>
<221>   MISC_FEATURE
<222>   (10)..(11)
<223>   X is biphenylalanine(2-Me)

<400>   153

His Ala Asp Gly Thr Phe Thr Ser Asp Xaa Xaa
```

```
<210>  154
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)

<223>  Phe is Phe(penta-Fluoro)

<220>
<221>  MISC_FEATURE
<222>  (10)..(11)
<223>  X is biphenylalanine(2-Me)

<400>  154

His Xaa Asp Gly Leu Phe Thr Ser Asp Xaa Xaa
1               5                   10

<210>  155
<211>  11
<212>  PRT
<213>  Artificial Sequence

<220>
<223>  Synthetic Peptide

<220>
<221>  MISC_FEATURE
<222>  (6)..(6)
<223>  Phe is (D)-Phe(2,4-di-Fluoro)

<220>
<221>  MISC_FEATURE
<222>  (10)..(11)
<223>  X is biphenylalanine(2-Me)
```

```
<400> 155

His Ala Asp Gly Thr Phe Thr Ser Asp Xaa Xaa
1               5                   10

<210> 156
<211> 11
<212> PRT
<213> Artificial Sequence

<220>
<223> Synthetic Peptide

<220>
<221> MISC_FEATURE
<222> (2)..(2)
<223> X is aminoisobutyric acid

<220>
<221> MOD_RES
<222> (5)..(5)
<223> Nle

<220>
<221> MISC_FEATURE
<222> (10)..(11)
<223> X is biphenylalanine(2-Me)

<400> 156

His Xaa Asp Gly Leu Phe Thr His Asp Xaa Xaa
1               5                   10

<210> 157
<211> 11
<212> PRT
<213> Artificial Sequence

<220>
<223> Synthetic Peptide

<220>
<221> MISC_FEATURE
<222> (2)..(2)
<223> X is aminoisobutyric acid

<220>
<221> MOD_RES
<222> (5)..(5)
<223> Nle

<220>
<221> MISC_FEATURE
<222> (10)..(11)
<223> X is biphenylalanine(2-Me)
```

```
<400>  157

His Xaa Asp Gly Leu Phe Thr Ser Asp Xaa Xaa
1               5                   10

<210>  158
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (10)..(11)
<223>  X is biphenylalanine(2-Me)

<400>  158

His Xaa Asp Gly Thr Phe Thr Ser Asp Xaa Xaa
1               5                   10

<210>  159
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  159

His Xaa Asp Gly Thr Phe Thr Ser Asp Xaa Xaa
```

```
<210>  160
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (10)..(11)
<223>  X is biphenylalanine(2-Me)

<400>  160

His Xaa Glu Gly Leu Phe Thr Ser Asp Xaa Xaa
1               5                   10

<210>  161
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
```

```
<222>   (10)..(11)
<223>   X is biphenylalanine(2-Me)

<400>   161

His Xaa Glu Gly Leu Phe Thr His Asp Xaa Xaa
1               5                   10

<210>   162
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   162

His Xaa Glu Gly Leu Phe Thr Ser Asp Xaa Xaa
1               5                   10

<210>   163
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
```

```
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  163

His Xaa Glu Gly Thr Phe Thr His Asp Xaa Xaa
1               5                   10

<210>  164
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  164

His Xaa Glu Gly Thr Phe Thr Ser Asp Xaa Xaa
1               5                   10

<210>  165
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid
```

```
<220>
<221>  MISC_FEATURE
<222>  (10)..(11)
<223>  X is biphenylalanine(2-Me)

<400>  165

His Xaa His Gly Thr Phe Thr His Asp Xaa Xaa
1               5                   10

<210>  166
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (10)..(11)
<223>  X is biphenylalanine(2-Me)

<400>  166

His Xaa His Gly Thr Phe Thr Ser Asp Xaa Xaa
1               5                   10

<210>  167
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)
```

```
<400>  167

His Xaa His Gly Thr Phe Thr His Asp Xaa Xaa
1               5                   10

<210>  168
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MOD_RES
<222>  (6)..(6)
<223>  Phe is Phe(penta-Fluoro)

<220>
<221>  MOD_RES
<222>  (10)..(11)
<223>  X is biphenylalanine(2-Me)

<400>  168

His Xaa Asp Gly Leu Phe Thr Ser Asp Xaa Xaa
1               5                   10

<210>  169
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
```

```
<223>    Phe is Phe(penta-Fluoro)

<220>
<221>    MISC_FEATURE
<222>    (10)..(10)
<223>    X is biphenylalanine(2-Et)

<220>
<221>    MISC_FEATURE
<222>    (11)..(11)
<223>    X is biphenylalanine(2-Me)

<400>    169

His Ala Asp Gly Leu Phe Thr Ser Asp Xaa Xaa
1               5                   10

<210>    170
<211>    11
<212>    PRT
<213>    Artificial Sequence

<220>
<223>    Synthetic Peptide

<220>
<221>    MISC_FEATURE
<222>    (2)..(2)
<223>    X is aminoisobutyric acid <220>
<221>    MOD_RES
<222>    (5)..(5)
<223>    Nle <220>
<221>    MISC_FEATURE
<222>    (6)..(6)
<223>    Phe is Phe(penta-Fluoro)

<220>
<221>    MISC_FEATURE
<222>    (10)..(10)
<223>    X is biphenylalanine(2-Et)

<220>
<221>    MISC_FEATURE
<222>    (11)..(11)
<223>    X is biphenylalanine(2-Me)

<400>    170

His Xaa Asp Gly Leu Phe Thr Ser Asp Xaa Xaa
1               5                   10

<210>    171
```

```
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(2-Et)

<400>  171

His Xaa Asp Gly Leu Phe Thr Ser Asp Xaa Xaa
1               5                   10

<210>  172
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
```

```
<221>  MISC_FEATURE
<222>  (6)..(6)
<223>  Phe is Phe(penta-Fluoro)

<220>
<221>  MISC_FEATURE
<222>  (10)..(10)
<223>  Phe is Phe(penta-Fluoro)

<220>
<221>  MISC_FEATURE
<222>  (11)..(11)
<223>  X is biphenylalanine(2-Me)

<400>  172

His Xaa Asp Gly Leu Phe Thr Ser Asp Phe Xaa
1               5                   10

<210>  173
<211>  11
<212>  PRT
<213>  Artificial Sequence

<220>
<223>  Synthetic Peptide

<220>
<221>  MISC_FEATURE
<222>  (6)..(6)
<223>  Phe is Phe(penta-Fluoro)

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  173

His Ala Asp Gly Thr Phe Thr Ser Asp Xaa Xaa
1               5                   10

<210>  174
<211>  11
<212>  PRT
<213>  Artificial Sequence

<220>
<223>  Synthetic Peptide
```

```
<220>
<221>   MISC_FEATURE
<222>   (2)..(2)
<223>   X is aminoisobutyric acid <220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   174

His Xaa Glu Gly Thr Phe Thr Ser Asp Xaa Xaa
1               5                   10

<210>   175
<211>   11
<212>   PRT
<213>   Artificial Sequence

<220>
<223>   Synthetic Peptide

<220>
<221>   MISC_FEATURE
<222>   (6)..(6)
<223>   Phe is (L)-Phe(2,5-di-Phe)

<220>
<221>   MISC_FEATURE
<222>   (10)..(11)
<223>   X is biphenylalanine(2-Me)

<400>   175

His Ala Asp Gly Thr Phe Thr Ser Asp Xaa Xaa
1               5                   10

<210>   176
<211>   11
<212>   PRT
<213>   Artificial Sequence

<220>
<223>   Synthetic Peptide
```

```
<220>
<221>   MISC_FEATURE
<222>   (3)..(3)
<223>   X is diaminopropionic acid <220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   176

His Ala Xaa Gly Thr Phe Thr Ser Asp Xaa Xaa
1               5                   10

<210>   177
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MISC_FEATURE
<222>   (3)..(3)
<223>   X is diaminopropionic acid

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
```

```
<223>   X is biphenylalanine(2-Me)

<400>   177

His Xaa Xaa Gly Thr Phe Thr Ser Asp Xaa Xaa
1               5                   10

<210>   178
<211>   11
<212>   PRT
<213>   Artificial Sequence

<220>
<223>   Synthetic Peptide

<220>
<221>   MISC_FEATURE
<222>   (3)..(3)
<223>   X is diaminopropionic acid

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et, 2'-Me)

<220>
<221>   MISC_FEATURE
<222>   (11)..(11)
<223>   X is biphenylalanine(2-Me)

<400>   178

His Ala Xaa Gly Leu Phe Thr Ser Asp Xaa Xaa
1               5                   10

<210>   179
<211>   11
<212>   PRT
<213>   Artificial Sequence

<220>
<223>   Synthetic Peptide

<220>
<221>   MISC_FEATURE
```

```
<222>   (3)..(3)
<223>   X is diaminopropionic acid

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et, 2'Me)

<220>
<221>   MISC_FEATURE
<222>   (11)..(11)
<223>   X is biphenylalanine(2-Me)

<400>   179

His Ala Xaa Gly Thr Phe Thr Ser Asp Xaa Xaa
1               5                   10

<210>   180
<211>   11
<212>   PRT
<213>   Artificial Sequence

<220>
<223>   Synthetic Peptide

<220>
<221>   MISC_FEATURE
<222>   (3)..(3)
<223>   X is diaminopropionic acid

<220>
<221>   MISC_FEATURE
<222>   (10)..(10)
<223>   X is biphenylalanine(2-Et, 2'-Me)

<220>
<221>   MISC_FEATURE

<222>   (11)..(11)
<223>   X is biphenylalanine(2-Me)

<400>   180

His Ala Xaa Gly Thr Phe Thr Ser Asp Xaa Xaa
1               5                   10

<210>   181
<211>   11
<212>   PRT
```

```
<213>   Artificial Sequence

<220>
<223>   Synthetic Peptide

<220>
<221>   MISC_FEATURE
<222>   (2)..(2)
<223>   X is Iso-valine

<220>
<221>   MISC_FEATURE
<222>   (10)..(11)
<223>   X is biphenylalanine(2-Me)

<400>   181

His Xaa Glu Gly Thr Phe Thr Ser Asp Xaa Xaa
1               5                   10

<210>   182
<211>   11
<212>   PRT
<213>   Artificial Sequence

<220>
<223>   Synthetic Peptide

<220>
<221>   MISC_FEATURE
<222>   (5)..(5)
<223>   Leu is HomoLeu

<220>
<221>   MISC_FEATURE
<222>   (10)..(11)
<223>   X is biphenylalanine(2-Me)

<400>   182

His Ala Glu Gly Leu Phe Thr Ser Asp Xaa Xaa
1               5                   10

<210>   183
<211>   11
<212>   PRT
<213>   Artificial Sequence

<220>
<223>   Synthetic Peptide

<220>
<221>   MISC_FEATURE
<222>   (6)..(6)
```

```
<223>   Leu is homoLeu

<220>
<221>   MISC_FEATURE
<222>   (10)..(11)
<223>   X is biphenylalanine(2-Me)

<400>   183

His Ala Glu Gly Thr Leu Thr Ser Asp Xaa Xaa
1               5                   10

<210>   184
<211>   11
<212>   PRT
<213>   Artificial Sequence

<220>
<223>   Synthetic Peptide

<220>
<221>   MISC_FEATURE
<222>   (10)..(10)
<223>   Ala is 2-(9,10-Dihydrophenanthrenyl)-Ala <220>
<221>   MISC_FEATURE
<222>   (11)..(11)
<223>   X is biphenylalanine(2-Me)

<400>   184

His Ala Glu Gly Thr Phe Thr Ser Asp Ala Xaa
1               5                   10

<210>   185
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   Ala is 2-(9,10-Dihydrophenanthrenyl)-Ala

<400>   185
```

```
His Ala Glu Gly Thr Phe Thr Ser Asp Xaa Ala
1               5                   10

<210>   186
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et)

<220>
<221>   MISC_FEATURE
<222>   (11)..(11)
<223>   Ala is 2-(9,10-Dihydrophenanthrenyl)-Ala

<400>   186

His Ala Glu Gly Thr Phe Thr Ser Asp Xaa Ala
1               5                   10

<210>   187
<211>   11
<212>   PRT
<213>   Artificial Sequence

<220>
<223>   Synthetic Peptide

<220>
<221>   MISC_FEATURE
<222>   (10)..(11)
<223>   Ala is 2-(9,10-Dihydrophenanthrenyl)-Ala

<400>   187

His Ala Glu Gly Thr Phe Thr Ser Asp Ala Ala
1               5                   10

<210>   188
<211>   11
<212>   PRT
<213>   Artificial Sequence

<220>
<223>   Synthetic Peptide

<220>
```

```
<221>  MISC_FEATURE
<222>  (10)..(11)
<223>  Ala is 2-(9,10-Dihydrophenanthrenyl)-Ala

<400>  188

His Ala Glu Gly Thr Phe Thr Ser Asp Ala Ala
1               5                   10

<210>  189
<211>  11
<212>  PRT
<213>  Artificial Sequence

<220>
<223>  Synthetic Peptide

<220>
<221>  MISC_FEATURE
<222>  (10)..(10)
<223>  Ala is 2-FluorenylAla

<220>
<221>  MISC_FEATURE
<222>  (11)..(11)
<223>  Ala is 2-(9,10-Dihydrophenanthrenyl)-Ala

<400>  189

His Ala Glu Gly Thr Phe Thr Ser Asp Ala Ala
1               5                   10

<210>  190
<211>  11
<212>  PRT
<213>  Artificial Sequence

<220>
<223>  Synthetic Peptide

<220>
<221>  MISC_FEATURE
<222>  (10)..(10)
<223>  Ala is 2-(9,10-Dihydrophenanthrenyl)-Ala <220>
<221>  MISC_FEATURE
<222>  (11)..(11)
<223>  Ala is 2-FluorenylAla

<400>  190

His Ala Glu Gly Thr Phe Thr Ser Asp Ala Ala
```

```
<210>   191
<211>   11
<212>   PRT
<213>   Artificial Sequence

<220>
<223>   Synthetic Peptide

<220>
<221>   MISC_FEATURE
<222>   (10)..(10)
<223>   Ala is 2-(9,10-Dihydrophenanthrenyl)-Ala <220>
<221>   MISC_FEATURE
<222>   (11)..(11)
<223>   Ala is 2-FluorenylAla

<400>   191

His Ala Glu Gly Thr Phe Thr Ser Asp Ala Ala
1               5                   10

<210>   192
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et, 2'-Et)

<220>
<221>   MISC_FEATURE
<222>   (11)..(11)
<223>   X is biphenylalanine

<400>   192

His Ala Glu Gly Thr Phe Thr Ser Asp Xaa Xaa
1               5                   10

<210>   193
<211>   11
<212>   PRT
<213>   Artificial Sequence
```

```
<220>
<223>  Synthetic Peptide

<220>
<221>  MISC_FEATURE
<222>  (10)..(10)
<223>  X is biphenylalanine(2-Et, 2'-Et)

<220>
<221>  MISC_FEATURE
<222>  (11)..(11)
<223>  X is biphenylalanine(2-Me)

<400>  193

His Ala Glu Gly Thr Phe Thr Ser Asp Xaa Xaa
1               5                   10

<210>  194
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(10)
<223>  X is biphenylalanine(2-Et, 4-OMe)

<220>
<221>  MISC_FEATURE
<222>  (11)..(11)
<223>  X is biphenylalanine(2-Me)

<400>  194

His Ala Asp Gly Leu Phe Thr Ser Asp Xaa Xaa
1               5                   10

<210>  195
```

```
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Propyl, 2'-Me)

<220>
<221>  MISC_FEATURE
<222>  (11)..(11)
<223>  X is biphenylalanine

<400>  195

His Ala Glu Gly Thr Phe Thr Ser Asp Xaa Xaa
1               5                   10

<210>  196
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine

<220>
<221>  MISC_FEATURE
<222>  (11)..(11)
<223>  X is biphenylalanine(2-Et)

<400>  196

His Ala Asp Gly Thr Phe Thr Ser Asp Xaa Xaa
1               5                   10

<210>  197
<211>  11
<212>  PRT
<213>  Artificial Sequence
```

```
<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(11)
<223>  X is biphenylalanine(2-Et)

<400>  197

His Ala Asp Gly Thr Phe Thr Ser Asp Xaa Xaa
1               5                   10

<210>  198
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(2-Et)

<400>  198

His Ala Asp Gly Thr Phe Thr Ser Asp Xaa Xaa
1               5                   10

<210>  199
<211>  11
<212>  PRT
<213>  Artificial Sequence

<220>
<223>  Synthetic Peptide
```

```
<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  199

His Ala Glu Gly Thr Phe Thr Ser Asp Xaa Xaa
1               5                   10

<210>  200
<211>  11
<212>  PRT
<213>  Artificial Sequence

<220>

<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(11)
<223>  X is biphenylalanine

<400>  200

His Ala Asp Gly Thr Phe Thr Ser Asp Xaa Xaa
1               5                   10

<210>  201
<211>  11
<212>  PRT
<213>  Artificial Sequence

<220>
<223>  Synthetic Peptide

<220>
<221>  MOD_RES
```

```
<222>   (5)..(5)
<223>   Nle

<220>
<221>   MISC_FEATURE
<222>   (6)..(6)
<223>   Phe is L-alpha-Me-phe

<220>
<221>   MISC_FEATURE
<222>   (10)..(11)
<223>   X is biphenylalanine(2-Me)

<400>   201

His Ala Asp Gly Leu Phe Thr Ser Asp Xaa Xaa
1               5                   10

<210>   202
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is L-alpha-Me-phe

<220>
<221>   MISC_FEATURE
<222>   (10)..(11)
<223>   X is biphenylalanine(2-Me)

<400>   202

His Ala Asp Gly Leu Phe Thr Ser Asp Xaa Xaa
1               5                   10

<210>   203
<211>   11
<212>   PRT
<213>   Artificial Sequence

<220>
<223>   Synthetic Peptide

<220>
```

```
<221>   MISC_FEATURE
<222>   (2)..(2)
<223>   X is aminoisobutyric acid

<220>
<221>   MOD_RES
<222>   (5)..(5)
<223>   Nle

<220>
<221>   MISC_FEATURE
<222>   (6)..(6)
<223>   Phe is L-alpha-Me-phe

<220>
<221>   MISC_FEATURE
<222>   (10)..(11)
<223>   X is biphenylalanine(2-Me)

<400>   203

His Xaa Asp Gly Leu Phe Thr Ser Asp Xaa Xaa
1               5                   10

<210>   204
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MOD_RES
<222>   (5)..(5)
<223>   Nle

<220>
<221>   MISC_FEATURE
<222>   (6)..(6)
<223>   Phe is L-alpha-Me-phe

<220>
<221>   MISC_FEATURE
<222>   (10)..(11)
<223>   X is biphenylalanine(2-Me)

<400>   204

His Xaa Asp Gly Leu Phe Thr Ser Asp Xaa Xaa
1               5                   10
```

```
<210> 205
<211> 11
<212> PRT
<213> Artificial Sequence

<220>
<223> Synthetic Peptide

<220>
<221> MISC_FEATURE
<222> (2)..(2)
<223> X is aminoisobutyric acid

<220>
<221> MOD_RES
<222> (5)..(5)
<223> Nle

<220>
<221> MISC_FEATURE
<222> (6)..(6)
<223> Phe is L-alpha-Me-phe

<220>
<221> MISC_FEATURE
<222> (10)..(11)
<223> X is biphenylalanine(2-Me)

<400> 205

His Xaa Asp Gly Leu Phe Thr Ser Asp Xaa Xaa
1               5                   10

<210> 206
<211> 11
<212> PRT
<213> Artificial Sequence

<220>
<223> Synthetic Peptide

<220>
<221> MISC_FEATURE
<222> (2)..(2)
<223> X is aminoisobutyric acid

<220>
<221> MOD_RES
<222> (5)..(5)
<223> Nle

<220>
<221> MISC_FEATURE
<222> (6)..(6)
<223> Phe is L-alpha-Me-phe
```

```
<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine

<400>  206

His Xaa Asp Gly Leu Phe Thr Ser Asp Xaa Xaa
1               5                   10

<210>  207
<211>  11
<212>  PRT
<213>  Artificial Sequence

<220>
<223>  Synthetic Peptide

<220>
<221>  MISC_FEATURE
<222>  (10)..(11)
<223>  X is biphenylalanine(2-Me)

<400>  207

His Gly Glu Gly Thr Phe Thr Ser Asp Xaa Xaa
1               5                   10

<210>  208
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et, 4-OMe)

<220>
<221>  MISC_FEATURE
<222>  (11)..(11)
<223>  X is biphenylalanine(2,4-di-Me)

<400>  208

His Ala Glu Gly Thr Phe Thr Ser Asp Xaa Xaa
```

```
<210>  209
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et, 4-OMe)

<220>
<221>  MISC_FEATURE
<222>  (11)..(11)
<223>  X is biphenylalanine(4-OMe)

<400>  209

His Ala Glu Gly Thr Phe Thr Ser Asp Xaa Xaa
1               5                   10

<210>  210
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et, 4-OMe)

<220>
<221>  MISC_FEATURE
<222>  (11)..(11)
<223>  X is biphenylalanine(3-Me)

<400>  210

His Ala Glu Gly Thr Phe Thr Ser Asp Xaa Xaa
1               5                   10

<210>  211
<211>  11
<212>  PRT
<213>  Artificial Sequence

<220>
```

```
<223>   Synthetic Peptide

<220>
<221>   MISC_FEATURE
<222>   (10)..(10)
<223>   X is biphenylalanine(2-CH2OH, 4-OMe)

<220>
<221>   MISC_FEATURE
<222>   (11)..(11)
<223>   X is biphenylalanine(2-Me)

<400>   211

His Ala Glu Gly Thr Phe Thr Ser Asp Xaa Xaa
1               5                   10

<210>   212
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(2-Propyl, 2'-Me)

<400>   212

His Ala Glu Gly Thr Phe Thr Ser Asp Xaa Xaa
1               5                   10

<210>   213
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Et, 4-OMe)

<220>
```

```
<221> MISC_FEATURE
<222> (11)..(11)
<223> X is biphenylalanine(2,3,4,5-tetra-Me)

<400> 213

His Ala Glu Gly Thr Phe Thr Ser Asp Xaa Xaa
1               5                   10

<210> 214
<211> 11
<212> PRT
<213> Artificial Sequence

<220>
<223> Synthetic Peptide

<220>
<221> MISC_FEATURE
<222> (10)..(10)
<223> X is biphenylalanine(2-Et)

<220>
<221> MISC_FEATURE
<222> (11)..(11)
<223> X is biphenylalanine(2,2'-di-Me)

<400> 214

His Ala Glu Gly Thr Phe Thr Ser Asp Xaa Xaa
1               5                   10

<210> 215
<211> 11
<212> PRT
<213> Artificial Sequence

<220>
<223> Synthetic Peptide

<220>
<221> MISC_FEATURE
<222> (6)..(6)
<223> Phe is Phe(2-OMe)

<220>
<221> MISC_FEATURE
<222> (10)..(11)
<223> X is biphenylalanine(2-Me)

<400> 215

His Ala Asp Gly Thr Phe Thr Ser Asp Xaa Xaa
1               5                   10
```

```
<210>  216
<211>  11
<212>  PRT
<213>  Artificial Sequence

<220>
<223>  Synthetic Peptide

<220>
<221>  MISC_FEATURE
<222>  (6)..(6)
<223>  Phe is Phe(2-Hydroxy)

<220>
<221>  MISC_FEATURE
<222>  (10)..(11)
<223>  X is biphenylalanine(2-Me)

<400>  216
```

His Ala Asp Gly Thr Phe Thr Ser Asp Xaa Xaa
1               5                   10

```
<210>  217
<211>  11
<212>  PRT
<213>  Artificial Sequence

<220>
<223>  Synthetic Peptide

<220>
<221>  MISC_FEATURE
<222>  (6)..(6)
<223>  Phe is Phe(2-Iodo)

<220>
<221>  MISC_FEATURE
<222>  (10)..(11)
<223>  X is biphenylalanine(2-Me)

<400>  217
```

His Ala Asp Gly Thr Phe Thr Ser Asp Xaa Xaa
1               5                   10

```
<210>  218
<211>  11
<212>  PRT
<213>  Artificial Sequence

<220>
```

```
<223>   Synthetic Peptide

<220>
<221>   MISC_FEATURE
<222>   (6)..(6)
<223>   X is biphenylalanine(2,2'-di-Me)

<220>
<221>   MISC_FEATURE
<222>   (10)..(11)
<223>   X is biphenylalanine(2-Me)

<400>   218

His Ala Asp Gly Thr Phe Thr Ser Asp Xaa Xaa
1               5                   10

<210>   219
<211>   11
<212>   PRT
<213>   Artificial Sequence

<220>
<223>   Synthetic Peptide

<220>
<221>   MISC_FEATURE
<222>   (6)..(6)
<223>   Tyr is Tyr(3-Iodo)

<220>
<221>   MISC_FEATURE
<222>   (10)..(11)
<223>   X is biphenylalanine(2-Me)

<400>   219

His Ala Asp Gly Thr Tyr Thr Ser Asp Xaa Xaa
1               5                   10

<210>   220
<211>   11
<212>   PRT
<213>   Artificial Sequence

<220>
<223>   Synthetic Peptide

<220>
<221>   MISC_FEATURE
<222>   (6)..(6)
<223>   Tyr is Tyr(3-NO2)

<220>
```

```
<221>   MISC_FEATURE
<222>   (10)..(11)
<223>   X is biphenylalanine(2-Me)

<400>   220

His Ala Asp Gly Thr Tyr Thr Ser Asp Xaa Xaa
1               5                   10

<210>   221
<211>   11
<212>   PRT
<213>   Artificial Sequence

<220>
<223>   Synthetic Peptide

<220>
<221>   MISC_FEATURE
<222>   (6)..(6)
<223>   Phe is (L)-Phe(2,3-di-Fluoro)

<220>
<221>   MISC_FEATURE
<222>   (10)..(11)
<223>   X is biphenylalanine(2-Me)

<400>   221

His Ala Asp Gly Thr Phe Thr Ser Asp Xaa Xaa
1               5                   10

<210>   222
<211>   11
<212>   PRT
<213>   Artificial Sequence

<220>
<223>   Synthetic Peptide

<220>
<221>   MISC_FEATURE
<222>   (6)..(6)
<223>   Tyr is Tyr(2,6-di-Me)

<220>
<221>   MISC_FEATURE
<222>   (10)..(11)
<223>   X is biphenylalanine(2-Me)

<400>   222

His Ala Asp Gly Thr Tyr Thr Ser Asp Xaa Xaa
1               5                   10
```

```
<210>  223
<211>  11
<212>  PRT
<213>  Artificial Sequence

<220>
<223>  Synthetic Peptide

<220>
<221>  MISC_FEATURE
<222>  (6)..(6)
<223>  Ala is 2-ThienylAla

<220>
<221>  MISC_FEATURE
<222>  (10)..(11)
<223>  X is biphenylalanine(2-Me)

<400>  223

His Ala Asp Gly Thr Ala Thr Ser Asp Xaa Xaa
1               5                   10

<210>  224
<211>  11
<212>  PRT
<213>  Artificial Sequence

<220>
<223>  Synthetic Peptide

<220>
<221>  MISC_FEATURE
<222>  (6)..(6)
<223>  Phe is (D)-Phe(2,3-di-Fluoro)

<220>
<221>  MISC_FEATURE
<222>  (10)..(11)
<223>  X is biphenylalanine(2-Me)

<400>  224

His Ala Asp Gly Thr Phe Thr Ser Asp Xaa Xaa
1               5                   10

<210>  225
<211>  11
<212>  PRT
<213>  Artificial Sequence

<220>
<223>  Synthetic Peptide
```

```
<220>
<221>  MISC_FEATURE
<222>  (10)..(10)
<223>  X is biphenylalanine(2-Et, 2'-Me)

<220>
<221>  MISC_FEATURE
<222>  (11)..(11)
<223>  X is biphenylalanine(2-Et)

<400>  225

His Ala Glu Gly Thr Phe Thr Ser Asp Xaa Xaa
1               5                   10

<210>  226
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (10)..(10)
<223>  X is biphenylalanine(2-Et, 2'-Me)

<220>
<221>  MISC_FEATURE
<222>  (11)..(11)
<223>  X is biphenylalanine(2-Me)

<400>  226

His Ala Asp Gly Leu Phe Thr Ser Asp Xaa Xaa
1               5                   10

<210>  227
<211>  11
<212>  PRT
<213>  Artificial Sequence

<220>
<223>  Synthetic Peptide

<220>
<221>  MISC_FEATURE
```

```
<222>   (2)..(2)
<223>   X is 1-Aminocyclopropane-1-carboxylic acid

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   227

His Xaa Asp Gly Leu Phe Thr Ser Asp Xaa Xaa
1               5                   10

<210>   228
<211>   11
<212>   PRT
<213>   Artificial Sequence

<220>
<223>   Synthetic Peptide

<220>
<221>   MISC_FEATURE
<222>   (2)..(2)
<223>   X is 1-Aminocyclopropane-1-carboxylic acid <220>
<221>   MOD_RES
<222>   (10)..(11)
<223>   X is biphenylalanine(2-Me)

<400>   228

His Xaa Asp Gly Leu Phe Thr His Asp Xaa Xaa
1               5                   10

<210>   229
<211>   11
<212>   PRT
<213>   Artificial Sequence

<220>
<223>   Synthetic Peptide

<220>
```

```
<221>  MISC_FEATURE
<222>  (2)..(2)
<223>  X is 1-Aminocyclopropane-1-carboxylic acid <220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  229

His Xaa Asp Gly Thr Phe Thr His Asp Xaa Xaa
1               5                   10

<210>  230
<211>  11
<212>  PRT
<213>  Artificial Sequence

<220>
<223>  Synthetic Peptide

<220>
<221>  MISC_FEATURE
<222>  (2)..(2)
<223>  X is 1-Aminocyclopropane-1-carboxylic acid <220>
<221>  MOD_RES
<222>  (5)..(5)
<223>  Nle <220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  230

His Xaa Asp Gly Leu Phe Thr His Asp Xaa Xaa
1               5                   10

<210>  231
<211>  11
<212>  PRT
<213>  Artificial Sequence
```

```
<220>
<223>  Synthetic Peptide

<220>
<221>  MISC_FEATURE
<222>  (6)..(6)
<223>  Phe is Phe(2-Trifluoromethyl)

<220>
<221>  MISC_FEATURE
<222>  (10)..(11)
<223>  X is biphenylalanine(2-Me)

<400>  231

His Ala Asp Gly Thr Phe Thr Ser Asp Xaa Xaa
1               5                   10

<210>  232
<211>  11
<212>  PRT
<213>  Artificial Sequence

<220>
<223>  Synthetic Peptide

<220>
<221>  MISC_FEATURE
<222>  (6)..(6)
<223>  Phe is Phe(2,4-di-Chloro)

<220>
<221>  MISC_FEATURE
<222>  (10)..(11)
<223>  X is biphenylalanine(2-Me)

<400>  232

His Ala Asp Gly Thr Phe Thr Ser Asp Xaa Xaa
1               5                   10

<210>  233
<211>  11
<212>  PRT
<213>  Artificial Sequence

<220>
<223>  Synthetic Peptide

<220>
<221>  MISC_FEATURE
<222>  (2)..(2)
<223>  X is 2-Aminobutyric acid
```

```
<220>
<221>  MISC_FEATURE
<222>  (10)..(11)
<223>  X is biphenylalanine(2-Me)

<400>  233

His Xaa Glu Gly Thr Phe Thr Ser Asp Xaa Xaa
1               5                   10

<210>  234
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  234

His Ala Asp Gly Leu Phe Thr Ser Asp Xaa Xaa
1               5                   10

<210>  235
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
```

```
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   235

His Ala Glu Gly Leu Phe Thr His Asp Xaa Xaa
1               5                   10

<210>   236
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   236

His Xaa Asp Gly Thr Phe Thr Ser Asp Xaa Xaa
1               5                   10

<210>   237
<211>   11
<212>   PRT
<213>   Artificial Sequence

<220>
```

```
<223>   Synthetic Peptide

<220>
<221>   MISC_FEATURE
<222>   (2)..(2)
<223>   X is aminoisobutyric acid

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   237

His Xaa Glu Gly Leu Phe Thr His Asp Xaa Xaa
1               5                   10

<210>   238
<211>   11
<212>   PRT
<213>   Artificial Sequence

<220>
<223>   Synthetic Peptide

<220>
<221>   MISC_FEATURE
<222>   (6)..(6)
<223>   Phe is Phe(2-Me)

<220>
<221>   MISC_FEATURE
<222>   (10)..(11)
<223>   X is biphenylalanine(2-Me)

<400>   238

His Ala Glu Gly Thr Phe Thr Ser Asp Xaa Xaa
1               5                   10
```

```
<210>  239
<211>  11
<212>  PRT
<213>  Artificial Sequence

<220>
<223>  Synthetic Peptide

<220>
<221>  MISC_FEATURE
<222>  (10)..(11)
<223>  X is biphenylalanine(2-Et)

<400>  239

His Ala Glu Gly Thr Phe Thr Ser Asp Xaa Xaa
1               5                   10

<210>  240
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et, 4-OMe)

<220>
<221>  MISC_FEATURE
<222>  (11)..(11)
<223>  X is biphenylalanine

<400>  240

His Ala Glu Gly Thr Phe Thr Ser Asp Xaa Xaa
1               5                   10

<210>  241
<211>  11
<212>  PRT
<213>  Artificial Sequence

<220>
<223>  Synthetic Peptide

<220>
<221>  MISC_FEATURE
<222>  (6)..(6)
<223>  Phe is Phe(2-Chloro)
```

```
<220>
<221>  MISC_FEATURE
<222>  (10)..(11)
<223>  X is biphenylalanine(2-Me)

<400>  241

His Ala Glu Gly Thr Phe Thr Ser Asp Xaa Xaa
1               5                   10

<210>  242
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et, 2'-Me)

<220>
<221>  MISC_FEATURE
<222>  (11)..(11)
<223>  X is biphenylalanine(2,2'-di-Me)

<400>  242

His Ala Glu Gly Thr Phe Thr Ser Asp Xaa Xaa
1               5                   10

<210>  243
<211>  11
<212>  PRT
<213>  Artificial Sequence

<220>
<223>  Synthetic Peptide

<220>
<221>  MISC_FEATURE
<222>  (2)..(2)
<223>  Glu is gamma-carboxy-glu

<220>
<221>  MISC_FEATURE
<222>  (10)..(11)
<223>  X is biphenylalanine(2-Me)

<400>  243

His Ala Glu Gly Thr Phe Thr Ser Asp Xaa Xaa
1               5                   10
```

```
<210>   244
<211>   11
<212>   PRT
<213>   Artificial Sequence

<220>
<223>   Synthetic Peptide

<220>
<221>   MISC_FEATURE
<222>   (10)..(11)
<223>   X is biphenylalanine(2-Me)

<400>   244

His Ala Cys Gly Thr Phe Thr Ser Asp Xaa Xaa
1               5                   10

<210>   245
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   245

His Ala Glu Gly Leu Phe Thr Ser Asp Xaa Xaa
1               5                   10

<210>   246
<211>   11
```

```
<212>  PRT
<213>  Artificial Sequence

<220>
<223>  Synthetic Peptide

<220>
<221>  MISC_FEATURE
<222>  (2)..(2)
<223>  X is L-4-ThioPro

<220>
<221>  MISC_FEATURE
<222>  (10)..(11)
<223>  X is biphenylalanine

<400>  246

His Xaa Glu Gly Thr Phe Thr Ser Asp Xaa Xaa
1               5                   10

<210>  247
<211>  11
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
<223>  X is biphenylalanine(2,2'-di-Me)

<400>  247

His Ala Glu Gly Thr Phe Thr Ser Asp Xaa Xaa
1               5                   10

<210>  248
<211>  11
<212>  PRT
<213>  Artificial Sequence

<220>
<223>  Synthetic Peptide

<220>
<221>  MISC_FEATURE
```

```
<222>  (10)..(10)
<223>  X is biphenylalanine(2-Me)

<220>
<221>  MISC_FEATURE
<222>  (11)..(11)
<223>  X is biphenylalanine(2,2'-di-Me)

<400>  248

His Ala Glu Gly Thr Phe Thr Ser Asp Xaa Xaa
1               5                   10

<210>  249
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2'-Me)

<220>
<221>  MISC_FEATURE
<222>  (11)..(11)
<223>  X is biphenylalanine(2-Me)

<400>  249

His Ala Glu Gly Thr Phe Thr Ser Asp Xaa Xaa
1               5                   10

<210>  250
<211>  11
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
<223>  X is biphenylalanine(2'-Me)

<400>  250
```

```
His Ala Glu Gly Thr Phe Thr Ser Asp Xaa Xaa
1               5                   10

<210>   251
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(2'-Me)

<400>   251

His Ala Glu Gly Thr Phe Thr Ser Asp Xaa Xaa
1               5                   10

<210>   252
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2'-Me)

<220>
<221>   MISC_FEATURE
<222>   (11)..(11)
<223>   X is biphenylalanine

<400>   252

His Ala Glu Gly Thr Phe Thr Ser Asp Xaa Xaa
1               5                   10

<210>   253
<211>   11
<212>   PRT
<213>   Artificial Sequence
```

```
<220>
<223>   Synthetic Peptide

<220>
<221>   MISC_FEATURE
<222>   (2)..(2)
<223>   X is aminoisobutyric acid

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2'-Me)

<220>
<221>   MISC_FEATURE
<222>   (11)..(11)
<223>   X is biphenylalanine(2-Me)

<400>   253

His Xaa Glu Gly Leu Phe Thr Ser Asp Xaa Xaa
1               5                   10

<210>   254
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2'-Me)

<220>
<221>   MISC_FEATURE
<222>   (11)..(11)
<223>   X is biphenylalanine(2,2'-di-Me)

<400>   254

His Ala Glu Gly Thr Phe Thr Ser Asp Xaa Xaa
1               5                   10
```

```
<210>  255
<211>  11
<212>  PRT
<213>  Artificial Sequence

<220>
<223>  Synthetic Peptide

<220>
<221>  MISC_FEATURE
<222>  (10)..(11)
<223>  X is biphenylalanine(2'-Me)

<400>  255

His Ala Glu Gly Thr Phe Thr Ser Asp Xaa Xaa
1               5                   10

<210>  256
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2,2'-di-me)

<220>
<221>  MISC_FEATURE
<222>  (11)..(11)
<223>  X is biphenylalanine

<400>  256

His Ala Glu Gly Thr Phe Thr Ser Asp Xaa Xaa
1               5                   10

<210>  257
<211>  11
<212>  PRT
<213>  Artificial Sequence

<220>
<223>  Synthetic Peptide

<220>
<221>  MISC_FEATURE
<222>  (10)..(10)
```

```
<223>   X is biphenylalanine(2,2'-di-Me)

<220>
<221>   MISC_FEATURE
<222>   (11)..(11)
<223>   X is biphenylalanine(2-Me)

<400>   257

His Ala Glu Gly Thr Phe Thr Ser Asp Xaa Xaa
1               5                   10

<210>   258
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2,2'-di-Me)

<220>
<221>   MISC_FEATURE
<222>   (11)..(11)
<223>   X is biphenylalanine(2-Et)

<400>   258

His Ala Glu Gly Thr Phe Thr Ser Asp Xaa Xaa
1               5                   10

<210>   259
<211>   11
<212>   PRT
<213>   Artificial Sequence

<220>
<223>   Synthetic Peptide

<220>
<221>   MISC_FEATURE
<222>   (10)..(11)
<223>   X is biphenylalanine(2,2'-di-Me)

<400>   259

His Ala Glu Gly Thr Phe Thr Ser Asp Xaa Xaa
1               5                   10

<210>   260
```

```
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  Phe is Phe(4-n-Butyl)

<400>  260

His Ala Glu Gly Thr Phe Thr Ser Asp Xaa Phe
1               5                   10

<210>  261
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  Phe is Phe(3-phenyl)

<400>  261

His Ala Glu Gly Thr Phe Thr Ser Asp Xaa Xaa
1               5                   10

<210>  262
<211>  11
<212>  PRT
<213>  Artificial Sequence

<220>
<223>  Synthetic Peptide

<220>
```

```
<221>   MISC_FEATURE
<222>   (10)..(10)
<223>   X is biphenylalanine(2-Me)

<220>
<221>   MISC_FEATURE
<222>   (11)..(11)
<223>   Phe is Phe(4-Cyclohexyl)

<400>   262

His Ala Glu Gly Thr Phe Thr Ser Asp Xaa Phe
1               5                   10

<210>   263
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   Phe is Phe(4-phenoxy)

<400>   263

His Ala Glu Gly Thr Phe Thr Ser Asp Xaa Phe
1               5                   10

<210>   264
<211>   11
<212>   PRT
<213>   Artificial Sequence

<220>
<223>   Synthetic Peptide

<220>
<221>   MISC_FEATURE
<222>   (10)..(10)
<223>   Phe is Phe(4-n-Butyl)

<220>
<221>   MISC_FEATURE
<222>   (11)..(11)
<223>   X is biphenylalanine(2-Me)
```

```
<400>   264

His Ala Glu Gly Thr Phe Thr Ser Asp Phe Xaa
1               5                   10

<210>   265
<211>   11
<212>   PRT
<213>   Artificial Sequence

<220>
<223>   Synthetic Peptide

<220>
<221>   MISC_FEATURE
<222>   (10)..(10)
<223>   Phe is Phe(4-Cyclohexyl)

<220>
<221>   MISC_FEATURE
<222>   (11)..(11)
<223>   X is biphenylalanine(2-Me)

<400>   265

His Ala Glu Gly Thr Phe Thr Ser Asp Phe Xaa
1               5                   10

<210>   266
<211>   11
<212>   PRT
<213>   Artificial Sequence

<220>
<223>   Synthetic Peptide

<220>
<221>   MISC_FEATURE
<222>   (10)..(10)
<223>   Phe is (4-phenoxy)

<220>
<221>   MISC_FEATURE
<222>   (11)..(11)
<223>   X is biphenylalanine(2-Me)

<400>   266

His Ala Glu Gly Thr Phe Thr Ser Asp Phe Xaa
1               5                   10

<210>   267
<211>   11
```

```
<212>   PRT
<213>   Artificial Sequence

<220>
<223>   Synthetic Peptide

<220>
<221>   MISC_FEATURE
<222>   (6)..(6)
<223>   Phe is Phe(3-Fluoro)

<220>
<221>   MISC_FEATURE
<222>   (10)..(11)
<223>   X is biphenylalanine(2-Me)

<400>   267

His Ala Asp Gly Thr Phe Thr Ser Asp Xaa Xaa
1               5                   10

<210>   268
<211>   11
<212>   PRT
<213>   Artificial Sequence

<220>
<223>   Synthetic Peptide

<220>
<221>   MISC_FEATURE
<222>   (6)..(6)
<223>   Phe is Phe(4-Fluoro)

<220>
<221>   MISC_FEATURE
<222>   (10)..(11)
<223>   X is biphenylalanine(2-Me)

<400>   268

His Ala Asp Gly Thr Phe Thr Ser Asp Xaa Xaa
1               5                   10

<210>   269

<211>   11
<212>   PRT
<213>   Artificial Sequence

<220>
<223>   Synthetic Peptide
```

```
<220>
<221> MISC_FEATURE
<222> (6)..(6)
<223> Phe is Phe(3,4-di-Fluoro)

<220>
<221> MISC_FEATURE
<222> (10)..(11)
<223> X is biphenylalanine(2-Me)

<400> 269

His Ala Asp Gly Thr Phe Thr Ser Asp Xaa Xaa
1               5                   10

<210> 270
<211> 11
<212> PRT
<213> Artificial Sequence

<220>
<223> Synthetic Peptide

<220>
<221> MISC_FEATURE
<222> (6)..(6)
<223> Phe is Phe(3,5-di-Fluoro)

<220>
<221> MISC_FEATURE
<222> (10)..(11)
<223> X is biphenylalanine(2-Me)

<400> 270

His Ala Asp Gly Thr Phe Thr Ser Asp Xaa Xaa
1               5                   10

<210> 271
<211> 11
<212> PRT
<213> Artificial Sequence

<220>
<223> Synthetic Peptide

<220>
<221> MISC_FEATURE
<222> (6)..(6)
<223> Phe is Phe(3,4,5-tri-Fluoro)

<220>
<221> MISC_FEATURE
<222> (10)..(11)
<223> X is biphenylalanine(2-Me)
```

```
<400>  271

His Ala Asp Gly Thr Phe Thr Ser Asp Xaa Xaa
1               5                   10

<210>  272
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (10)..(11)
<223>  X is biphenylalanine(2-Me)

<400>  272

His Ala Asp Gly Leu Phe Thr His Asp Xaa Xaa
1               5                   10

<210>  273
<211>  11
<212>  PRT
<213>  Artificial Sequence

<220>
<223>  Synthetic Peptide

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  273

His Ala Asp Gly Thr Phe Thr His Asp Xaa Xaa
1               5                   10

<210>  274
<211>  11
```

```
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   274

His Ala Glu Gly Leu Phe Thr His Asp Xaa Xaa
1               5                   10

<210>   275
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   275

His Ala His Gly Leu Phe Thr His Asp Xaa Xaa
1               5                   10

<210>   276
```

```
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(10)
<223>  X is biphenylalanine(2,4-di-OMe)

<220>
<221>  MISC_FEATURE
<222>  (11)..(11)
<223>  X is biphenylalanine(2-Me)

<400>  276

His Ala Asp Gly Leu Phe Thr Ser Asp Xaa Xaa
1               5                   10

<210>  277
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me, 4-OMe)

<220>
<221>  MISC_FEATURE
<222>  (11)..(11)
<223>  X is biphenylalanine(3,4-Methylenedioxy)

<400>  277

His Ala Glu Gly Thr Phe Thr Ser Asp Xaa Xaa
1               5                   10
```

```
<210>  278
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(3,4-Methylenedioxy)

<400>  278

His Ala Glu Gly Thr Phe Thr Ser Asp Xaa Xaa
1               5                   10

<210>  279
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2,4-di-OMe)

<220>
<221>  MISC_FEATURE
<222>  (11)..(11)
<223>  Phe is 4-(1-Naphthyl)-Phe

<400>  279

His Ala Asp Gly Thr Phe Thr Ser Asp Xaa Phe
1               5                   10

<210>  280
<211>  11
<212>  PRT
<213>  Artificial Sequence

<220>
<223>  Synthetic Peptide
```

```
<220>
<221>    MISC_FEATURE
<222>    (10)..(10)
<223>    X is biphenylalanine(2-Me, 4-OMe)

<220>
<221>    MISC_FEATURE
<222>    (11)..(11)
<223>    Phe is 4-(1-Naphthyl)-Phe

<400>    280

His Ala Glu Gly Thr Phe Thr Ser Asp Xaa Phe
1               5                   10

<210>    281
<211>    11
<212>    PRT
<213>    Artificial Sequence

<220>
<223>    Synthetic Peptide

<220>
<221>    MISC_FEATURE
<222>    (10)..(10)
<223>    X is biphenylalanine(2,4-di-OMe)

<220>
<221>    MISC_FEATURE
<222>    (11)..(11)
<223>    X is biphenylalanine(4-OMe)

<400>    281

His Ala Asp Gly Thr Phe Thr Ser Asp Xaa Xaa
1               5                   10

<210>    282
<211>    11
<212>    PRT
<213>    Artificial Sequence

<220>
<223>    Synthetic Peptide

<220>
<221>    MISC_FEATURE
<222>    (10)..(10)
<223>    X is biphenylalanine(2-Me, 4-OMe)

<220>
<221>    MISC_FEATURE
<222>    (11)..(11)
<223>    X is biphenylalanine(4-OMe)
```

```
<400>  282

His Ala Glu Gly Thr Phe Thr Ser Asp Xaa Xaa
1               5                   10

<210>  283
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2,4-di-OMe)

<220>
<221>  MISC_FEATURE
<222>  (11)..(11)
<223>  X is biphenylalanine(4-Me)

<400>  283

His Ala Glu Gly Thr Phe Thr Ser Asp Xaa Xaa
1               5                   10

<210>  284
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me, 4-OMe)

<220>
<221>  MISC_FEATURE
<222>  (11)..(11)
<223>  X is biphenylalanine(4-Me)

<400>  284

His Ala Glu Gly Thr Phe Thr Ser Asp Xaa Xaa
1               5                   10

<210>  285
<211>  11
```

```
<212>   PRT
<213>   Artificial Sequence

<220>
<223>   Synthetic Peptide

<220>
<221>   MISC_FEATURE
<222>   (10)..(11)
<223>   X is biphenylalanine(2,4-di-OMe)

<400>   285

His Ala Asp Gly Thr Phe Thr Ser Asp Xaa Xaa
1               5                   10

<210>   286
<211>   11
<212>   PRT
<213>   Artificial Sequence

<220>
<223>   Synthetic Peptide

<220>
<221>   MISC_FEATURE
<222>   (10)..(11)
<223>   X is biphenylalanine(2-Me, 4-OMe)

<400>   286

His Ala Glu Gly Thr Phe Thr Ser Asp Xaa Xaa
1               5                   10

<210>   287
<211>   11
<212>   PRT
<213>   Artificial Sequence

<220>
<223>   Synthetic Peptide

.
<220>
<221>   MISC_FEATURE
<222>   (10)..(11)
<223>   X is biphenylalanine(2,4-di-Me)

<400>   287

His Ala Asp Gly Thr Phe Thr Ser Asp Xaa Xaa
1               5                   10

<210>   288
```

```
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2,4-di-OMe)

<220>
<221>  MISC_FEATURE
<222>  (11)..(11)
<223>  X is biphenylalanine(3-Me)

<400>  288

His Ala Glu Gly Thr Phe Thr Ser Asp Xaa Xaa
1               5                   10

<210>  289
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me, 4-OMe)

<220>
<221>  MISC_FEATURE
<222>  (11)..(11)
<223>  X is biphenylalanine(3-Me)

<400>  289

His Ala Glu Gly Thr Phe Thr Ser Asp Xaa Xaa
1               5                   10

<210>  290
<211>  11
<212>  PRT
<213>  Artificial Sequence

<220>
<223>  Synthetic Peptide

<220>
```

```
<221>  MISC_FEATURE
<222>  (3)..(3)
<223>  Ala is 4-Thiazoyl-ala

<220>
<221>  MISC_FEATURE
<222>  (10)..(11)
<223>  X is biphenylalanine(2-Me)

<400>  290

His Ala Ala Gly Thr Phe Thr Ser Asp Xaa Xaa
1               5                   10

<210>  291
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  291

His Ala Asp Gly Leu Phe Thr His Asp Xaa Xaa
1               5                   10

<210>  292
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et, 4,5-
Methylenedioxy)
```

```
<220>
<221>  MISC_FEATURE
<222>  (11)..(11)
<223>  X is biphenylalanine(2-Me)

<400>  292

His Ala Glu Gly Thr Phe Thr Ser Asp Xaa Xaa
1               5                   10

<210>  293
<211>  11
<212>  PRT
<213>  Artificial Sequence

<220>
<223>  Synthetic Peptide

<220>
<221>  MISC_FEATURE
<222>  (2)..(2)
<223>  Ala is N-Me-Ala

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  293

His Ala Glu Gly Leu Phe Thr His Asp Xaa Xaa
1               5                   10

<210>  294
<211>  11
<212>  PRT
<213>  Artificial Sequence

<220>
<223>  Synthetic Peptide
```

```
<220>
<221>  MISC_FEATURE
<222>  (2)..(2)
<223>  Ala is N-Me-A

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  294

His Ala Asp Gly Leu Phe Thr Ser Asp Xaa Xaa
1               5                   10

<210>  295
<211>  11
<212>  PRT
<213>  Artificial Sequence

<220>
<223>  Synthetic Peptide

<220>
<221>  MISC_FEATURE
<222>  (2)..(2)
<223>  Ala is N-Me-Ala

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  295

His Ala Asp Gly Thr Phe Thr Ser Asp Xaa Xaa
1               5                   10

<210>  296
```

```
<211>  11
<212>  PRT
<213>  Artificial Sequence

<220>
<223>  Synthetic Peptide

<220>
<221>  MISC_FEATURE
<222>  (2)..(2)
<223>  Ala is N-Me-Ala

<220>
<221>  MOD_RES
<222>  (5)..(5)
<223>  Nle

<220>
<221>  MISC_FEATURE
<222>  (6)..(6)
<223>  Phe is phe(penta-Fluoro)

<220>
<221>  MISC_FEATURE
<222>  (10)..(11)
<223>  X is biphenylalanine(2-Me)

<400>  296

His Ala Glu Gly Leu Phe Thr His Asp Xaa Xaa
1               5                   10

<210>  297
<211>  11
<212>  PRT
<213>  Artificial Sequence

<220>
<223>  Synthetic Peptide

<220>
<221>  MISC_FEATURE
<222>  (2)..(2)
<223>  Ala is N-Me-Ala

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  297
```

```
His Ala Glu Gly Thr Phe Thr Ser Asp Xaa Xaa
1               5                   10
```

<210> 298
<211> 11
<212> PRT
<213> Artificial Sequence

<220>
<223> Synthetic Peptide

<220>
<221> MISC_FEATURE
<222> (2)..(2)
<223> X is Sarcosyl

<220>
<221> MISC_FEATURE
<222> (10)..(11)
<223> X is biphenylalanine(2-Me)

<400> 298

```
His Xaa Glu Gly Thr Phe Thr Ser Asp Xaa Xaa
1               5                   10
```

<210> 299
<211> 11
<212> PRT
<213> Artificial Sequence

<220>
<223> Synthetic Peptide

<220>
<221> MISC_FEATURE
<222> (10)..(10)
<223> X is biphenylalanine(3-CH2NH2)

<220>
<221> MISC_FEATURE
<222> (11)..(11)
<223> X is biphenylalanine(2-Me)

<400> 299

```
His Ala Glu Gly Thr Phe Thr Ser Asp Xaa Xaa
1               5                   10
```

<210> 300
<211> 11
<212> PRT
<213> Artificial Sequence

```
<220>
<223>   Synthetic Peptide

<220>
<221>   MISC_FEATURE
<222>   (10)..(10)
<223>   X is biphenylalanine(2-CH2NH2)

<220>
<221>   MISC_FEATURE
<222>   (11)..(11)
<223>   X is biphenylalanine(2-Me)

<400>   300

His Ala Glu Gly Thr Phe Thr Ser Asp Xaa Xaa
1               5                   10

<210>   301
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(4-CH2NH2)

<220>
<221>   MISC_FEATURE
<222>   (11)..(11)
<223>   X is biphenylalanine(2-Me)

<400>   301

His Ala Glu Gly Thr Phe Thr Ser Asp Xaa Xaa
1               5                   10

<210>   302
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(3-CH2-COOH)
```

```
<220>
<221> MISC_FEATURE
<222> (11)..(11)
<223> X is biphenylalanine(2-Me)

<400> 302

His Ala Glu Gly Thr Phe Thr Ser Asp Xaa Xaa
1               5                   10

<210> 303
<211> 11
<212> PRT
<213> Artificial Sequence

<220>
<223> Synthetic Peptide

<220>
<221> MISC_FEATURE
<222> (10)..(10)
<223> X is biphenylalanine(2-Me)

<220>
<221> MISC_FEATURE
<222> (11)..(11)
<223> X is biphenylalanine(2'-CH2-COOH)

<400> 303

His Ala Glu Gly Thr Phe Thr Ser Asp Xaa Xaa
1               5                   10

<210> 304
<211> 11
<212> PRT
<213> Artificial Sequence

<220>
<223> Synthetic Peptide

<220>
<221> MISC_FEATURE
<222> (10)..(10)
<223> X is biphenylalanine(2-Me)

<220>
<221> MISC_FEATURE
<222> (11)..(11)
<223> X is (D,L)-biphenylalanine(2-CH2-COOH)

<400> 304

His Ala Glu Gly Thr Phe Thr Ser Asp Xaa Xaa
```

```
<210>   305
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(4-CH2-COOH)

<400>   305

His Ala Glu Gly Thr Phe Thr Ser Asp Xaa Xaa
1               5                   10

<210>   306
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(3-CH2-COOH)

<400>   306

His Ala Glu Gly Thr Phe Thr Ser Asp Xaa Xaa
1               5                   10

<210>   307
<211>   11
<212>   PRT
<213>   Artificial Sequence
```

```
<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(3-CH2NH2)

<400>   307

His Ala Glu Gly Thr Phe Thr Ser Asp Xaa Xaa
1               5                   10

<210>   308
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(4-CH2NH2)

<400>   308

His Ala Glu Gly Thr Phe Thr Ser Asp Xaa Xaa
1               5                   10

<210>   309
<211>   11
<212>   PRT
<213>   Artificial Sequence

<220>
<223>   Synthetic Peptide

<220>
<221>   MISC_FEATURE
<222>   (10)..(10)
<223>   X is biphenylalanine(2-Me)
```

```
<220>
<221>  MISC_FEATURE
<222>  (11)..(11)
<223>  X is biphenylalanine(2-CH2NH2)

<400>  309

His Ala Glu Gly Thr Phe Thr Ser Asp Xaa Xaa
1               5                   10

<210>  310
<211>  11
<212>  PRT
<213>  Artificial Sequence

<220>
<223>  Synthetic Peptide

<220>
<221>  MISC_FEATURE
<222>  (10)..(10)
<223>  Phe is Phe[4-(1-propargyl)]

<220>
<221>  MISC_FEATURE
<222>  (11)..(11)
<223>  X is biphenylalanine(2-Me)

<400>  310

His Ala Glu Gly Thr Phe Thr Ser Asp Phe Xaa
1               5                   10

<210>  311
<211>  11
<212>  PRT

<213>  Artificial Sequence
<220>
<223>  Synthetic Peptide

<220>
<221>  MISC_FEATURE
<222>  (10)..(10)
<223>  Phe is Phe[4-(1-propenyl)]

<220>
<221>  MISC_FEATURE
<222>  (11)..(11)
<223>  X is biphenylalanine(2-Me)

<400>  311
```

```
His Ala Glu Gly Thr Phe Thr Ser Asp Phe Xaa
1               5                   10

<210>   312
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   312

His Ala Asp Gly Thr Phe Thr Ser Asp Xaa Xaa
1               5                   10

<210>   313
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   313
```

```
His Ala Asp Gly Thr Phe Thr Ser Asp Xaa Xaa
1               5                   10

<210>   314
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   314

His Ala Asp Gly Thr Phe Thr Ser Asp Xaa Xaa
1               5                   10

<210>   315
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)
```

```
<400>  315

His Ala Asp Gly Thr Phe Thr Ser Asp Xaa Xaa
1               5                   10

<210>  316
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  316

His Ala Asp Gly Thr Phe Thr Ser Asp Xaa Xaa
1               5                   10

<210>  317
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(2-Et)
```

```
<220>
<221>  MISC_FEATURE
<222>  (11)..(11)
<223>  X is biphenylalanine(2-Me)

<400>  317

His Xaa Asp Gly Thr Phe Thr Ser Asp Xaa Xaa
1               5                   10

<210>  318
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  318

His Xaa Asp Gly Thr Phe Thr Ser Asp Xaa Xaa
1               5                   10

<210>  319
<211>  11
<212>  PRT
<213>  Artificial Sequence

<220>
<223>  Synthetic Peptide

<220>
<221>  MOD_RES
<222>  (5)..(5)
```

```
<223>   Nle

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   319

His Ala Asp Gly Leu Phe Thr Ser Asp Xaa Xaa
1               5                   10

<210>   320
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   320

His Ala Asp Gly Leu Phe Thr Ser Asp Xaa Xaa
1               5                   10

<210>   321
<211>   11
<212>   PRT
<213>   Artificial Sequence

<220>
```

```
<223>   Synthetic Peptide

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(11)
<223>   X is biphenylalanine(2-Me)

<400>   321

His Ala Asp Gly Leu Phe Thr Ser Asp Xaa Xaa
1               5                   10

<210>   322
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is Phe(penta-Fluoro)

<220>
<221>   MISC_FEATURE
<222>   (10)..(10)
<223>   X is biphenylalanine(2-Me)

<220>
<221>   MISC_FEATURE
<222>   (11)..(11)
<223>   X is biphenylalanine(2-Et)

<400>   322

His Ala Asp Gly Leu Phe Thr Ser Asp Xaa Xaa
1               5                   10
```

```
<210>  323
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  323

His Xaa Asp Gly Leu Phe Thr Ser Asp Xaa Xaa
1               5                   10

<210>  324
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)
<223>  Phe is Phe(penta-Fluoro)
```

```
<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  324

His Xaa Asp Gly Leu Phe Thr Ser Asp Xaa Xaa
1               5                   10

<210>  325
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(11)
<223>  X is biphenylalanine(2-Me)

<400>  325

His Xaa Asp Gly Leu Phe Thr Ser Asp Xaa Xaa
1               5                   10

<210>  326
<211>  11
<212>  PRT
<213>  Artificial Sequence

<220>
```

```
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)
<223>  Phe is Phe(penta-Fluoro)

<220>
<221>  MISC_FEATURE
<222>  (10)..(10)
<223>  X is biphenylalanine(2-Me)

<220>
<221>  MISC_FEATURE
<222>  (11)..(11)
<223>  X is biphenylalanine(2-Et)

<400>  326

His Xaa Asp Gly Leu Phe Thr Ser Asp Xaa Xaa
1               5                   10

<210>  327
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Me)

<220>
<221>  MISC_FEATURE
<222>  (11)..(11)
<223>  X is (D,L)-alpha-Me-biphenylalanine

<400>  327

His Ala Glu Gly Thr Phe Thr Ser Asp Xaa Xaa
1               5                   10
```

```
<210>  328
<211>  11
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
<223>  X is (D,L)-alpha-Me-biphenylalanine

<400>  328

His Ala Glu Gly Thr Phe Thr Ser Asp Xaa Xaa
1               5                   10

<210>  329
<211>  11
<212>  PRT
<213>  Artificial Sequence

<220>
<223>  Synthetic Peptide

<220>
<221>  MISC_FEATURE
<222>  (5)..(5)
<223>  Thr is allo-Thr

<220>

<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  329

His Ala Asp Gly Thr Phe Thr Ser Asp Xaa Xaa
1               5                   10
```

```
<210>   330
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (7)..(7)
<223>   Thr is allo-Thr

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   330

His Ala Asp Gly Thr Phe Thr Ser Asp Xaa Xaa
1               5                   10

<210>   331
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
```

```
<223>   X is biphenylalanine(2-Me)

<400>   331

His Ala Asp Gly Thr Phe Thr Ser Asp Xaa Xaa
1               5                   10

<210>   332
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   332

His Ala Asp Gly Thr Phe Thr Thr Asp Xaa Xaa
1               5                   10

<210>   333
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
```

```
<222>   (11)..(11)
<223>   X is biphenylalanine(2-Me)

<400>   333

His Ala Asp Gly Thr Phe Thr Ser Glu Xaa Xaa
1               5                   10

<210>   334
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   334

His Ala Glu Gly Leu Phe Thr Ser Asp Xaa Xaa
1               5                   10

<210>   335
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
```

```
<221>   MISC_FEATURE
<222>   (11)..(11)
<223>   X is biphenylalanine(2-Me)

<400>   335

His Ala Asp Gly Thr Phe Thr Ser Asp Xaa Xaa
1               5                   10

<210>   336
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   336

His Xaa Asp Gly Thr Phe Thr Ser Asp Xaa Xaa
1               5                   10

<210>   337
<211>   11
<212>   PRT
<213>   Artificial Sequence

<220>
<223>   Synthetic Peptide

<220>
<221>   MISC_FEATURE
<222>   (2)..(2)
```

```
<223>   X is aminoisobutyric acid

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   337

His Xaa Asp Gly Thr Phe Thr Ser Asp Xaa Xaa
1               5                   10

<210>   338
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   338

His Xaa Asp Gly Thr Phe Thr Ser Asp Xaa Xaa
1               5                   10
```

```
<210>   339
<211>   10
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)-NH-[2-(penta-
Fluoro-phenyl)ethyl]

<400>   339

His Ala Asp Gly Thr Phe Thr Ser Asp Xaa
1               5                   10

<210>   340
<211>   10
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)-NH-[2-(penta-
Fluoro-phenyl)ethyl]

<400>   340

His Ala Asp Gly Leu Phe Thr Ser Asp Xaa
1               5                   10

<210>   341
```

```
<211> 10
<212> PRT
<213> Artificial Sequence

<220>
<223> Synthetic Peptide

<220>
<221> MISC_FEATURE
<222> (2)..(2)
<223> X is aminoisobutyric acid

<220>
<221> MISC_FEATURE
<222> (6)..(6)
<223> Phe is L-alpha-Me-phe

<220>
<221> MISC_FEATURE
<222> (10)..(10)
<223> X is biphenylalanine(2-Et)-NH-[2-(penta-
Fluoro-phenyl)ethyl]

<400> 341

His Xaa Glu Gly Thr Phe Thr Ser Asp Xaa
1               5                   10

<210> 342
<211> 10
<212> PRT
<213> Artificial Sequence

<220>
<223> Synthetic Peptide

<220>
<221> MISC_FEATURE
<222> (2)..(2)
<223> X is aminoisobutyric acid

<220>
<221> MOD_RES
<222> (5)..(5)
<223> Nle

<220>
<221> MISC_FEATURE
<222> (6)..(6)
<223> Phe is L-alpha-Me-phe

<220>
<221> MISC_FEATURE
<222> (10)..(10)
<223> X is biphenylalanine(2-Et)-NH-[2-(penta-
Fluoro-phenyl)ethyl]
```

```
<400>   342

His Xaa Asp Gly Leu Phe Thr Ser Asp Xaa
1               5                   10

<210>   343
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   343

His Xaa Asp Gly Thr Phe Thr Ser Asp Xaa Xaa
1               5                   10

<210>   344
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
```

```
<223>   X is biphenylalanine(2-Et)

<220>
<221>   MISC_FEATURE
<222>   (11)..(11)
<223>   X is biphenylalanine(2-Me)

<400>   344

His Ala Glu Gly Thr Phe Thr Ser Asp Xaa Xaa
1               5                   10

<210>   345
<211>   11
<212>   PRT
<213>   Artificial Sequence

<220>
<223>   Synthetic Peptide

<220>
<221>   MISC_FEATURE
<222>   (6)..(6)
<223>   Phe is L-Phe(2,6-di-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   345

His Ala Glu Gly Thr Phe Thr Ser Asp Xaa Xaa
1               5                   10

<210>   346
<211>   11
<212>   PRT
<213>   Artificial Sequence

<220>
<223>   Synthetic Peptide

<220>
<221>   MISC_FEATURE
<222>   (2)..(2)
<223>   Ala is N-Me-Ala

<220>
<221>   MISC_FEATURE
```

```
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   346

His Ala Glu Gly Thr Phe Thr Ser Asp Xaa Xaa
1               5                   10

<210>   347
<211>   11
<212>   PRT
<213>   Artificial Sequence

<220>
<223>   Synthetic Peptide

<220>
<221>   MISC_FEATURE
<222>   (3)..(3)
<223>   Glu is N-Me-Glu

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   347

His Ala Glu Gly Thr Phe Thr Ser Asp Xaa Xaa
1               5                   10

<210>   348
<211>   11
<212>   PRT
```

```
<213>    Artificial Sequence

<220>
<223>    Synthetic Peptide

<220>
<221>    MISC_FEATURE
<222>    (4)..(4)
<223>    Gly is N-Me-Gly

<220>
<221>    MISC_FEATURE
<222>    (6)..(6)
<223>    Phe is L-alpha-Me-phe

<220>
<221>    MISC_FEATURE
<222>    (10)..(10)
<223>    X is biphenylalanine(2-Et)

<220>
<221>    MISC_FEATURE
<222>    (11)..(11)
<223>    X is biphenylalanine(2-Me)

<400>    348

His Ala Glu Gly Thr Phe Thr Ser Asp Xaa Xaa
1               5                   10

<210>    349
<211>    11
<212>    PRT
<213>    Artificial Sequence

<220>
<223>    Synthetic Peptide

<220>
<221>    MOD_RES
<222>    (5)..(5)
<223>    Nle

<220>
<221>    MISC_FEATURE
<222>    (6)..(6)
<223>    Phe is (D,L)-alpha-Me-Phe(penta-Fluoro)

<220>
<221>    MISC_FEATURE
<222>    (10)..(10)
<223>    X is biphenylalanine(2-Et,4-OMe)

<220>
<221>    MISC_FEATURE
<222>    (11)..(11)
```

```
<223>   X is biphenylalanine(2-Me)

<400>   349

His Ala Asp Gly Leu Phe Thr Ser Asp Xaa Xaa
1               5                   10

<210>   350
<211>   11
<212>   PRT
<213>   Artificial Sequence

<220>
<223>   Synthetic Peptide

<220>
<221>   MOD_RES
<222>   (5)..(5)
<223>   Nle

<220>
<221>   MISC_FEATURE
<222>   (6)..(6)
<223>   Phe is (D,L)-alpha-Me-Phe(penta-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)

<400>   350

His Ala Asp Gly Leu Phe Thr Ser Asp Xaa Xaa
1               5                   10

<210>   351
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MOD_RES
```

```
<222>   (5)..(5)
<223>   Nle

<220>
<221>   MISC_FEATURE
<222>   (6)..(6)
<223>   Phe is (D,L)-alpha-Me-Phe(penta-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)

<400>   351

His Xaa Asp Gly Leu Phe Thr Ser Asp Xaa Xaa
1               5                   10

<210>   352
<211>   11
<212>   PRT
<213>   Artificial Sequence

<220>
<223>   Synthetic Peptide

<220>
<221>   MISC_FEATURE
<222>   (6)..(6)
<223>   Phe is D-Phe(2,6-di-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   352

His Ala Glu Gly Thr Phe Thr Ser Asp Xaa Xaa
1               5                   10

<210>   353
<211>   11
<212>   PRT
<213>   Artificial Sequence
```

```
<220>
<223>   Synthetic Peptide

<220>
<221>   MISC_FEATURE
<222>   (2)..(2)
<223>   X is aminoisobutyric acid

<220>
<221>   MISC_FEATURE
<222>   (6)..(6)
<223>   Phe is D-Phe(2,6-di-Fluoro)

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   353

His Xaa Asp Gly Thr Phe Thr Ser Asp Xaa Xaa
1               5                   10

<210>   354
<211>   11
<212>   PRT
<213>   Artificial Sequence

<220>
<223>   Synthetic Peptide

<220>
<221>   MISC_FEATURE
<222>   (6)..(6)
<223>   Phe is (D,L)-alpha-Me-Phe(penta-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)

<400>   354

His Ala Glu Gly Thr Phe Thr Ser Asp Xaa Xaa
1               5                   10
```

```
<210>  355
<211>  11
<212>  PRT
<213>  Artificial Sequence

<220>
<223>  Synthetic Peptide

<220>
<221>  MISC_FEATURE
<222>  (6)..(6)
<223>  Phe is (D,L)-alpha-Me-Phe(penta-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)

<400>  355

His Ala Asp Gly Thr Phe Thr Ser Asp Xaa Xaa
1               5                   10

<210>  356
<211>  11
<212>  PRT
<213>  Artificial Sequence

<220>
<223>  Synthetic Peptide

<220>
<221>  MISC_FEATURE
<222>  (6)..(6)
<223>  Phe is (D,L)-alpha-Me-Phe(penta-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)

<400>  356

His Ala Glu Gly Thr Phe Thr Ser Asp Xaa Xaa
1               5                   10
```

```
<210>   357
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(11)
<223>   X is biphenylalanine(2-Et)

<400>   357

His Ala Asp Gly Thr Phe Thr Ser Asp Xaa Xaa
1               5                   10

<210>   358
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   358

His Xaa Asp Gly Thr Phe Thr Ser Asp Xaa Xaa
```

```
<210>  359
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3-OH)

<220>
<221>  MISC_FEATURE
<222>  (11)..(11)
<223>  X is biphenylalanine(3-Me)

<400>  359

His Ala Glu Gly Thr Phe Thr Ser Asp Xaa Xaa
1               5                   10

<210>  360
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(4-OH)

<220>
<221>  MISC_FEATURE
<222>  (11)..(11)
<223>  X is biphenylalanine(2-Me)

<400>  360
```

```
His Ala Glu Gly Thr Phe Thr Ser Asp Xaa Xaa
1               5                   10
```

<210> 361
<211> 11
<212> PRT
<213> Artificial Sequence

<220>
<223> Synthetic Peptide

<220>
<221> MISC_FEATURE
<222> (6)..(6)
<223> Phe is L-alpha-Me-phe

<220>
<221> MISC_FEATURE
<222> (10)..(10)
<223> X is biphenylalanine(2-OEt)

<220>
<221> MISC_FEATURE
<222> (11)..(11)
<223> X is biphenylalanine(2-Me)

<400> 361

```
His Ala Glu Gly Thr Phe Thr Ser Asp Xaa Xaa
1               5                   10
```

<210> 362
<211> 11
<212> PRT
<213> Artificial Sequence

<220>
<223> Synthetic Peptide

<220>
<221> MISC_FEATURE
<222> (6)..(6)

<223> Phe is L-alpha-Me-phe

<220>
<221> MISC_FEATURE
<222> (10)..(10)
<223> X is biphenylalanine(3-OEt)

<220>
<221> MISC_FEATURE
<222> (11)..(11)
<223> X is biphenylalanine(3-Me)

```
<400>  362

His Ala Glu Gly Thr Phe Thr Ser Asp Xaa Xaa
1               5                   10

<210>  363
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3-OCF3)

<220>
<221>  MISC_FEATURE
<222>  (11)..(11)
<223>  X is biphenylalanine(2-Me)

<400>  363

His Ala Glu Gly Thr Phe Thr Ser Asp Xaa Xaa
1               5                   10

<210>  364
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3-NO2)

<220>
<221>  MISC_FEATURE
<222>  (11)..(11)
```

```
<223>   X is biphenylalanine(2-Me)

<400>   364

His Ala Glu Gly Thr Phe Thr Ser Asp Xaa Xaa
1               5                   10

<210>   365
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(3-CF3)

<220>
<221>   MISC_FEATURE
<222>   (11)..(11)
<223>   X is biphenylalanine(2-Me)

<400>   365

His Ala Glu Gly Thr Phe Thr Ser Asp Xaa Xaa
1               5                   10

<210>   366
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(3-Phe)

<220>
<221>   MISC_FEATURE
```

```
<222>   (11)..(11)
<223>   X is biphenylalanine(2-Me)

<400>   366

His Ala Glu Gly Thr Phe Thr Ser Asp Xaa Xaa
1               5                   10

<210>   367
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(3-Cl)

<220>
<221>   MISC_FEATURE
<222>   (11)..(11)
<223>   X is biphenylalanine(2-Me)

<400>   367

His Ala Glu Gly Thr Phe Thr Ser Asp Xaa Xaa
1               5                   10

<210>   368
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(3-Ph)

<220>
```

```
<221>  MISC_FEATURE
<222>  (11)..(11)
<223>  X is biphenylalanine(2-Me)

<400>  368

His Ala Glu Gly Thr Phe Thr Ser Asp Xaa Xaa
1               5                   10

<210>  369
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3-Et)

<220>
<221>  MISC_FEATURE
<222>  (11)..(11)
<223>  X is biphenylalanine(2-Me)

<400>  369

His Ala Glu Gly Thr Phe Thr Ser Asp Xaa Xaa
1               5                   10

<210>  370
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3-i-Pr)
```

```
<220>
<221>  MISC_FEATURE
<222>  (11)..(11)
<223>  X is biphenylalanine(2-Me)

<400>  370

His Ala Glu Gly Thr Phe Thr Ser Asp Xaa Xaa
1               5                   10

<210>  371
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(4-i-Pr)

<220>
<221>  MISC_FEATURE
<222>  (11)..(11)
<223>  X is biphenylalanine(2-Me)

<400>  371

His Ala Glu Gly Thr Phe Thr Ser Asp Xaa Xaa
1               5                   10

<210>  372
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(4-Pr)
```

```
<220>
<221>  MISC_FEATURE
<222>  (11)..(11)
<223>  X is biphenylalanine(2-Me)

<400>  372

His Ala Glu Gly Thr Phe Thr Ser Asp Xaa Xaa
1               5                   10

<210>  373
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3-Pr)

<220>
<221>  MISC_FEATURE
<222>  (11)..(11)
<223>  X is biphenylalanine(2-Me)

<400>  373

His Ala Glu Gly Thr Phe Thr Ser Asp Xaa Xaa
1               5                   10

<210>  374
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
```

```
<222>   (10)..(10)
<223>   X is biphenylalanine(2,5-di-Cl)

<220>
<221>   MISC_FEATURE
<222>   (11)..(11)
<223>   X is biphenylalanine(2-Me)

<400>   374

His Ala Glu Gly Thr Phe Thr Ser Asp Xaa Xaa
1               5                   10

<210>   375
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2,5-di-Phe)

<220>
<221>   MISC_FEATURE
<222>   (11)..(11)
<223>   X is biphenylalanine(2-Me)

<400>   375

His Ala Glu Gly Thr Phe Thr Ser Asp Xaa Xaa
1               5                   10

<210>   376
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe
```

```
<220>
<221>  MISC_FEATURE
<222>  (10)..(10)
<223>  X is biphenylalanine(3,4-di-Phe)

<220>
<221>  MISC_FEATURE
<222>  (11)..(11)
<223>  X is biphenylalanine(2-Me)

<400>  376

His Ala Glu Gly Thr Phe Thr Ser Asp Xaa Xaa
1               5                   10

<210>  377
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3,4-di-Cl)

<220>
<221>  MISC_FEATURE
<222>  (11)..(11)
<223>  X is biphenylalanine(2-Me)

<400>  377

His Ala Glu Gly Thr Phe Thr Ser Asp Xaa Xaa
1               5                   10

<210>  378
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe
```

```
<220>
<221>  MISC_FEATURE
<222>  (10)..(10)
<223>  X is biphenylalanine(2,3-di-Cl)

<220>
<221>  MISC_FEATURE
<222>  (11)..(11)
<223>  X is biphenylalanine(2-Me)

<400>  378

His Ala Glu Gly Thr Phe Thr Ser Asp Xaa Xaa
1               5                   10

<210>  379
<211>  11
<212>  PRT
<213>  Artificial Sequence

<220>
<223>  Synthetic Peptide

<220>
<221>  MISC_FEATURE
<222>  (6)..(6)
<223>  Phe is L-alpha-Me-phe

<220>
<221>  MISC_FEATURE
<222>  (10)..(10)
<223>  X is biphenylalanine(3-NHAc)

<220>
<221>  MISC_FEATURE
<222>  (11)..(11)
<223>  X is biphenylalanine(2-Me)

<400>  379

His Ala Glu Gly Thr Phe Thr Ser Asp Xaa Xaa
1               5                   10

<210>  380
<211>  11
<212>  PRT
<213>  Artificial Sequence

<220>
<223>  Synthetic Peptide

<220>
<221>  MISC_FEATURE
<222>  (6)..(6)
```

```
<223>   Phe is L-alpha-Me-phe

<220>
<221>   MISC_FEATURE
<222>   (10)..(10)
<223>   X is biphenylalanine(4-NHAc)

<220>
<221>   MISC_FEATURE
<222>   (11)..(11)
<223>   X is biphenylalanine(2-Me)

<400>   380

His Ala Glu Gly Thr Phe Thr Ser Asp Xaa Xaa
1               5                   10

<210>   381
<211>   11
<212>   PRT
<213>   Artificial Sequence

<220>
<223>   Synthetic Peptide

<220>
<221>   MISC_FEATURE
<222>   (5)..(5)
<223>   X is Aoc

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   381

His Ala Glu Gly Xaa Phe Thr Ser Asp Xaa Xaa
1               5                   10

<210>   382
<211>   11
<212>   PRT
<213>   Artificial Sequence

<220>
```

```
<223>   Synthetic Peptide

<220>
<221>   MOD_RES
<222>   (5)..(5)
<223>   Nle

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   382

His Ala Asp Gly Leu Phe Thr Ser Asp Xaa Xaa
1               5                   10

<210>   383
<211>   11
<212>   PRT
<213>   Artificial Sequence

<220>
<223>   Synthetic Peptide

<220>
<221>   MISC_FEATURE
<222>   (6)..(6)
<223>   Phe is L-alpha-Me-phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   383

His Ala Glu Gly Thr Phe Thr Ser Asp Xaa Xaa
1               5                   10

<210>   384
<211>   11
<212>   PRT
<213>   Artificial Sequence
```

```
<220>
<223>   Synthetic Peptide

<220>
<221>   MISC_FEATURE
<222>   (2)..(2)
<223>   X is aminoisobutyric acid

<220>
<221>   MOD_RES
<222>   (5)..(5)
<223>   Nle

<220>
<221>   MISC_FEATURE
<222>   (6)..(6)
<223>   Phe is (D,L)-alpha-Et-Phe

<220>
<221>   MISC_FEATURE
<222>   (10)..(10)
<223>   X is biphenylalanine(2-Et)

<220>
<221>   MISC_FEATURE
<222>   (11)..(11)
<223>   X is biphenylalanine(2-Me)

<400>   384

His Xaa Asp Gly Leu Phe Thr Ser Asp Xaa Xaa
1               5                   10

<210>   385
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MISC_FEATURE
<222>   (6)..(6)
<223>   Phe is L-alpha-Me-phe

<220>
<221>   MISC_FEATURE
<222>   (8)..(8)
<223>   Ser is (D,L)-alpha-Me-Ser
```

```
<220>
<221>    MISC_FEATURE
<222>    (10)..(10)
<223>    X is biphenylalanine(2-Et)

<220>
<221>    MISC_FEATURE
<222>    (11)..(11)
<223>    X is biphenylalanine(2-Me)

<400>    385

His Xaa Asp Gly Thr Phe Thr Ser Asp Xaa Xaa
1               5                   10

<210>    386
<211>    11
<212>    PRT
<213>    Artificial Sequence

<220>
<223>    Synthetic Peptide

<220>
<221>    MISC_FEATURE
<222>    (6)..(6)
<223>    Phe is (L)-alpha-Me-Phe(2,6-di-Fluoro)

<220>
<221>    MISC_FEATURE
<222>    (10)..(10)
<223>    X is biphenylalanine(2-Et,4-OMe)

<220>
<221>    MISC_FEATURE
<222>    (11)..(11)
<223>    X is biphenylalanine(2-Me)

<400>    386

His Ala Asp Gly Thr Phe Thr Ser Asp Xaa Xaa
1               5                   10

<210>    387
<211>    11
<212>    PRT
<213>    Artificial Sequence

<220>
<223>    Synthetic Peptide

<220>
<221>    MISC_FEATURE
<222>    (6)..(6)
<223>    Phe is L-alpha-Me-phe
```

```
<220>
<221>  MISC_FEATURE
<222>  (10)..(10)
<223>  X is biphenylalanine(4-t-Bu)

<220>
<221>  MISC_FEATURE
<222>  (11)..(11)
<223>  X is biphenylalanine(2-Me)

<400>  387

His Ala Glu Gly Thr Phe Thr Ser Asp Xaa Xaa
1               5                   10

<210>  388
<211>  11
<212>  PRT
<213>  Artificial Sequence

<220>
<223>  Synthetic Peptide

<220>
<221>  MOD_RES
<222>  (5)..(5)
<223>  Nle

<220>
<221>  MISC_FEATURE
<222>  (6)..(6)
<223>  Phe is (L)-alpha-Me-Phe(2,6-di-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)

<400>  388

His Ala Glu Gly Leu Phe Thr Ser Asp Xaa Xaa
1               5                   10

<210>  389
<211>  11
<212>  PRT
<213>  Artificial Sequence

<220>
<223>  Synthetic Peptide
```

```
<220>
<221>  MOD_RES
<222>  (5)..(5)
<223>  Nle

<220>
<221>  MISC_FEATURE
<222>  (6)..(6)
<223>  Phe is (L)-alpha-Me-Phe(2,6-di-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)

<400>  389

His Ala Asp Gly Leu Phe Thr Ser Asp Xaa Xaa
1               5                   10

<210>  390
<211>  11
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MOD_RES
<222>  (5)..(5)
<223>  Nle

<220>
<221>  MISC_FEATURE
<222>  (6)..(6)
<223>  Phe is (L)-alpha-Me-Phe(2,6-di-Fluoro)

<220>
<221>  MISC_FEATURE
<222>  (10)..(10)
<223>  X is biphenylalanine(2-Et,4-OMe)

<220>
<221>  MISC_FEATURE
```

```
<222>   (11)..(11)
<223>   X is biphenylalanine(2-Me)

<400>   390

His Xaa Glu Gly Leu Phe Thr Ser Asp Xaa Xaa
1               5                   10

<210>   391
<211>   11
<212>   PRT
<213>   Artificial Sequence

<220>
<223>   Synthetic Peptide

<220>
<221>   MISC_FEATURE
<222>   (2)..(2)
<223>   X is aminoisobutyric acid

<220>
<221>   MOD_RES
<222>   (5)..(5)
<223>   Nle

<220>
<221>   MISC_FEATURE
<222>   (6)..(6)
<223>   Phe is (L)-alpha-Me-Phe(2,6-di-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)

<400>   391

His Xaa Asp Gly Leu Phe Thr Ser Asp Xaa Xaa
1               5                   10

<210>   392
<211>   11
<212>   PRT
<213>   Artificial Sequence

<220>
<223>   Synthetic Peptide

<220>
```

```
<221>  MOD_RES
<222>  (5)..(5)
<223>  Nle

<220>
<221>  MISC_FEATURE
<222>  (6)..(6)
<223>  Phe is (L)-alpha-Me-Phe(2,6-di-Fluoro)

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me)

<400>  392

His Ala Asp Gly Leu Phe Thr Ser Asp Xaa Xaa
1               5                   10

<210>  393
<211>  11
<212>  PRT
<213>  Artificial Sequence

<220>
<223>  Synthetic Peptide

<220>
<221>  MISC_FEATURE
<222>  (10)..(10)
<223>  X is biphenylalanine(2-Et)

<220>
<221>  MISC_FEATURE
<222>  (11)..(11)
<223>  X is biphenylalanine(2-Me

<400>  393

His Ala Asp Gly Thr Phe Thr Ser Asp Xaa Xaa
1               5                   10

<210>  394
<211>  11
<212>  PRT
<213>  Artificial Sequence

<220>
<223>  Synthetic Peptide
```

```
<220>
<221>  BINDING
<222>  (1)..(1)
<223>  Acetyl

<220>
<221>  MISC_FEATURE
<222>  (10)..(11)
<223>  X is biphenylalanine

<400>  394

His Ala Glu Gly Thr Phe Thr Ser Asp Xaa Xaa
1               5                   10

<210>  395
<211>  11
<212>  PRT
<213>  Artificial Sequence

<220>
<223>  Synthetic Peptide

<220>
<221>  BINDING
<222>  (1)..(1)
<223>  beta-Ala

<220>
<221>  MISC_FEATURE
<222>  (10)..(11)
<223>  X is biphenylalanine

<400>  395

His Ala Glu Gly Thr Phe Thr Ser Asp Xaa Xaa
1               5                   10

<210>  396
<211>  11
<212>  PRT
<213>  Artificial Sequence

<220>
<223>  Synthetic Peptide

<220>
<221>  BINDING
<222>  (1)..(1)
<223>  Ahx

<220>
<221>  MISC_FEATURE
<222>  (10)..(11)
<223>  X is biphenylalanine
```

```
<400>  396

His Ala Glu Gly Thr Phe Thr Ser Asp Xaa Xaa
1               5                   10

<210>  397
<211>  11
<212>  PRT
<213>  Artificial Sequence

<220>
<223>  Synthetic Peptide

<220>
<221>  BINDING
<222>  (1)..(1)
<223>  Asp

<220>
<221>  MISC_FEATURE
<222>  (10)..(11)
<223>  X is biphenylalanine

<400>  397

His Ala Glu Gly Thr Phe Thr Ser Asp Xaa Xaa
1               5                   10

<210>  398
<211>  11
<212>  PRT
<213>  Artificial Sequence

<220>
<223>  Synthetic Peptide

<220>
<221>  BINDING
<222>  (1)..(1)
<223>  Glu

<220>
<221>  MISC_FEATURE
<222>  (10)..(11)
<223>  X is biphenylalanine

<400>  398

His Ala Glu Gly Thr Phe Thr Ser Asp Xaa Xaa
1               5                   10

<210>  399
<211>  11
```

```
<212>   PRT
<213>   Artificial Sequence

<220>
<223>   Synthetic Peptide

<220>
<221>   BINDING
<222>   (1)..(1)
<223>   Phe

<220>
<221>   MISC_FEATURE
<222>   (10)..(11)
<223>   X is biphenylalanine

<400>   399

His Ala Glu Gly Thr Phe Thr Ser Asp Xaa Xaa
1               5                   10

<210>   400
<211>   11
<212>   PRT
<213>   Artificial Sequence

<220>
<223>   Synthetic Peptide

<220>
<221>   BINDING
<222>   (1)..(1)
<223>   Gly

<220>
<221>   MISC_FEATURE
<222>   (10)..(11)
<223>   X is biphenylalanine

<400>   400

His Ala Glu Gly Thr Phe Thr Ser Asp Xaa Xaa
1               5                   10

<210>   401
<211>   11
<212>   PRT
<213>   Artificial Sequence

<220>
<223>   Synthetic Peptide

<220>
<221>   BINDING
```

```
<222>   (1)..(1)
<223>   Lys

<220>
<221>   MISC_FEATURE
<222>   (10)..(11)
<223>   X is biphenylalanine

<400>   401

His Ala Glu Gly Thr Phe Thr Ser Asp Xaa Xaa
1               5                   10

<210>   402
<211>   11
<212>   PRT
<213>   Artificial Sequence

<220>
<223>   Synthetic Peptide

<220>
<221>   BINDING
<222>   (1)..(1)
<223>   Nva

<220>
<221>   MISC_FEATURE
<222>   (10)..(11)
<223>   X is biphenylalanine

<400>   402

His Ala Glu Gly Thr Phe Thr Ser Asp Xaa Xaa
1               5                   10

<210>   403
<211>   11
<212>   PRT
<213>   Artificial Sequence

<220>
<223>   Synthetic Peptide

<220>
<221>   BINDING
<222>   (1)..(1)
<223>   Asn

<220>
<221>   MISC_FEATURE
<222>   (10)..(11)
<223>   X is biphenylalanine
```

```
<400>   403

His Ala Glu Gly Thr Phe Thr Ser Asp Xaa Xaa
1               5                   10

<210>   404
<211>   11
<212>   PRT
<213>   Artificial Sequence

<220>
<223>   Synthetic Peptide

<220>
<221>   BINDING
<222>   (1)..(1)
<223>   Arg

<220>
<221>   MISC_FEATURE
<222>   (10)..(11)
<223>   X is biphenylalanine

<400>   404

His Ala Glu Gly Thr Phe Thr Ser Asp Xaa Xaa
1               5                   10

<210>   405
<211>   11
<212>   PRT
<213>   Artificial Sequence

<220>
<223>   Synthetic Peptide

<220>
<221>   BINDING
<222>   (1)..(1)
<223>   Ser

<220>
<221>   MISC_FEATURE
<222>   (10)..(11)
<223>   X is biphenylalanine

<400>   405

His Ala Glu Gly Thr Phe Thr Ser Asp Xaa Xaa
1               5                   10

<210>   406
```

```
<211>  11
<212>  PRT
<213>  Artificial Sequence

<220>
<223>  Synthetic Peptide

<220>
<221>  BINDING
<222>  (1)..(1)
<223>  Thr

<220>
<221>  MISC_FEATURE
<222>  (10)..(11)
<223>  X is biphenylalanine

<400>  406

His Ala Glu Gly Thr Phe Thr Ser Asp Xaa Xaa
1               5                   10

<210>  407
<211>  11
<212>  PRT
<213>  Artificial Sequence

<220>
<223>  Synthetic Peptide

<220>
<221>  BINDING
<222>  (1)..(1)
<223>  Val

<220>
<221>  MISC_FEATURE
<222>  (10)..(11)
<223>  X is biphenylalanine

<400>  407

His Ala Glu Gly Thr Phe Thr Ser Asp Xaa Xaa
1               5                   10

<210>  408
<211>  11
<212>  PRT
<213>  Artificial Sequence

<220>
<223>  Synthetic Peptide

<220>
```

```
<221>  BINDING
<222>  (1)..(1)
<223>  Trp

<220>
<221>  MISC_FEATURE
<222>  (10)..(11)
<223>  X is biphenylalanine

<400>  408

His Ala Glu Gly Thr Phe Thr Ser Asp Xaa Xaa
1               5                   10

<210>  409
<211>  11
<212>  PRT
<213>  Artificial Sequence

<220>
<223>  Synthetic Peptide

<220>
<221>  BINDING
<222>  (1)..(1)
<223>  Tyr

<220>
<221>  MISC_FEATURE
<222>  (10)..(11)
<223>  X is biphenylalanine

<400>  409

His Ala Glu Gly Thr Phe Thr Ser Asp Xaa Xaa
1               5                   10

<210>  410
<211>  11
<212>  PRT
<213>  Artificial Sequence

<220>
<223>  Synthetic Peptide

<220>
<221>  BINDING
<222>  (1)..(1)
<223>  Caprolactam

<220>
<221>  MISC_FEATURE
<222>  (10)..(11)
<223>  X is biphenylalanine
```

```
<400>  410

His Ala Glu Gly Thr Phe Thr Ser Asp Xaa Xaa
1               5                   10

<210>  411
<211>  11
<212>  PRT
<213>  Artificial Sequence

<220>
<223>  Synthetic Peptide

<220>
<221>  BINDING
<222>  (1)..(1)
<223>  biphenylalanine

<220>
<221>  MISC_FEATURE
<222>  (10)..(11)
<223>  X is biphenylalanine

<400>  411

His Ala Glu Gly Thr Phe Thr Ser Asp Xaa Xaa
1               5                   10

<210>  412
<211>  11
<212>  PRT
<213>  Artificial Sequence

<220>
<223>  Synthetic Peptide

<220>
<221>  BINDING
<222>  (1)..(1)
<223>  Ser(Bzl)

<220>
<221>  MISC_FEATURE
<222>  (10)..(11)
<223>  X is biphenylalanine

<400>  412

His Ala Glu Gly Thr Phe Thr Ser Asp Xaa Xaa
1               5                   10

<210>  413
<211>  11
<212>  PRT
```

```
<213>   Artificial Sequence

<220>
<223>   Synthetic Peptide

<220>
<221>   BINDING
<222>   (1)..(1)
<223>   3-pyridylAla

<220>
<221>   MISC_FEATURE
<222>   (10)..(11)
<223>   X is biphenylalanine

<400>   413

His Ala Glu Gly Thr Phe Thr Ser Asp Xaa Xaa
1               5                   10

<210>   414
<211>   11
<212>   PRT
<213>   Artificial Sequence

<220>
<223>   Synthetic Peptide

<220>
<221>   BINDING
<222>   (1)..(1)
<223>   Phe(4-Me)

<220>
<221>   MISC_FEATURE
<222>   (10)..(11)
<223>   X is biphenylalanine

<400>   414

His Ala Glu Gly Thr Phe Thr Ser Asp Xaa Xaa
1               5                   10

<210>   415
<211>   11
<212>   PRT
<213>   Artificial Sequence

<220>
<223>   Synthetic Peptide

<220>
<221>   BINDING
```

```
<222>    (1)..(1)
<223>    Phe(pentafluoro)

<220>
<221>    MISC_FEATURE
<222>    (10)..(11)
<223>    X is biphenylalanine

<400>    415

His Ala Glu Gly Thr Phe Thr Ser Asp Xaa Xaa
1               5                   10

<210>    416
<211>    11
<212>    PRT
<213>    Artificial Sequence

<220>
<223>    Synthetic Peptide

<220>
<221>    BINDING
<222>    (1)..(1)
<223>    4-Methylbenzyl

<220>
<221>    MISC_FEATURE
<222>    (10)..(11)
<223>    X is biphenylalanine(2-Me)

<400>    416

His Ala Glu Gly Thr Phe Thr Ser Asp Xaa Xaa
1               5                   10

<210>    417
<211>    11
<212>    PRT
<213>    Artificial Sequence

<220>
<223>    Synthetic Peptide

<220>
<221>    BINDING
<222>    (1)..(1)
<223>    4-Fluorobenzyl

<220>
<221>    MISC_FEATURE
<222>    (10)..(11)
<223>    X is biphenylalanine(2-Me)

<400>    417
```

```
His Ala Glu Gly Thr Phe Thr Ser Asp Xaa Xaa
1               5                   10

<210>   418
<211>   11
<212>   PRT
<213>   Artificial Sequence

<220>
<223>   Synthetic Peptide

<220>
<221>   BINDING
<222>   (1)..(1)
<223>   Propyl

<220>
<221>   MISC_FEATURE
<222>   (10)..(11)
<223>   X is biphenylalanine(2-Me)

<400>   418

His Ala Glu Gly Thr Phe Thr Ser Asp Xaa Xaa
1               5                   10

<210>   419
<211>   11
<212>   PRT
<213>   Artificial Sequence

<220>
<223>   Synthetic Peptide

<220>
<221>   BINDING
<222>   (1)..(1)
<223>   Hexyl

<220>
<221>   MISC_FEATURE
<222>   (10)..(11)
<223>   X is biphenylalanine(2-Me)

<400>   419

His Ala Glu Gly Thr Phe Thr Ser Asp Xaa Xaa
1               5                   10

<210>   420
<211>   11
<212>   PRT
<213>   Artificial Sequence
```

```
<220>
<223>   Synthetic Peptide

<220>
<221>   BINDING
<222>   (1)..(1)
<223>   Cyclohexylmethyl

<220>
<221>   MISC_FEATURE
<222>   (10)..(11)
<223>   X is biphenylalanine(2-Me)

<400>   420

His Ala Glu Gly Thr Phe Thr Ser Asp Xaa Xaa
1               5                   10

<210>   421
<211>   11
<212>   PRT
<213>   Artificial Sequence

<220>
<223>   Synthetic Peptide

<220>
<221>   BINDING
<222>   (1)..(1)
<223>   6-Hydroxypentyl

<220>
<221>   MISC_FEATURE
<222>   (10)..(11)
<223>   X is biphenylalanine(2-Me)

<400>   421

His Ala Glu Gly Thr Phe Thr Ser Asp Xaa Xaa
1               5                   10

<210>   422
<211>   11
<212>   PRT
<213>   Artificial Sequence

<220>
<223>   Synthetic Peptide

<220>
<221>   BINDING
<222>   (1)..(1)
<223>   6-Thienylmethyl
```

```
<220>
<221>  MISC_FEATURE
<222>  (10)..(11)
<223>  X is biphenylalanine(2-Me)

<400>  422

His Ala Glu Gly Thr Phe Thr Ser Asp Xaa Xaa
1               5                   10

<210>  423
<211>  11
<212>  PRT
<213>  Artificial Sequence

<220>
<223>  Synthetic Peptide

<220>
<221>  BINDING
<222>  (1)..(1)
<223>  3-Thienylmethyl

<220>
<221>  MISC_FEATURE
<222>  (10)..(11)
<223>  X is biphenylalanine(2-Me)

<400>  423

His Ala Glu Gly Thr Phe Thr Ser Asp Xaa Xaa
1               5                   10

<210>  424
<211>  11
<212>  PRT
<213>  Artificial Sequence

<220>
<223>  Synthetic Peptide

<220>
<221>  BINDING
<222>  (1)..(1)
<223>  pentafluorobenzyl

<220>
<221>  MISC_FEATURE
<222>  (10)..(11)
<223>  X is biphenylalanine(2-Me)

<400>  424

His Ala Glu Gly Thr Phe Thr Ser Asp Xaa Xaa
```

```
<210>  425
<211>  11
<212>  PRT
<213>  Artificial Sequence

<220>
<223>  Synthetic Peptide

<220>
<221>  BINDING
<222>  (1)..(1)
<223>  2-Naphthylmethyl

<220>
<221>  MISC_FEATURE
<222>  (10)..(11)
<223>  X is biphenylalanine(2-Me)

<400>  425

His Ala Glu Gly Thr Phe Thr Ser Asp Xaa Xaa
1               5                   10

<210>  426
<211>  11
<212>  PRT
<213>  Artificial Sequence

<220>
<223>  Synthetic Peptide

<220>
<221>  BINDING
<222>  (1)..(1)
<223>  4-Biphenylmethyl

<220>
<221>  MISC_FEATURE
<222>  (10)..(11)
<223>  X is biphenylalanine(2-Me)

<400>  426

His Ala Glu Gly Thr Phe Thr Ser Asp Xaa Xaa
1               5                   10

<210>  427
<211>  11
<212>  PRT
<213>  Artificial Sequence

<220>
```

```
<223>   Synthetic Peptide

<220>
<221>   BINDING
<222>   (1)..(1)
<223>   9-Anthracenylmethyl

<220>
<221>   MISC_FEATURE
<222>   (10)..(11)
<223>   X is biphenylalanine(2-Me)

<400>   427

His Ala Glu Gly Thr Phe Thr Ser Asp Xaa Xaa
1               5                   10

<210>   428
<211>   11
<212>   PRT
<213>   Artificial Sequence

<220>
<223>   Synthetic Peptide

<220>
<221>   BINDING
<222>   (1)..(1)
<223>   Benzyl

<220>
<221>   MISC_FEATURE
<222>   (10)..(11)
<223>   X is biphenylalanine(2-Me)

<400>   428

His Ala Glu Gly Thr Phe Thr Ser Asp Xaa Xaa
1               5                   10

<210>   429
<211>   11
<212>   PRT
<213>   Artificial Sequence

<220>
<223>   Synthetic Peptide

<220>
<221>   BINDING
<222>   (1)..(1)
<223>   (S)-(2-Amino-3-phenyl)propyl

<220>
```

```
<221>   MISC_FEATURE
<222>   (10)..(11)
<223>   X is biphenylalanine(2-Me)

<400>   429

His Ala Glu Gly Thr Phe Thr Ser Asp Xaa Xaa
1               5                   10

<210>   430
<211>   11
<212>   PRT
<213>   Artificial Sequence

<220>
<223>   Synthetic Peptide

<220>
<221>   BINDING
<222>   (1)..(1)
<223>   Methyl

<220>
<221>   MISC_FEATURE
<222>   (10)..(11)
<223>   X is biphenylalanine

<400>   430

His Ala Glu Gly Thr Phe Thr Ser Asp Xaa Xaa
1               5                   10

<210>   431
<211>   11
<212>   PRT
<213>   Artificial Sequence

<220>
<223>   Synthetic Peptide

<220>
<221>   BINDING
<222>   (1)..(1)
<223>   Benyzl-

<220>
<221>   MISC_FEATURE
<222>   (10)..(11)
<223>   X is biphenylalanine

<400>   431

His Ala Glu Gly Thr Phe Thr Ser Asp Xaa Xaa
1               5                   10
```

```
<210>   432
<211>   11
<212>   PRT
<213>   Artificial Sequence

<220>
<223>   Synthetic Peptide

<220>
<221>   BINDING
<222>   (1)..(1)
<223>   2-aminoethyl

<220>
<221>   MISC_FEATURE
<222>   (10)..(11)
<223>   X is biphenylalanine(2-Me)

<400>   432

His Ala Glu Gly Thr Phe Thr Ser Asp Xaa Xaa
1               5                   10

<210>   433
<211>   11
<212>   PRT
<213>   Artificial Sequence

<220>
<223>   Synthetic Peptide

<220>
<221>   BINDING
<222>   (1)..(1)
<223>   (S)-2-Aminopropyl

<220>
<221>   MISC_FEATURE
<222>   (10)..(11)
<223>   X is biphenylalanine(2-Me)

<400>   433

His Ala Glu Gly Thr Phe Thr Ser Asp Xaa Xaa
1               5                   10

<210>   434
<211>   12
<212>   PRT
<213>   Artificial Sequence

<220>
<223>   Synthetic Peptide
```

```
<220>
<221>   MISC_FEATURE
<222>   (10)..(10)
<223>   X is biphenylalanine

<220>
<221>   MISC_FEATURE
<222>   (11)..(11)
<223>   X is 2-Nal

<400>   434

His Ala Glu Gly Thr Phe Thr Ser Asp Xaa Xaa Trp
1               5                   10

<210>   435
<211>   12
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   X is Phe(penta-Fluoro)

<220>
<221>   MISC_FEATURE
<222>   (12)..(12)
<223>   X is 2-Nal

<400>   435

His Ala Glu Gly Thr Phe Thr Ser Asp Xaa Phe Xaa
1               5                   10

<210>   436
<211>   12
<212>   PRT
<213>   Artificial Sequence

<220>
<223>   Synthetic Peptide

<220>
<221>   MISC_FEATURE
<222>   (10)..(10)
```

```
<223>   X is biphenylalanine

<220>
<221>   MISC_FEATURE
<222>   (11)..(12)
<223>   Phe is Phe(penta-Fluoro)

<400>   436

His Ala Glu Gly Thr Phe Thr Ser Asp Xaa Phe Phe
1               5                   10

<210>   437
<211>   12
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(penta-Fluoro)

<220>
<221>   MISC_FEATURE
<222>   (12)..(12)
<223>   X is Ser(Bzl)

<400>   437

His Ala Glu Gly Thr Phe Thr Ser Asp Xaa Phe Xaa
1               5                   10

<210>   438
<211>   12
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
```

```
<222>   (11)..(11)
<223>   Phe is Phe(penta-Fluoro)

<220>
<221>   MISC_FEATURE
<222>   (12)..(12)
<223>   Phe is Phe(4-NO2)

<400>   438

His Ala Glu Gly Thr Phe Thr Ser Asp Xaa Phe Phe
1               5                   10

<210>   439
<211>   12
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(penta-Fluoro)

<220>
<221>   MISC_FEATURE
<222>   (12)..(12)

<223>   Ala is 3-PyridylAla

<400>   439

His Ala Glu Gly Thr Phe Thr Ser Asp Xaa Phe Ala
1               5                   10

<210>   440
<211>   12
<212>   PRT
<213>   Artificial Sequence

<220>
<223>   Synthetic Peptide

<220>
<221>   MISC_FEATURE
<222>   (10)..(10)
<223>   X is biphenylalanine
```

```
<220>
<221>  MISC_FEATURE
<222>  (11)..(11)
<223>  Phe is Phe(penta-Fluoro)

<220>
<221>  MOD_RES
<222>  (12)..(12)
<223>  Nva

<400>  440

His Ala Glu Gly Thr Phe Thr Ser Asp Xaa Phe Val
1               5                   10

<210>  441
<211>  12
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
<223>  Phe is Phe(penta-Fluoro)

<400>  441

His Ala Glu Gly Thr Phe Thr Ser Asp Xaa Phe Lys
1               5                   10

<210>  442
<211>  12
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
```

```
<223>   Phe is Phe(penta-Fluoro)

<400>   442

His Ala Glu Gly Thr Phe Thr Ser Asp Xaa Phe Asp
1               5                   10

<210>   443
<211>   12
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(penta-Fluoro)

<400>   443

His Ala Glu Gly Thr Phe Thr Ser Asp Xaa Phe Ser
1               5                   10

<210>   444
<211>   12
<212>   PRT
<213>   Artificial Sequence

<220>
<223>   Synthetic Peptide

<220>
<221>   MISC_FEATURE
<222>   (10)..(10)
<223>   X is biphenylalanine

<220>
<221>   MISC_FEATURE
<222>   (11)..(11)
<223>   Phe is Phe(penta-Fluoro)

<400>   444

His Ala Glu Gly Thr Phe Thr Ser Asp Xaa Phe His
1               5                   10

<210>   445
```

```
<211>  12
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
<223>  Phe is Phe(penta-Fluoro)

<400>  445

His Ala Glu Gly Thr Phe Thr Ser Asp Xaa Phe Tyr
1               5                   10

<210>  446
<211>  12
<212>  PRT
<213>  Artificial Sequence

<220>
<223>  Synthetic Peptide

<220>
<221>  MISC_FEATURE
<222>  (10)..(10)
<223>  X is biphenylalanine

<220>
<221>  MISC_FEATURE
<222>  (11)..(11)
<223>  Phe is Phe(penta-Fluoro)

<400>  446

His Ala Glu Gly Thr Phe Thr Ser Asp Xaa Phe Trp
1               5                   10

<210>  447
<211>  12
<212>  PRT
<213>  Artificial Sequence

<220>
<223>  Synthetic Peptide
```

```
<220>
<221>  MISC_FEATURE
<222>  (10)..(10)
<223>  X is biphenylalanine

<220>
<221>  MISC_FEATURE
<222>  (11)..(11)
<223>  Phe is Phe(penta-Fluoro)

<400>  447

His Ala Glu Gly Thr Phe Thr Ser Asp Xaa Phe Phe
1               5                   10

<210>  448
<211>  12
<212>  PRT
<213>  Artificial Sequence

<220>
<223>  Synthetic Peptide

<220>
<221>  MISC_FEATURE
<222>  (10)..(10)
<223>  X is 2-Nal

<220>
<221>  MISC_FEATURE
<222>  (11)..(11)
<223>  Phe is Phe(penta-Fluoro)

<400>  448

His Ala Glu Gly Thr Phe Thr Ser Asp Xaa Phe Trp
1               5                   10

<210>  449
<211>  12
<212>  PRT
<213>  Artificial Sequence

<220>
<223>  Synthetic Peptide

<220>
<221>  MISC_FEATURE
<222>  (10)..(12)
<223>  X is biphenylalanine

<400>  449

His Ala Glu Gly Thr Phe Thr Ser Asp Xaa Xaa Xaa
1               5                   10
```

```
<210>  450
<211>  12
<212>  PRT
<213>  Artificial Sequence

<220>
<223>  Synthetic Peptide

<220>
<221>  MISC_FEATURE
<222>  (10)..(11)
<223>  X is biphenylalanine

<220>
<221>  MOD_RES
<222>  (12)..(12)

<223>  Nva

<400>  450

His Ala Glu Gly Thr Phe Thr Ser Asp Xaa Xaa Val
1               5                   10

<210>  451
<211>  12
<212>  PRT
<213>  Artificial Sequence

<220>
<223>  Synthetic Peptide

<220>
<221>  MISC_FEATURE
<222>  (10)..(11)
<223>  X is biphenylalanine(2-Me)

<400>  451

His Ala Glu Gly Thr Phe Thr Ser Asp Xaa Xaa Ser
1               5                   10

<210>  452
<211>  12
<212>  PRT
<213>  Artificial Sequence

<220>
<223>  Synthetic Peptide

<220>
```

```
<221>    MISC_FEATURE
<222>    (10)..(11)
<223>    X is biphenylalanine(2-Me)

<220>
<221>    MISC_FEATURE
<222>    (12)..(12)
<223>    Gly is Gly-OH

<400>    452

His Ala Glu Gly Thr Phe Thr Ser Asp Xaa Xaa Gly
1               5                   10

<210>    453
<211>    12
<212>    PRT
<213>    Artificial Sequence

<220>
<223>    Synthetic Peptide

<220>
<221>    MISC_FEATURE
<222>    (10)..(11)
<223>    X is biphenylalanine(2-Me)

<220>
<221>    MISC_FEATURE
<222>    (12)..(12)
<223>    Ala is beta-Ala-OH

<400>    453

His Ala Glu Gly Thr Phe Thr Ser Asp Xaa Xaa Ala
1               5                   10

<210>    454
<211>    12
<212>    PRT
<213>    Artificial Sequence

<220>
<223>    Synthetic Peptide

<220>
<221>    MISC_FEATURE
<222>    (10)..(11)
<223>    X is biphenylalanine(2-Me)

<220>
<221>    MISC_FEATURE
<222>    (12)..(12)
<223>    Gly is GABA-OH
```

```
<400>  454

His Ala Glu Gly Thr Phe Thr Ser Asp Xaa Xaa Gly
1               5                   10

<210>  455
<211>  12
<212>  PRT
<213>  Artificial Sequence

<220>
<223>  Synthetic Peptide

<220>
<221>  MISC_FEATURE
<222>  (10)..(11)
<223>  X is biphenylalanine(2-Me)

<220>
<221>  MISC_FEATURE
<222>  (12)..(12)
<223>  Ala is APA-OH

<400>  455

His Ala Glu Gly Thr Phe Thr Ser Asp Xaa Xaa Ala
1               5                   10

<210>  456
<211>  11
<212>  PRT
<213>  Artificial Sequence

<220>
<223>  Synthetic Peptide

<220>
<221>  BINDING
<222>  (1)..(1)
<223>  Tyr

<220>
<221>  MISC_FEATURE
<222>  (2)..(2)
<223>  X is aminoisobutyric acid

<220>
<221>  MISC_FEATURE
<222>  (6)..(6)
<223>  Phe is (L)-alpha-Me-Phe(2-Fluoro)

<220>
<221>  MISC_FEATURE
<222>  (10)..(10)
<223>  X is biphenylalanine(2-Et,4-OMe)
```

```
<220>
<221>  MISC_FEATURE
<222>  (11)..(11)
<223>  X is biphenylalanine(2-Me)-NH2

<400>  456

Ala Xaa Glu Gly Thr Phe Thr Ser Asp Xaa Xaa
1               5                   10

<210>  457
<211>  11
<212>  PRT
<213>  Artificial Sequence

<220>
<223>  Synthetic Peptide

<220>
<221>  BINDING
<222>  (1)..(1)
<223>  CH3CO

<220>
<221>  MISC_FEATURE
<222>  (2)..(2)
<223>  X is aminoisobutyric acid

<220>
<221>  MISC_FEATURE
<222>  (6)..(6)
<223>  Phe is (L)-alpha-Me-Phe(2-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)-NH2

<400>  457

His Xaa Glu Gly Thr Phe Thr Ser Asp Xaa Xaa
1               5                   10

<210>  458
<211>  11
<212>  PRT
<213>  Artificial Sequence

<220>
<223>  Synthetic Peptide
```

```
<220>
<221>  BINDING
<222>  (1)..(1)
<223>  CH3CO

<220>
<221>  MISC_FEATURE
<222>  (2)..(2)
<223>  X is aminoisobutyric acid

<220>
<221>  MISC_FEATURE
<222>  (6)..(6)
<223>  Phe is (L)-alpha-Me-Phe(2-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)-NH2

<400>  458

His Xaa Glu Gly Thr Phe Thr Ser Asp Xaa Xaa
1               5                   10

<210>  459
<211>  11
<212>  PRT
<213>  Artificial Sequence

<220>
<223>  Synthetic Peptide

<220>
<221>  BINDING
<222>  (1)..(1)
<223>  CH3CH2CO

<220>
<221>  MISC_FEATURE
<222>  (2)..(2)
<223>  X is aminoisobutyric acid

<220>
<221>  MISC_FEATURE
<222>  (6)..(6)
<223>  Phe is (L)-alpha-Me-Phe(2-Fluoro)

<220>
```

```
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)-NH2

<400>  459

His Xaa Glu Gly Thr Phe Thr Ser Asp Xaa Xaa
1               5                   10

<210>  460
<211>  11
<212>  PRT
<213>  Artificial Sequence

<220>
<223>  Synthetic Peptide

<220>
<221>  BINDING
<222>  (1)..(1)
<223>  Des-NH2-Tyr

<220>
<221>  MISC_FEATURE
<222>  (2)..(2)
<223>  X is aminoisobutyric acid

<220>
<221>  MISC_FEATURE
<222>  (6)..(6)
<223>  Phe is (L)-alpha-Me-Phe(2-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)-NH2

<400>  460

His Xaa Glu Gly Thr Phe Thr Ser Asp Xaa Xaa
1               5                   10

<210>  461
<211>  11
<212>  PRT
<213>  Artificial Sequence
```

```
<220>
<223>   Synthetic Peptide

<220>
<221>   BINDING
<222>   (1)..(1)
<223>   CH3OCO

<220>
<221>   MISC_FEATURE
<222>   (2)..(2)
<223>   X is aminoisobutyric acid

<220>
<221>   MISC_FEATURE
<222>   (6)..(6)
<223>   Phe is (L)-alpha-Me-Phe(2-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)-NH2

<400>   461

His Ala Glu Gly Thr Phe Thr Ser Asp Xaa Xaa
1               5                   10

<210>   462
<211>   11
<212>   PRT
<213>   Artificial Sequence

<220>
<223>   Synthetic Peptide

<220>
<221>   BINDING
<222>   (1)..(1)
<223>   CH3NHCO

<220>
<221>   MISC_FEATURE
<222>   (2)..(2)
<223>   X is aminoisobutyric acid

<220>
<221>   MISC_FEATURE
```

```
<222>   (6)..(6)
<223>   Phe is (L)-alpha-Me-Phe(2-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)-NH2

<400>   462

His Xaa Glu Gly Thr Phe Thr Ser Asp Xaa Xaa
1               5                   10

<210>   463
<211>   11
<212>   PRT
<213>   Artificial Sequence

<220>
<223>   Synthetic Peptide

<220>
<221>   BINDING
<222>   (1)..(1)
<223>   CH3SO2

<220>
<221>   MISC_FEATURE
<222>   (2)..(2)
<223>   X is aminoisobutyric acid

<220>
<221>   MISC_FEATURE
<222>   (6)..(6)
<223>   Phe is (L)-alpha-Me-Phe(2-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)-NH2

<400>   463

His Xaa Glu Gly Thr Phe Thr Ser Asp Xaa Xaa
1               5                   10
```

```
<210>   464
<211>   11
<212>   PRT
<213>   Artificial Sequence

<220>
<223>   Synthetic Peptide

<220>
<221>   BINDING
<222>   (1)..(1)
<223>   (L)-OH-CH(CH3)CO

<220>
<221>   MISC_FEATURE
<222>   (2)..(2)
<223>   X is aminoisobutyric acid

<220>
<221>   MISC_FEATURE
<222>   (6)..(6)
<223>   Phe is (L)-alpha-Me-Phe(2-Fluoro)

<220>
<221>   MISC_FEATURE
<222>   (10)..(10)
<223>   X is biphenylalanine(2-Et,4-OMe)

<220>
<221>   MISC_FEATURE
<222>   (11)..(11)
<223>   X is biphenylalanine(2-Me)-NH2

<400>   464

His Xaa Glu Gly Thr Phe Thr Ser Asp Xaa Xaa
1               5                   10

<210>   465
<211>   11
<212>   PRT
<213>   Artificial Sequence

<220>
<223>   Synthetic Peptide

<220>
<221>   BINDING
<222>   (1)..(1)
<223>   HO-CH2-CO-

<220>
<221>   MISC_FEATURE
<222>   (2)..(2)
<223>   X is aminoisobutyric acid
```

```
<220>
<221>  MISC_FEATURE
<222>  (6)..(6)
<223>  Phe is (L)-alpha-Me-Phe(2-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)-NH2

<400>  465

His Xaa Glu Gly Thr Phe Thr Ser Asp Xaa Xaa
1               5                   10

<210>  466
<211>  12
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is (L)-alpha-Me-Phe(2-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)

<220>
<221>  MISC_FEATURE
<222>  (12)..(12)
<223>  Gly is Gly-OH

<400>  466

His Ala Glu Gly Thr Phe Thr Ser Asp Xaa Xaa Gly
```

```
<210>  467
<211>  12
<212>  PRT
<213>  Artificial Sequence

<220>
<223>  Synthetic Peptide

<220>
<221>  MISC_FEATURE
<222>  (2)..(2)
<223>  X is aminoisobutyric acid

<220>
<221>  MISC_FEATURE
<222>  (6)..(6)
<223>  Phe is (L)-alpha-Me-Phe(2-Fluoro)

<220>
<221>  MISC_FEATURE
<222>  (10)..(10)
<223>  X is biphenylalanine(2-Et,4-OMe)

<220>
<221>  MISC_FEATURE
<222>  (11)..(11)
<223>  X is biphenylalanine(2-Me)

<220>
<221>  MISC_FEATURE
<222>  (12)..(12)
<223>  Ala is beta-Ala-OH

<400>  467

His Xaa Glu Gly Thr Phe Thr Ser Asp Xaa Xaa Ala
1               5                   10

<210>  468
<211>  12
<212>  PRT
<213>  Artificial Sequence

<220>
<223>  Synthetic Peptide

<220>
<221>  MISC_FEATURE
<222>  (2)..(2)
<223>  X is aminoisobutyric acid
```

```
<220>
<221>    MISC_FEATURE
<222>    (6)..(6)
<223>    Phe is (L)-alpha-Me-Phe(2-Fluoro)

<220>
<221>    MISC_FEATURE
<222>    (10)..(10)
<223>    X is biphenylalanine(2-Et,4-OMe)

<220>
<221>    MISC_FEATURE
<222>    (11)..(11)
<223>    X is biphenylalanine(2-Me)

<220>
<221>    MISC_FEATURE
<222>    (12)..(12)
<223>    Gly is GABA-OH

<400>    468

His Xaa Glu Gly Thr Phe Thr Ser Asp Xaa Xaa Gly
1               5                   10

<210>    469
<211>    5
<212>    PRT
<213>    Artificial Sequence

<220>
<223>    Synthetic Peptide

<220>
<221>    MISC_FEATURE
<222>    (4)..(5)
<223>    X is biphenylalanine

<400>    469

Thr Ser Asp Xaa Xaa
1               5
```

UNITED STATES PATENT AND TRADEMARK OFFICE
CERTIFICATE OF CORRECTION

PATENT NO. : 7,238,671 B2
APPLICATION NO. : 10/419399
DATED : July 3, 2007
INVENTOR(S) : Sesha Iyer Natarajan et al.

It is certified that error appears in the above-identified patent and that said Letters Patent is hereby corrected as shown below:

Column 76
In claim 4, line 66 through 67, delete "glucagon-like peptide-I (GLP-I)" and replace with -- glucagon-like peptide-1 (GLP-1) --

Column 77
In claim 5, line 9, delete "(cis-perhydmisoindol-2yl)" and replace with
-- (cis-perhydroisoindol-2-yl) --

Column 78
In claim 7, line 29, delete "pheniylpropanolamine" and replace with
-- phenylpropanolamine --

In claim 14, line 5, insert -- a -- before PPAR.

In claim 14, line 7 through 8, delete "glucagon-like peptide-I (GLP-I)" and replace with
-- glucagon-like peptide-1 (GLP-1) --

In claim 15, line 22, delete "glucagon-like peptide I" and replace with
-- glucagon-like peptide-1 --

In claim 17, line 36 through 37, delete "phenylprapanolamine" and replace with
-- phenylpropanolamine --

In claim 18, line 43, delete "trio" and replace with -- fibric --

Signed and Sealed this

Twenty-second Day of July, 2008

JON W. DUDAS
*Director of the United States Patent and Trademark Office*